US009492682B2

(12) United States Patent
Gold et al.

(10) Patent No.: US 9,492,682 B2
(45) Date of Patent: Nov. 15, 2016

(54) COMBINATION THERAPY WITH LOW DOSAGE STRENGTH IMIQUIMOD AND PHOTODYNAMIC THERAPY TO TREAT ACTINIC KERATOSIS

(75) Inventors: Michael H. Gold, Nashville, TN (US); Joel L. Cohen, Denver, CO (US); Girish S. Munavalli, Charlotte, NC (US); Tze-Chiang Meng, Lino Lakes, MN (US)

(73) Assignee: Medicis Pharmaceutical Corporation, Bridgewater, NJ (US)

( * ) Notice: Subject to any disclaimer, the term of this patent is extended or adjusted under 35 U.S.C. 154(b) by 220 days.

(21) Appl. No.: 13/619,983

(22) Filed: Sep. 14, 2012

(65) Prior Publication Data

US 2013/0190715 A1  Jul. 25, 2013

Related U.S. Application Data

(60) Provisional application No. 61/534,876, filed on Sep. 14, 2011, provisional application No. 61/535,276, filed on Sep. 15, 2011.

(51) Int. Cl.
| | |
|---|---|
| *A61N 5/06* | (2006.01) |
| *A61K 31/4745* | (2006.01) |
| *A61K 41/00* | (2006.01) |
| *A61K 8/49* | (2006.01) |
| *A61Q 19/00* | (2006.01) |
| *A61K 9/00* | (2006.01) |

(52) U.S. Cl.
CPC ............. *A61N 5/062* (2013.01); *A61K 8/4946* (2013.01); *A61K 9/0014* (2013.01); *A61K 31/4745* (2013.01); *A61K 41/0061* (2013.01); *A61Q 19/004* (2013.01); *A61K 2800/81* (2013.01)

(58) Field of Classification Search
CPC ........... A61B 2017/22087; A61M 2001/3683; A61N 5/06; A61N 5/062
USPC ............. 128/878, 898; 604/19, 20, 500, 501
See application file for complete search history.

(56) References Cited

U.S. PATENT DOCUMENTS

| | | | |
|---|---|---|---|
| 4,689,338 | A | 8/1987 | Gerster |
| 5,238,944 | A | 8/1993 | Wick et al. |
| 6,693,113 | B2 | 2/2004 | Lindstrom |
| 6,894,060 | B2 | 5/2005 | Slade |
| 7,038,051 | B2 | 5/2006 | Gerster |
| 8,080,560 | B2 | 12/2011 | Statham et al. |

(Continued)

FOREIGN PATENT DOCUMENTS

WO    WO-2010/080345 A1 *  7/2010

OTHER PUBLICATIONS

U.S. Appl. No. 13/168,796, filed Jun. 24, 2011, Nordsiek et al.

(Continued)

*Primary Examiner* — Gerald Landry, II
(74) *Attorney, Agent, or Firm* — Kilpatrick Townsend & Stockton LLP

(57) ABSTRACT

This disclosure is directed to the use of sequentially applied topical therapy with a lower dosage strength imiquimod composition and photodynamic therapy for treating actinic keratosis, wherein the photodynamic therapy is administered subsequent to the topical therapy with the imiquimod composition. In some embodiments, the imiquimod composition comprises from about 1% (w/w) to about 4.25% (w/w) imiquimod.

15 Claims, 9 Drawing Sheets

(56) References Cited

U.S. PATENT DOCUMENTS

| | | | |
|---|---|---|---|
| 8,222,270 B2* | 7/2012 | Nordsiek | A61K 9/0014 514/290 |
| 8,236,816 B2 | 8/2012 | Nordsiek et al. | |
| 8,299,109 B2 | 10/2012 | Nordsiek et al. | |
| 8,436,045 B2* | 5/2013 | Cuevas Sanchez | 514/517 |
| 2002/0147210 A1 | 10/2002 | Smith | |
| 2004/0181130 A1* | 9/2004 | Miller | A61B 5/0059 600/306 |
| 2005/0079235 A1* | 4/2005 | Stockfleth | A61K 31/353 424/729 |
| 2007/0123558 A1 | 5/2007 | Statham et al. | |
| 2007/0264317 A1 | 11/2007 | Yosha et al. | |
| 2008/0125485 A1* | 5/2008 | Cuevas Sanchez | A61K 31/185 514/546 |
| 2009/0192071 A1* | 7/2009 | Gold et al. | 514/2 |
| 2010/0239565 A1* | 9/2010 | Wilensky | A61K 31/135 424/130.1 |
| 2011/0020441 A1* | 1/2011 | Klaveness et al. | 424/463 |
| 2011/0021555 A1 | 1/2011 | Nordsiek et al. | |
| 2011/0178456 A1* | 7/2011 | Aguilar-Mendoza | A61M 35/00 604/20 |
| 2011/0263635 A1 | 10/2011 | Nordsiek et al. | |
| 2011/0319811 A1 | 12/2011 | Nordsiek et al. | |
| 2012/0035556 A1 | 2/2012 | Nordsiek et al. | |

OTHER PUBLICATIONS

Gaspari A et al., "Beyond a decade of 5% Imiquimod topical therapy," *J Drugs Dermatol* 2009; 8:467-74.

Lebwohl M et al., Imiquimod 5% cream for the treatment of actinic keratosis: Results from two phase III, randomized, double-blind, parallel group, vehicle-controlled trials, *J Am Acad Dermatol* 2004; 50:714-21.

Swanson N et al., "Imiquimod 2.5% and 3.75% for the treatment of actinic keratoses: Results of two placebo-controlled studies of daily application to the face and balding scalp for two 2-week cycles," *J Am Acad Dermatol* 2010; 62:582-90.

Hanke CW et al., "Imiquimod 2.5% and 3.75% for the treatment of actinic keratoses: Results of two placebo-controlled studies of daily application to the face and balding scalp for two 3-week cycles," *J Am Acad Dermatol* 2010; 62:573-81.

Krawtchenko N et al., "A randomised study of topical 5% Imiquimod vs. topical 5-fluorouracil vs. cryosurgery in immunocompetent patients with actinic keratoses: a comparison of clinical and histological outcomes including 1-year follow-up," *Br J Dermatol* 2007; 157(Suppl 2):34-40.

Shaffelburg, "Treatment of actinic keratosis with sequential use of photodynamic and Imiquimod 5% cream," *J Drugs Dermatol.* 2009;8:35-9.

Devirgiliis, et al, "Complete remission of nodular basal cell carcinoma after combined treatment with photodynamic therapy and Imiquimod 5% cream," *Dermatol Online Journal.* 2008;28;14(2):25, 3 pgs.

Maden et al., "Sequential treatment of giant basal cell carcinomas," *J Plast Reconstr Aesthet Surg.* 2009;62:e368-72.

Vereecken et al., "Treatment of Bowen's disease with photodynamic therapy after Imiquimod: the need for controlled trials," *J Eur Acad Dermatol Venereal.* 2006;20:1397-9.

Winters et al., "Clinical and Immunologic Results of a Phase II Trial of Sequential Imiquimod and Photodynamic Therapy for Vulval Intraepithelial Neoplasia," *Clin Cancer Res.* 2008;14:5292-9.

Piacquadio et al., "Photodynamic therapy with aminolevulinic acid topical solution and visible blue light in the treatment of multiple actinic keratosis of the face and scalp," *Arch Dermatol.* Jan 2004; vol. 140:41-6.

Touma et al., "A trial of short incubation, broad-area photodynamic therapy for facial actinic keratosis and diffuse photodamage," *Arch Dermatol.*, Jan. 2004; vol. 140:33-40.

* cited by examiner

FIG. 1

Summary of Primary and Secondary Efficacy Endpoint
Combined Studies, Analysis Within regimen
ITT Population

|  | 2-Week treatment Cycle Regimen | | | 3-Week treatment Cycle Regimen | | |
|---|---|---|---|---|---|---|
|  | 3.75% (N=160) | 2.5% (N=160) | Placebo (N=159) | 3.75% (N=162) | 2.5% (N=164) | Placebo (N=164) |
| Complete Clearance at End of Study | 57/160 (35.6) | 49/160 (30.6) | 10/159 (6.3) | 55/162 (34.0) | 41/164 (25.0) | 9/164 (5.5) |
| 95% confidence interval | 28.2, 43.6 | 23.6, 38.4 | 3.1, 11.3 | 26.7, 41.8 | 18.6, 32.3 | 2.5, 10.2 |
| P value vs Placebo | <.001** | <.001** | . | <.001** | <.001** | . |
| P value vs 2.5% Imiquimod Cream | 0.379 | . | . | 0.082 | . | . |
| Partial Clearance at End of Study | 95/160 (59.4) | 77/160 (48.1) | 36/159 (22.6) | 87/162 (53.7) | 70/164 (42.7) | 21/164 (12.8) |
| 95% confidence interval | 51.3, 67.1 | 40.2, 56.2 | 16.4, 29.9 | 45.7, 61.6 | 35.0, 50.6 | 8.1, 18.9 |
| P value vs Placebo | <.001** | <.001** | . | <.001** | <.001** | . |
| P value vs 2.5% Imiquimod Cream | 0.047** | . | . | 0.034** | . | . |
| Percent Change in Number of AK Lesions from Baseline to End of Study | | | | | | |
| N | 160 | 160 | 159 | 162 | 164 | 164 |
| Mean (Standard Deviation) | -68.7 (43.4) | -59.2 (41.6) | -27.6 (52.1) | -64.3 (43.0) | -57.0 (45.4) | -24.5 (47.0) |
| Median | -81.8 | -71.8 | -25.0 | -80.0 | -66.7 | -23.6 |
| Minimum, Maximum | -100.0 to 188.9 | -100.0 to 90.0 | -100.0 to 300.0 | -100.0 to 160.0 | -100.0 to 183.3 | -100.0 to 200.0 |
| P value vs Placebo | <.001** | <.001** | . | <.001** | <.001** | . |
| P value vs 2.5% Imiquimod Cream | 0.048** | . | . | . | . | . |

FIG. 2

Summary of Primary and Secondary Efficacy Endpoints
2-Week Treatment Cycle Regimen
ITT Population

|  | GW01-0702 ||| GW01-0704 |||
|---|---|---|---|---|---|---|
|  | 3.75% (N=81) | 2.5% (N=81) | Placebo (N=80) | 3.75% (N=79) | 2.5% (N=79) | Placebo (N=79) |
| Complete Clearance at End of Study | 21/81 (25.9) | 19/81 (23.5) | 2/80 (2.5) | 36/79 (45.6) | 30/79 (38.0) | 8/79 (10.1) |
| 95% confidence interval | 16.8, 36.9 | 14.8, 34.2 | 0.3, 8.7 | 34.3, 57.2 | 27.3, 49.5 | 4.5, 19.0 |
| P value vs Placebo | <.001** | <.001** | -- | <.001** | <.001** | -- |
| P value vs 2.5% Imiquimod Cream | 0.777 | -- | -- | 0.368 | -- | -- |
| Partial Clearance at End of Study | 37/81 (45.7) | 34/81 (42.0) | 15/80 (18.8) | 58/79 (73.4) | 43/79 (54.4) | 21/79 (26.6) |
| 95% confidence interval | 34.8, 57.1 | 31.1, 53.5 | 10.9, 29.0 | 62.3, 82.7 | 42.8, 65.7 | 17.3, 37.7 |
| P value vs Placebo | <.001** | <.001** | -- | <.001** | <.001** | -- |
| P value vs 2.5% Imiquimod Cream | 0.693 | -- | -- | 0.014** | -- | -- |
| Percent Change in Number of AK Lesions From Baseline to End of Study |  |  |  |  |  |  |
| N | 81 | 81 | 80 | 79 | 79 | 79 |
| Mean (Standard Deviation) | -59.7 (44.4) | -52.8 (42.4) | -22.7 (55.3) | -77.9 (40.5) | -65.9 (40.0) | -32.5 (48.5) |
| Median | -72.7 | -60.0 | -21.1 | -90.9 | -76.5 | -30.0 |
| Minimum, Maximum | -100.0 to 100.0 | -100.0 to 75.0 | -100.0 to 300.0 | -100.0 to 188.9 | -100.0 to 90.0 | -100.0 to 91.7 |
| P value vs Placebo | <.001** | <.001** | -- | <.001** | <.001** | -- |
| P value vs 2.5% Imiquimod Cream | 0.336 | -- | -- | 0.060 | -- | -- |

FIG. 7

Visit and Procedures Schedule

| | Screening | Baseline | Topical Treatment | | | | PDT | End of Study |
|---|---|---|---|---|---|---|---|---|
| Day | -14 to 0 | 0 | 14[a] (+1-3) | 28 (+/-2) | 42[a] (+1-3) | | 70 (+/-2) | 126 (+/-7) |
| Visit | 1 | 2[b] | Phone | 3 | Phone | | 4 | 5 |
| | | Baseline | End Cycle 1 | End 2-wk No-treatment | End Cycle 2 | | 4 weeks post end of topical | 8 weeks post PDT |
| Written informed consent, HIPAA authorization & photo release | X | | | | | | | |
| Inclusion and exclusion criteria | X | X | | | | | | |
| Relevant medical history | X | X[c] | | | | | | |
| Demographics | X | | | | | | | |
| Vital signs measurements including height and weight | X | | | | | | | |
| Pregnancy test (urine)[d] | X[d] | X | | | | | | |
| Investigator cosmetic assessment | | X | | | | | X[d] | X[c] |
| Patient cosmetic assessment | | X | | | | | X[c] | X |
| Baseline AK lesion mapping | | X | | | | | X[c] | |
| AK lesion counts | X | X | | | | | X[c] | X[f] |
| Adverse event query | | | X | X | X | | X[c] | X |
| Concomitant medication query | X | X | X | X | X | | X[c] | X |
| Clinical photography | | X | | X | | | X[c] | X |
| Telephone contact | | | X | | X | | | |
| Dispense topical study drug/diary | | X | | | | | | |
| Collect diary and unused drug | | | | X | | | X | |
| Randomize to PDT or observation | | | | X | | | X | |
| PDT (for those assigned to PDT) | | | | | | | X | |

[a] 1-3 days after scheduled last dose of study cream  [b] May be combined with screening visit  [c] Interval events should be added to medical history
[d] In woman of child-bearing potential only  [e] Prior to PDT  [f] Evaluator should be unaware of assignment to PDT or observatio

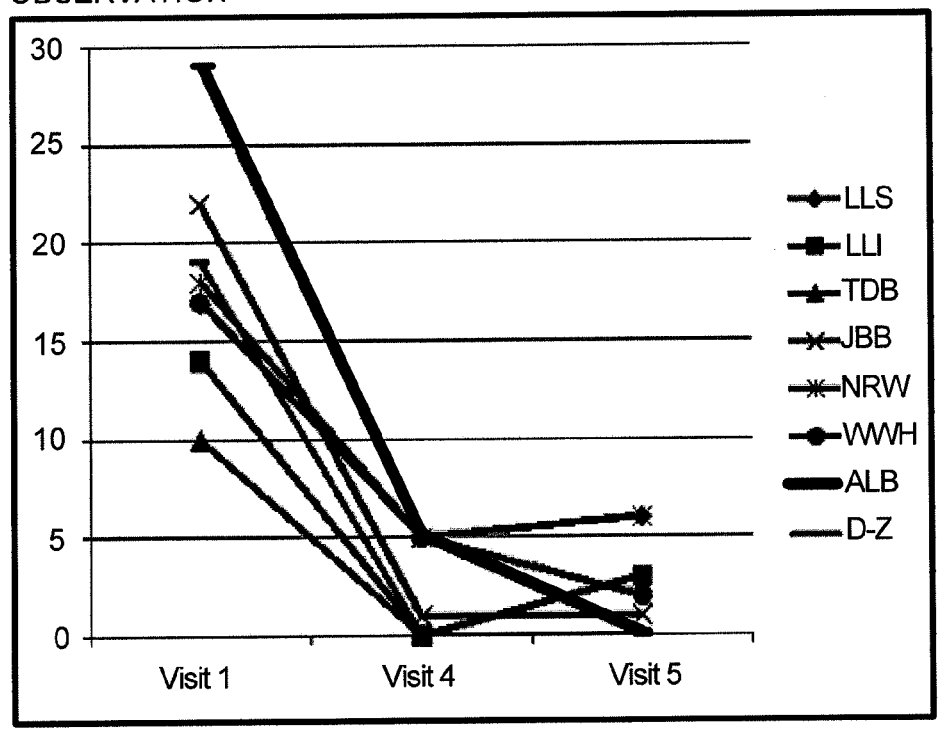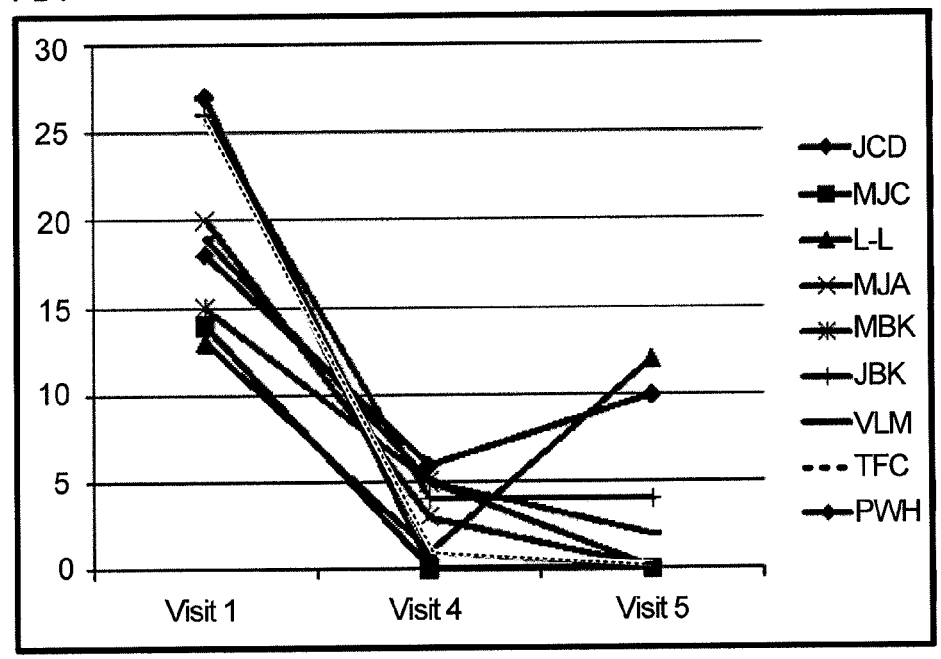
FIG. 8

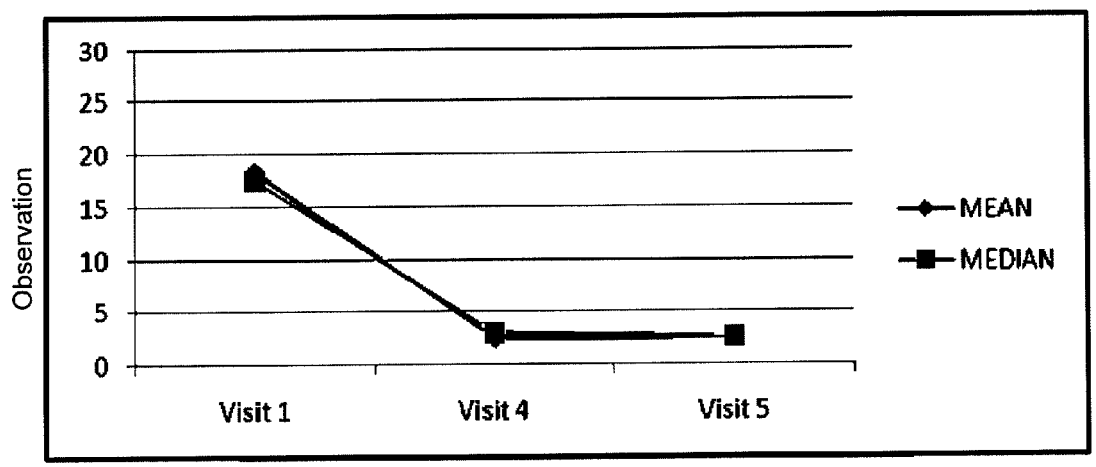
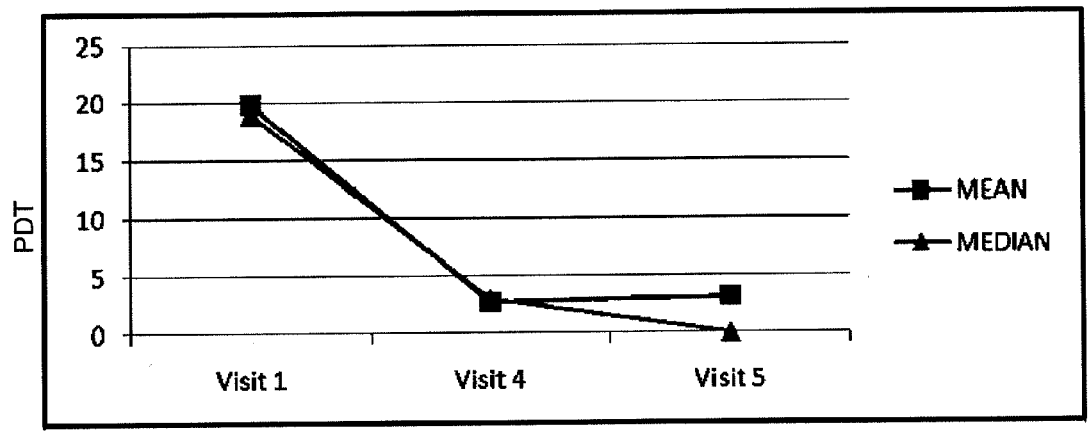
FIG. 9

COMBINATION THERAPY WITH LOW DOSAGE STRENGTH IMIQUIMOD AND PHOTODYNAMIC THERAPY TO TREAT ACTINIC KERATOSIS

CROSS-REFERENCES TO RELATED APPLICATIONS

This application claims priority to and the benefit of U.S. Provisional Application No. 61/534,876, filed Sep. 14, 2011, and entitled "Combination Therapy with Low Dosage Strength Imiquimod and Photodynamic Therapy to Treat Actinic Keratosis"; and to U.S. Provisional Application No. 61/535,276, filed Sep. 15, 2011, and entitled "Combination Therapy with Low Dosage Strength Imiquimod and Photodynamic Therapy to Treat Actinic Keratosis," the entire disclosures of which are herein incorporated by reference.

FIELD OF THE INVENTION

This disclosure is directed to the use of complementary or combination photodynamic therapy and topical therapy with 1-isobutyl-1H-imidazo[4,5-c]-quinolin-4-amine, also known as 1-(2-methylpropyl)-1H-imidazo[4,5-c]quinolin-4-amine or imiquimod. More specifically, this disclosure is directed to low dosage strength imiquimod topical therapy with short durations, in combination with photodynamic therapy to treat actinic keratosis ("AK"). In carrying out this disclosure, the photodynamic therapy and imiquimod topical therapy are generally sequentially applied, but may also be applied concomitantly. While the imiquimod topical therapy is generally administered first followed by the photodynamic therapy, with a non-treatment period in between in some embodiments, the complementary, combination, or follow-on therapies may be practiced in any sequential order, with or without a non-treatment period in between, or even concomitantly, in accordance with this disclosure.

BACKGROUND OF THE INVENTION

Actinic keratosis (AK) is a precancerous (premalignant) skin disorder caused by or associated with chronic exposure to radiant energy, such as sunlight. Actinic keratosis lesions are small, red, rough spots or lesions occurring on sun exposed areas of the skin. Actinic keratosis lesions possess many of the same cellular changes observed in a skin cancer called squamous cell carcinoma (SCC). Research shows that a mutated version of the p53 gene is found in sun-damaged cells in the body and is present in more than about 90% of people who have AK and squamous cell carcinomas. Although most actinic keratosis lesions do not actually become cancerous, some lesions can become malignant.

It is believed that actinic keratosis develops in skin cells called keratinocytes, which are the cells that constitute about 90% of the epidermis, the outermost layer of skin. Chronic sun exposure, over time, generates mutations in these cells and causes the cells to change in size, shape, the way they are organized, and the way they behave. In addition, the cellular damage can even extend to the dermis, the layer of skin beneath the epidermis.

Actinic keratoses (AKs) are common cutaneous lesions associated with chronic exposure to solar ultraviolet radiation (UVR). Frost C A and Green A C, *Br J Dermatol* 1994; 131:455-64. AKs and squamous cell carcinomas (SCCs) share histologic and molecular features; therefore, AKs are considered by some experts to be incipient SCCs. Cockerell C J, *J Am Acad Dermatol* 2000; 42(1Pt2):11-17. Although some AKs spontaneously regress and the risk of progression of an individual AK to an invasive SCC is low, AKs tend to be multifocal and recurrent. Since patients who present with multiple AKs may be at higher risk for developing an SCC, treatment of AKs is recommended. Glogau R G, *J Am Acad Dermatol* 2000; 42 (1Pt2):23-24; Criscione V D et al., *Cancer* 2009; 115:2523-30; Drake L A et al., *J Am Acad Dermatol* 1995; 32:95-98.

Actinic keratosis lesions generally measure in size between about 2 to about 6 millimeters in diameter. AK lesions can range in color from skin-toned to reddish and often have a white scale on top. On occasion, AK lesions will form into the shape of animal horns. When this occurs, the AKs are known as "cutaneous horns."

People who are at higher risk for developing actinic keratosis tend to be fair-skinned and spend significant time outdoors, e.g., at work or at play, over the course of many years. AK lesions usually develop on those areas of the body that have been constantly exposed to the sun for years. Additionally, the skin often becomes wrinkled, mottled, and discolored from chronic sun exposure. Common locations for actinic keratosis include the face, ears, lips, balding scalp, back of the neck, upper chest, the tops of the hands and forearms. When AK lesions develop on the lips, the condition is known as actinic cheilitis. Actinic cheilitis can be characterized by a diffuse scaling on the lower lip that cracks and dries. In some cases, the lips will have a whitish discoloration on the thickened lip.

Actinic keratosis is generally more common after age 40, because actinic keratosis takes years to develop. However, even younger adults may develop actinic keratosis when living in geographic areas that are exposed to high-intensity sunlight year round, such as Florida and Southern California.

Actinic keratosis has become a significant health care issue in the United States of America. It is estimated that over 20 million Americans suffer from actinic keratosis, and that that number continues to grow. In fact, actinic keratosis is so common today that treatment for actinic keratosis ranks as one of the most frequent reasons people consult a dermatologist.

AK treatments can be divided into lesion-directed versus field-directed, and provider-administered and patient-administered treatments. In the United States, cryosurgery is the most common provider-administered treatment and is a lesion-directed therapy. Balkrishnan R et al., *J Dermatolog Treat* 2006; 17:162-66. Cryosurgery utilizes extreme cold to destroy tissue, including abnormal or diseased tissue, such as benign or malignant skin disorders (e.g., keratoses, warts, moles, skin tags, neuromas, and small skin cancers). While cryosurgery is appropriate for localized conditions, there is the possibility of damage to healthy tissues, including nerve tissues and blood vessels supporting healthy tissues. Side effects of cryosurgery include localized pain, redness or other discoloration, blisters, scabbing, and/or peeling.

One advantage of cryosurgery is the ability to tailor the treatment based on individual lesion characteristics, such as the degree of hypertrophy or hyperkeratosis. Efficacy, however, may vary depending on the length of freezing; in one study, individual lesion clearance rates varied from 39% with freeze times of less than 5 seconds to 83% with freeze times of greater than 20 seconds. That K E et al., *Int J Dermatol* 2004; 43:687-92. The trade-off for long freeze times, however, is an increased risk for hypopigmentation and greater discomfort during the procedure, particularly when many lesions are treated in a single session. As a lesion-directed therapy, cryosurgery fails to address the issue of "field cancerization" associated with UVR damage. Braakhuis B J et al., *Cancer Res* 2003; 63:1727-30. The skin around clinically apparent AKs is subject to the same UVR-induced damage as found in AKs, resulting in dysplastic lesions that are not clinically apparent, but which have been identified by biopsy or specialized imaging. Ulrich M et al., *Dermatology* 2010; 220:15-24; Ortonne J P et al., *Exp Dermatol.* 2010; 19:641-47. Over time, these "subclinical" lesions may progress to clinically apparent "new" AKs requiring further treatment, or even develop into de novo invasive SCCs. Krawtchenko et al. reported an initial complete clearance rate of about 68% with cryosurgery, but at 1 year of follow-up, only 4% of treated patients had sustained clearance of the treatment field.

Cryosurgery has an additional drawback. In addition to being ineffective against subclinical AK lesions, it is a painful procedure that is generally too painful or costly to treat all clinical or visible AK lesions in a single procedure. Thus, practitioners generally must choose at the time of treatment as to which AK lesions will be cryosurgically removed. Consequently, it is often that several clinical AK lesions go untreated requiring further cryosurgery sessions at some point in the future depending upon provider restrictions and patient tolerance. It is also often the case that because cryosurgery can be a very painful procedure, many patients fail to follow-up with treatment of the remaining clinical and subclinical AK lesions.

Field-directed treatments such as imiquimod, diclofenac and 5-fluoruracil treat both individual AKs as well as a field of cancerization. Imiquimod is a Toll-like receptor 7 agonist that has been shown to be safe and effective for the treatment of AKs. Gaspari A et al., *J Drugs Dermatol* 2009; 8:467-74; Lebwohl M et al., *J Am Acad Dermatol* 2004; 50:714-21; Swanson N et al., *J Am Acad Dermatol* 2010; 62:582-90; Hanke C W et al., *J Am Acad Dermatol* 2010; 62:573-81. In addition, imiquimod treatment appears to treat subclinical lesions, contributing to a high rate of sustained complete clearance of the treatment field. Krawtchenko N et al, *Br J Dermatol* 2007; 157(Suppl 2):34-40.

Imiquimod has a molecular formula of $C_{14}H_{16}N_4$ and a molecular weight of 240.3. The chemical structural formula for imiquimod is as follows:

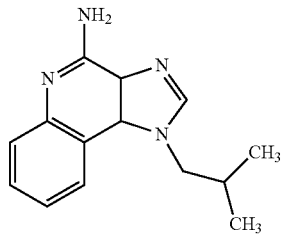 [SMILES: CC(C)CN1C=NC2C(N)=Nc3ccccc3C21]

Imiquimod, also known as 1-isobutyl-1H-imidazo[4,5-c]-quinolin-4-amine and also known as (aka) 1-(2-methylpropyl)-1H-imidazo[4,5-c]quinolin-4-amine, is commercially available, e.g., as ALDARA 5% imiquimod cream, as now approved by the U.S. Food & Drug Administration ("FDA"). In addition, ZYCLARA® is a lower dosage 2% or 3.75% imiquimod cream. ZYCLARA® can be used to treat actinic keratosis with shorter durations of therapy, than currently prescribed for the commercially available ALDARA 5% imiquimod cream. Such lower dosage strength imiquimod formulations can be used to deliver an efficacious dose of imiquimod for treating actinic keratosis with an acceptable safety profile.

Imiquimod is disclosed in U.S. Pat. No. 4,689,338, among other things, and described therein as an antiviral agent and as an interferon inducer, which is incorporated herein by reference in its entirety. A variety of formulations for topical administration of imiquimod are also described therein. This U.S. Pat. No. 4,689,338 is incorporated herein by reference in its entirety.

U.S. Pat. No. 4,411,893 discloses, among other things, the use of N,N-dimethyldodecylamine-N-oxide as a skin penetration enhancer in aqueous systems, wherein this U.S. patent is incorporated herein by reference in its entirety.

U.S. Pat. No. 4,722,941 discloses, among other things, readily absorbable pharmaceutical compositions that comprise a pharmacologically active agent distributed in a vehicle comprising an absorption-enhancing amount of at least one fatty acid containing 6 to 12 carbon atoms and optionally a fatty acid monoglyceride. Such compositions are said to be particularly useful for increasing the absorption of pharmacologically active bases, wherein this U.S. patent is incorporated herein by reference in its entirety.

U.S. Pat. No. 5,238,944, U.S. Pat. No. 7,038,051, U.S. Pat. No. 6,693,113, U.S. Pat. No. 6,894,060, U.S. Patent Publication No. 2011/0021555 (U.S. Ser. No. 12/636,613), U.S. Patent Publication No. 2007/0123558, U.S. Patent Publication No. 2004/087614, and U.S. Patent Publication No. 2002/147210 disclose, among other things, topical formulations and/or topical delivery systems containing 1-isobutyl-1H-imidazo[4,5-c]-quinolin-4-amine or 1-(2-methylpropyl)-1H-imidazo[4,5-c]quinolin-4-amine, wherein each are incorporated herein by reference in their entireties.

Currently, the FDA has approved a 5% imiquimod cream, commercially available under the brand name ALDARA®, to treat certain dermal and mucosal associated conditions, such as (1) the topical treatment of clinically typical, non-hyperkeratotic actinic keratosis (AK) on the face or scalp in immunocompetent adults, (2) topical treatment of biopsy-confirmed, primary superficial basal cell carcinoma (sBCC) in immunocompetent adults, and (3) the topical treatment of external genital and perianal warts/condyloma acuminate in patients 12 years or older. Each gram of the ALDARA 5% imiquimod cream contains 50 mg of imiquimod in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben. The ALDARA 5% imiquimod cream is packaged in single-use packets or sachets, each containing 250 mg of cream, equivalent to 12.5 mg of imiquimod.

Notwithstanding FDA approval, ALDARA 5% imiquimod cream treatment is not without limitation, including an unsimplified and lengthy dosing regimen. Generally speaking, the treatment regimen for actinic keratosis using FDA-approved ALDARA 5% imiquimod cream consists of applying the ALDARA 5% imiquimod cream two times per week for a full 16 weeks to a defined/limited treatment area on the face or scalp (but not both concurrently). The surface treatment area for ALDARA 5% imiquimod cream is limited to approximately 25 $cm^2$ (e.g., a 5 cm×5 cm area, which may be of any shape; the treatment area does not have to be square) and is defined as one contiguous area. The number of AK lesions treated with ALDARA 5% imiquimod cream per treatment area is generally between about 4 and about 8. Because the treatment area is quite small, less than one single-use ALDARA packet or sachet (250 mg of total cream, of which 12.5 mg is imiquimod) is generally used per application. Inconsistencies in both compliance and therapeutic results frequently occur with the treatment of actinic keratosis with FDA-approved ALDARA 5% imiquimod cream due to the lengthy treatment period, i.e., 16 weeks, the complicated dosing regimen, i.e., twice weekly, and the high incidence of application site reactions.

An optimized 2.5% or 3.75% imiquimod cream formulation (ZYCLARA®, Graceway Pharmaceuticals, LLC, Bristol, Tenn.) has demonstrated efficacy and tolerability in treating large areas of AK-involved skin (full face or balding scalp), in a short regimen of two 2-week cycles of daily applications. Swanson N et al., *J Am Acad Dermatol* 2010; 62:582-90. As shown in U.S. Patent Publication No. 2011/0021555 (U.S. Ser. No. 12/636,613), use of ZYCLARA® 3.75% imiquimod cream, or use of 2.5% imiquimod cream, has been shown to overcome certain of the limitations associated with the treatment of actinic keratosis with FDA-approved ALDARA 5% imiquimod cream and addresses current medical needs for (1) a larger treatment area (full face or balding scalp: >25 cm$^2$ vs. up to 25 cm$^2$ for ALDARA 5% imiquimod cream), (2) a shorter treatment period, e.g., two 2-week or two 3-week treatment cycles with an interim 2-week or 3-week no-treatment period sandwiched between them, respectively, vs. the full 16-week treatment regimen for ALDARA 5% imiquimod cream), (3) a more intuitive dosing regimen (daily dosing vs. twice weekly dosing for ALDARA 5% imiquimod cream) and (4) less or a lower incidence of application site reactions. The disclosure of U.S. Patent Publication No. 2011/0021555 (U.S. Ser. No. 12/636,613) is incorporated by reference herein in its entirety as though set forth explicitly herein.

Photodynamic therapy (PDT) with aminolevulinic acid (ALA) 20% topical solution is approved as a lesion-directed treatment of minimally to moderately thick AKs using one or two treatment sessions. Piacquadio et al., *Arch Dermatol.* 2004; 140:41-6; see also Levulan® Kerastick prescribing information. ALA absorbed by AK cells is converted to protoporphyrin IX, a photosensitizer. Excitation of the porphyrin molecule with light results in generation of singlet oxygen that leads to formation of superoxide and hydroxyl radicals which induce necrosis and apoptosis of the targeted cells. Gold & Goldman, *Dermatol Surg.* 2004; 30:1077-83. Although approved as a lesion-directed therapy with overnight incubation, field-directed PDT with ALA using short incubation also appears to provide meaningful efficacy. Touma et al., *Arch Dermatol.* 2004; 140:33-40.

PDT with ALA followed by imiquimod 5% treatment appeared to result in a higher sustained rate in AK reduction during follow-up than with PDT alone. Shaffelburg, *J Drugs Dermatol.* 2009; 8:35-9. Sequential therapy with PDT with methyl aminolevulinate, another photosensitizer, followed by imiquimod 5% treatment has been reported for basal cell carcinoma (*Devirgiliis Dermatol Online J* 2008; 28; 14:25, Maden et al., *J Plast Reconstr Aesthet Surg.* 2009; 62:e368-72) and Bowen's disease (Vereecken et al., *J Eur Acad Dermatol Venereal.* 2006; 20:1397-9). Sequential treatment with imiquimod 5% followed by PDT with methyl aminolevulinate has also been reported in the treatment of vulvar intraepithelial neoplasia. Winters et al., *Clin Cancer Res.* 2008; 14:5292-9. There are, however, no publications in PubMed with respect to the safety and/or efficacy of using topical 5%, 3.75%, or 2.5% imiquimod prior to lesion or field-directed PDT in treating AKs.

Thus, notwithstanding the advancements in the treatment of actinic keratosis, there still remains a need for improved treatments for treating both clinical and subclinical AK lesions.

BRIEF SUMMARY OF THE INVENTION

This disclosure relates to methods of treating actinic keratosis (AK) in a subject in need thereof. In some embodiments, the method comprises: topically applying to a treatment area on the subject a composition comprising a lower dosage strength formulation of imiquimod; and administering photodynamic therapy to the treatment area or to an AK lesion in the treatment area; thereby treating AK in the subject.

In some embodiments, applying a composition comprising imiquimod to the treatment area comprises a first treatment period and a second treatment period, wherein the first and second treatment periods are separated by a non-treatment period.

In some embodiments, each of the first and second treatment periods is a two-week treatment period. In some embodiments, the first and second treatment periods are separated by a two-week non-treatment period.

In some embodiments, each of the first and second treatment periods is a three-week treatment period. In some embodiments, the first and second treatment periods are separated by a three-week non-treatment period.

In some embodiments, the composition comprising the lower dosage strength imiquimod formulation comprises imiquimod in an amount from about 1% (w/w) to about 4.25% (w/w). In some embodiments, the composition comprises imiquimod in an amount of about 2.5% (w/w). In some embodiments, the composition comprises imiquimod in an amount of about 3.75% (w/w).

In some embodiments, the composition comprising imiquimod further comprises a pharmaceutically acceptable vehicle. In some embodiments, the pharmaceutically acceptable vehicle comprises a fatty acid. In some embodiments, the fatty acid is selected from the group consisting of stearic acid, palmitic acid, unrefined oleic acid, linoleic acid, isostearic acid, refined oleic acid, and super refined oleic acid.

In some embodiments, the composition comprises an imiquimod formulation that is selected from the group of 2.5% or 3.75% imiquimod formulations listed in Table 10.

In some embodiments, the composition comprising imiquimod is a cream. In some embodiments, the composition comprising imiquimod is a pressure-sensitive adhesive composition. In some embodiments, the pressure-sensitive adhesive composition is a patch.

In some embodiments, the composition comprising imiquimod is applied as a field-directed treatment. In some embodiments, the composition comprising imiquimod is applied as a lesion-directed treatment.

In some embodiments, the composition comprising imiquimod is administered once daily.

In some embodiments, the photodynamic therapy comprises: administering a topical formulation comprising a photoreactive compound to the treatment area or to an AK lesion in the treatment area; and irradiating the treatment area of the subject with a light having a wavelength corresponding to the characteristic light absorption wavelength of the photoreactive compound. In some embodiments, the photoreactive compound is aminolevulinic acid (ALA).

In some embodiments, the photodynamic therapy is field-directed. In some embodiments, the photodynamic therapy is lesion-directed.

In some embodiments, the treatment area is the full or entire face, scalp, ears, neck, back of the neck, torso, chest, upper chest, back, stomach, arms, forearms, hands or the tops of the hands, legs, feet, and/or lips. In some embodiments, the treatment area is the face or scalp. In some embodiments, the treatment area is the full face. In some embodiments, the treatment area is the entire balding scalp.

In some embodiments, the AK lesion is a clinically visible or palpable lesion. In some embodiments, the AK lesion is a hypertrophic lesion. In some embodiments, the AK lesion is a non-hypertrophic lesion. In some embodiments, the AK lesion is a non-palpable lesion. In some embodiments, the AK lesion is a sub-clinical lesion.

In some embodiments, the photodynamic therapy treatment is administered after the completion of the imiquimod treatment. In some embodiments, the photodynamic therapy treatment is administered within about 14 days after the completion of the imiquimod treatment.

In some embodiments, the photodynamic therapy treatment is administered prior to the commencement of the imiquimod treatment. In some embodiments, the photodynamic therapy treatment is administered within about 14 days prior to the commencement of the imiquimod treatment.

In some embodiments, the photodynamic therapy is administered concomitantly with the imiquimod treatment.

In some embodiments, the subject is a human adult. In some embodiments, the subject is an immunocompetent human adult.

In some embodiments, the method results in the clearance of at least 75% of the baseline AK in the subject. In some embodiments, the method results in the clearance of at least 75% of baseline and new AK in the subject. In some embodiments, the method results in the complete clearance of the baseline AK in the subject. In some embodiments, the method results in the complete clearance of baseline and new AK in the subject.

In some embodiments, the method of treating AK in the subject comprises: topically applying to a treatment area on the subject a composition comprising imiquimod in an amount of about 2.5% (w/w) or about 3.75% (w/w) over a first two-week treatment period; topically applying to the treatment area on the subject the composition comprising imiquimod over a second two-week treatment period, wherein the first two-week treatment period and the second two-week treatment period are separated by a two-week non-treatment period; and administering photodynamic therapy to the treatment area or to an AK lesion in the treatment area; thereby treating AK in the subject.

This disclosure also relates to methods of treating actinic keratosis (AK) in a subject in need thereof, wherein the method comprises: a step for administering a lower dosage strength imiquimod formulation to a treatment area in the subject; and a step for administering photodynamic therapy to the treatment area. The step for administering a lower dosage strength imiquimod formulation to a treatment area in the subject, and the step for administering photodynamic therapy to the treatment area, can be performed according to embodiments of this disclosure.

This disclosure also relates to a combination of a composition comprising a lower dosage strength imiquimod formulation and photodynamic therapy for use in treating actinic keratosis (AK) in a subject in need thereof. In some embodiments, a composition comprising a lower dosage strength imiquimod formulation (e.g., comprising imiquimod in an amount of between about 1% (w/w) and about 4.25% (w/w), e.g., about 2.5% (w/w) or about 3.75% (w/w)) is as described herein. In some embodiments, photodynamic therapy (e.g., using the photoreactive compound aminolevulinic acid (ALA)) is as described herein.

DEFINITIONS

The following definitions are provided for specific terms which are used in the detailed description. Unless otherwise indicated, all numbers expressing quantities, ratios, and numerical properties of ingredients, reaction conditions, and so forth used in the specification and claims are to be understood as being modified in all instances by the term "about." All parts, percentages, ratios, etc., herein are by weight unless indicated otherwise.

As used herein, the singular forms "a" or "an" or "the" are used interchangeably and intended to include the plural forms as well and fall within each meaning, unless expressly stated otherwise. Also as used herein, "at least one" is intended to mean "one or more" of the listed element. Singular word forms are intended to include plural word forms and are likewise used herein interchangeably where appropriate and fall within each meaning, unless expressly stated otherwise. Except where noted otherwise, capitalized and non-capitalized forms of all terms fall within each meaning.

As used herein, the term "IMIQ" or "Imiq" refers to imiquimod, which is also known as 1-isobutyl-1H-imidazo[4,5-c]-quinolin-4-amine and also known as 1-(2-methylpropyl)-1H-imidazo-[4,5-c]-quinolin-4-amine.

The term "lower dosage strength(s)", as used herein, refers to a pharmaceutical formulation containing imiquimod in an amount of between about 1.0% and about 4.25% by weight based on the total weight of the formulation. In some embodiments, a lower dosage strength formulation comprises imiquimod in an amount of between about 2.5% and about 3.75% by weight based on the total weight of the formulation. In some embodiments, a lower dosage strength formulation comprises imiquimod in an amount of about 2.5% or about 3.75% by weight based on the total weight of the formulation. Examples of a suitable lower dosage strength imiquimod formulation are ZYCLARA® 3.75% imiquimod and ZYCLARA® 2.5% imiquimod; nevertheless, it should be understood that this disclosure is not limited to these examples.

The term "short duration(s) of therapy", as used herein, refers to the treatment regimen involving administering the imiquimod topical therapy and the photodynamic therapy, optionally with a brief non-treatment period in between, e.g., a non-treatment period of up to about 28 days, up to about 14 days, or between about 7 and 14 days. The complementary therapies may be practiced in any sequential order (e.g., photodynamic therapy followed by imiquimod topical therapy, or imiquimod topical therapy followed by photodynamic therapy), with or without a non-treatment period in between, or even concomitantly, in accordance with this disclosure. It should be understood by those versed in this art that the cycle of the treatment regimen comprises administering an imiquimod topical therapy for any period disclosed herein sequentially or concomitantly with photodynamic therapy, with an optional non-treatment period in between for any period disclosed herein.

In some embodiments, the term "short duration(s) of therapy" refers to the duration of the imiquimod topical therapy. The daily topical application of an effective amount of imiquimod may be administered to a defined treatment area diagnosed with AK lesions for a total "on-treatment period" of up to about 6 weeks, depending upon which lower dosage strength imiquimod formulation of this disclosure is selected for daily application, or for a total on-treatment period of up to about 2 or 4 weeks, wherein an optional defined intervening non-treatment of up to about 3 weeks, or of up to about 2 weeks, may be taken at some point during the course of treatment, to treat actinic keratosis. Thereby, the short durations of imiquimod topical therapy may include, for example, a total duration of 9 weeks (3 weeks on, 3 weeks off, 3 weeks on), or a total duration of 6 weeks (2 weeks on, 2 weeks off, 2 weeks on) from beginning of dosing to the end of dosing, inclusive of the non-treatment period. In some embodiments, the short duration of imiquimod topical therapy consists of 2-cycle treatment regimens with a non-treatment period between the treatment cycles. In addition, in some embodiments, the short duration of imiquimod topical therapy may also include an 8 week examination period (no further treatment) following the treatment period.

As used herein, the term "2×2×2" refers to imiquimod topical therapy having a two-week, 2-cycle AK treatment regimen, wherein (1) during the first 2 weeks (the first cycle of treatment), a lower dosage strength imiquimod formulation of this disclosure is applied once daily each day to an AK treatment area, (2) during the second 2 weeks, there is a non-treatment period in which no treatment occurs (i.e., a prescribed period in which no imiquimod is applied), and (3) during the third 2 weeks (the second cycle of treatment), the same lower dosage strength imiquimod formulation is again applied once daily each day to the same AK treatment area.

As used herein, the term "3×3×3" refers to imiquimod topical therapy having a three-week, 2-cycle AK treatment regimen, wherein (1) during the first 3 weeks (the first cycle of treatment), a lower dosage strength imiquimod formulation of this disclosure is applied once daily each day to an AK treatment area, (2) during the second 3 weeks, there is a non-treatment period in which no treatment occurs (i.e., a prescribed period in which no imiquimod is applied), and (3) during the third 3 weeks (the second cycle of treatment), the same lower dosage strength imiquimod formulation is again applied once daily each day to the same AK treatment area.

As used herein, the term "bioequivalence" or "bioequivalent" refers to lower dosage strength formulations which are pharmaceutically equivalent and in which their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which imiquimod becomes available from such formulations at the site of imiquimod action when administered at the same molar dose under similar conditions, e.g., the rate at which imiquimod can leave such a formulation and the rate at which imiquimod can either cross the stratum corneum and/or become available at the site of action to treat actinic keratosis.

As used herein, the term "complete clearance" or "total clearance" refers to the absence of AK lesions in the treatment area as compared with a baseline (e.g., the amount of AK lesions in the treatment area of the subject prior to the onset of treatment). As used herein, the phrase "rate of complete clearance" refers to the rate of complete clearance of AK lesions in the treatment area. In some embodiments, the AK lesion(s) in the treatment area is a clinically visible or palpable lesion, a hypertrophic lesion, a non-hypertrophic lesion, a non-palpable lesion, or any combination thereof.

As used herein, the term "partial clearance" refers to a reduction in AK lesions in the treatment area as compared with a baseline (e.g., the amount of AK lesions in the treatment area of the subject prior to the onset of treatment). As used herein, the phrase "rate of partial clearance" refers to the rate of partial clearance of AK lesions in the treatment area. In some embodiments, the AK lesion(s) in the treatment area is a clinically visible or palpable lesion, a hypertrophic lesion, a non-hypertrophic lesion, a non-palpable lesion, or any combination thereof. In some embodiments, there is partial clearance of AK lesions in the treatment area when the amount of AK lesions in the treatment area is reduced by at least about 25%, at least about 30%, at least about 40%, at least about 50%, at least about 60%, at least about 70%, at least about 75%, at least about 80%, or more as compared to the baseline.

As used herein, the term "bioavailability" or "bioavailable" refers generally to the rate and extent of absorption of imiquimod into the systemic circulation and, more specifically, the rate or measurements intended to reflect the rate and extent to which imiquimod becomes available at the site of action or is absorbed from a drug product and becomes available at the site of action. In other words, and by way of example, the extent and rate of imiquimod absorption from a lower dosage strength formulation of this disclosure as reflected by a time-concentration curve of imiquimod in systemic circulation.

As used herein, the term "pharmaceutical equivalence" or "pharmaceutically equivalent" refers to lower dosage strength imiquimod formulations of this disclosure that contain the same amount of imiquimod, in the same dosage forms, but not necessarily containing the same inactive ingredients, for the same route of administration and meeting the same or comparable compendial or other applicable standards of identity, strength, quality, and purity, including potency and, where applicable, content uniformity and/or stability.

As used herein, the term "therapeutic equivalence" or "therapeutically equivalent" refers to those lower dosage strength imiquimod formulations that (a) will produce the same clinical effect and safety profile when practicing the short durations of therapy to treat actinic keratosis in accordance with this disclosure and (b) are pharmaceutical equivalents, e.g., they contain imiquimod in the same dosage form, they have the same route of administration; and they have the same imiquimod strength. In other words, therapeutic equivalence means that a chemical equivalent of an imiquimod lower dosage strength imiquimod formulation of this disclosure (i.e., containing the same amount of imiquimod in the same dosage form) when administered to the same individuals in the same dosage regimen will provide essentially the same efficacy and toxicity.

As used herein, an "effective amount" is an amount sufficient to affect beneficial or desired results. An effective amount may be administered one or more times to achieve the beneficial or desired result.

As used herein, a "therapeutically effective amount" refers to an amount sufficient to prevent, correct and/or normalize an abnormal physiological response. In one aspect, a "therapeutically effective amount" is an amount sufficient to reduce, by at least about 10%, 20%, 30%, 40%, 50%, 60%, 70%, 80%, 90%, or more, a clinically significant feature of pathology, such as the size or palpability of a lesion.

The term "mammal" includes, but is not limited to, humans and non-human animals, e.g., primates, dogs, cats, pigs, sheep, cows, horses, mice, and rats.

BRIEF DESCRIPTION OF THE DRAWINGS

FIG. 1 shows a summary of primary and secondary efficacy endpoints in which (a) the results of the GW01-0702 and GW01-0704 (2×2×2) studies for each imiquimod formulation strength, i.e., about 2.5% (w/w) or about 3.75% (w/w), that are used in the studies are combined, respectively; (b) the results of the GW01-0703 and GW01-0705 (3×3×3) studies each imiquimod formulation strength, i.e., about 2.5% (w/w) or about 3.75% (w/w), that are used in the studies are combined, respectively; and (c) the analysis is within regimen ITT ("intent-to-treat") populations. In FIG. 1, complete clearance is defined as the absence of clinical visible or palpable AK lesions in the treatment area; partial clearance is defined as at least a 75% reduction in the number of AK lesions in the treatment area as compared with baseline. P values are from Cochran-Mantel-Haenszel test, stratified by analysis site, taking 2 treatment groups at a time. The P values marked with ** are statistically significant using Hochberg's modified Bonferroni procedure. LOCF=last observation that is carried forward. Confidence intervals are calculated using exact binomial statistics. As used in this figure, "2.5%" refers to a 2.5% imiquimod lower dosage strength formulation as described in Example 24, and "3.75%" refers to a 3.75% imiquimod lower dosage strength formulation as described in Example 24.

FIG. 2 is a summary of primary and secondary efficacy endpoints for a two-week treatment cycle regimen concerning ITT population for studies GW01-0702 and GW01-0704. In FIG. 2, complete clearance is defined as the absence of clinical visible or palpable AK lesions in the treatment area; partial clearance is defined as at least a 75% reduction in the number of AK lesions in the treatment area as compared with baseline. P values are from Cochran-Mantel-Haenszel test, stratified by analysis site, taking 2 treatment groups at a time. The P values marked with ** are statistically significant using Hochberg's modified Bonferroni procedure. LOCF=last observation that is carried forward. Confidence intervals are calculated using exact binomial statistics. As used in this figure, "2.5%" refers to a 2.5% imiquimod lower dosage strength formulation as described in Example 24, and "3.75%" refers to a 3.75% imiquimod lower dosage strength formulation as described in Example 24.

FIG. 7 outlines the visit and procedure schedule for the imiquimod topical therapy/photodynamic therapy studies described in Examples 25-32 and 34.

FIG. 8 shows results from a Phase IV trial for imiquimod topical therapy followed by photodynamic therapy. Efficacy is shown as lesion count over time, as tracked from baseline. "PDT" refers to the group of subjects receiving imiquimod topical therapy followed by photodynamic therapy, and "Observation" refers to the group of subjects receiving only imiquimod topical therapy.

FIG. 9 shows results from a Phase IV trial for imiquimod topical therapy followed by photodynamic therapy. Mean and median lesion count over time is shown for the observation group (top panel) and for the PDT group (bottom panel).

DETAILED DESCRIPTION

I. Introduction

Figure 3:
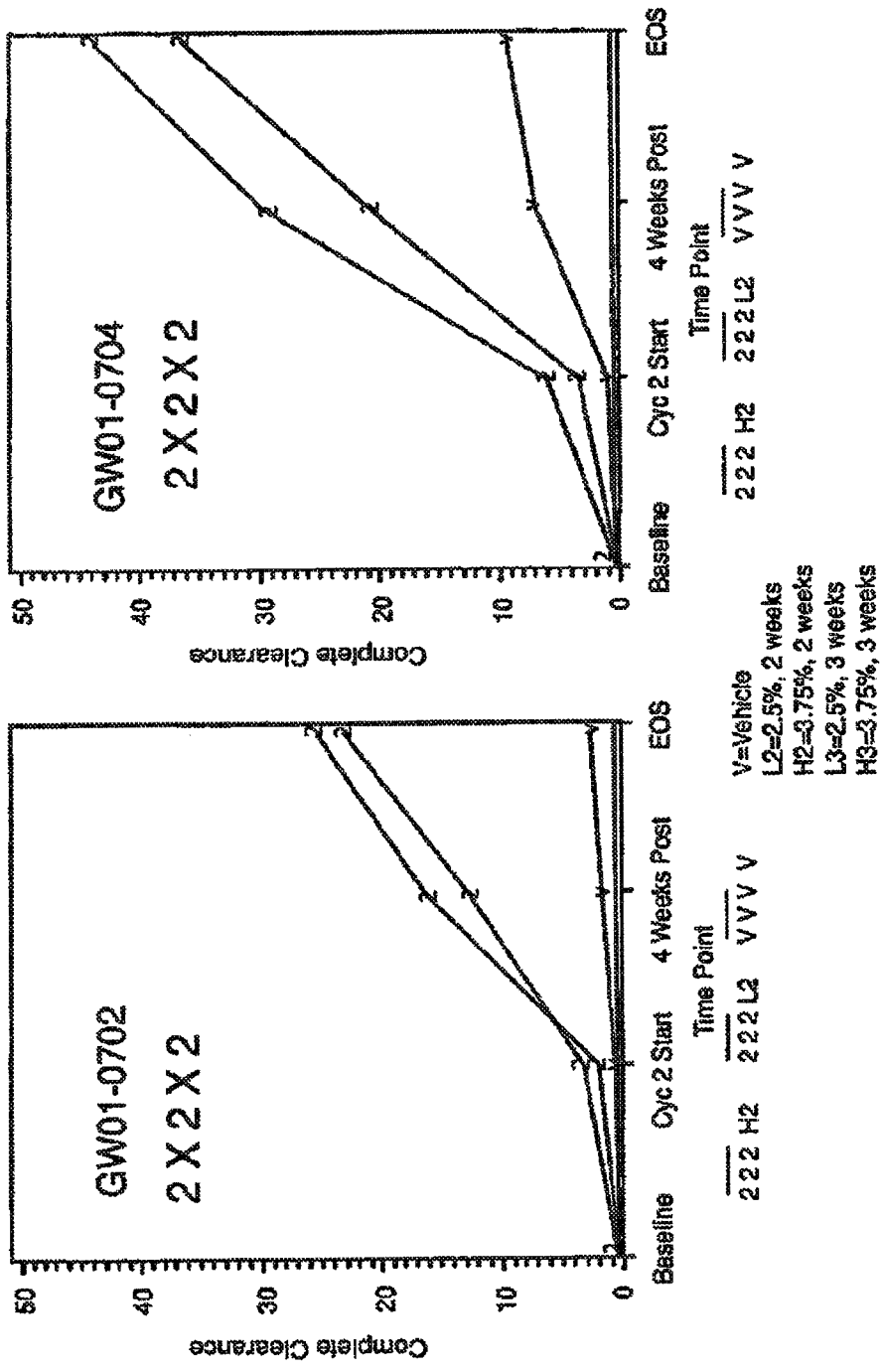
FIG. 3 shows efficacy measures of complete clearance, by time point, for studies GW01-0702 and GW01-0704 for the 2-cycle 2×2×2 (2 weeks) treatment regimen. As used in this figure, "Complete Clearance" refers to the rate of complete clearance of AK lesions, "Cyc 2 Start" refers to the start of the second cycle, "4 Weeks Post" refers to 4 weeks post-treatment, and "EOS" refers to End of Study.
Figure 4:
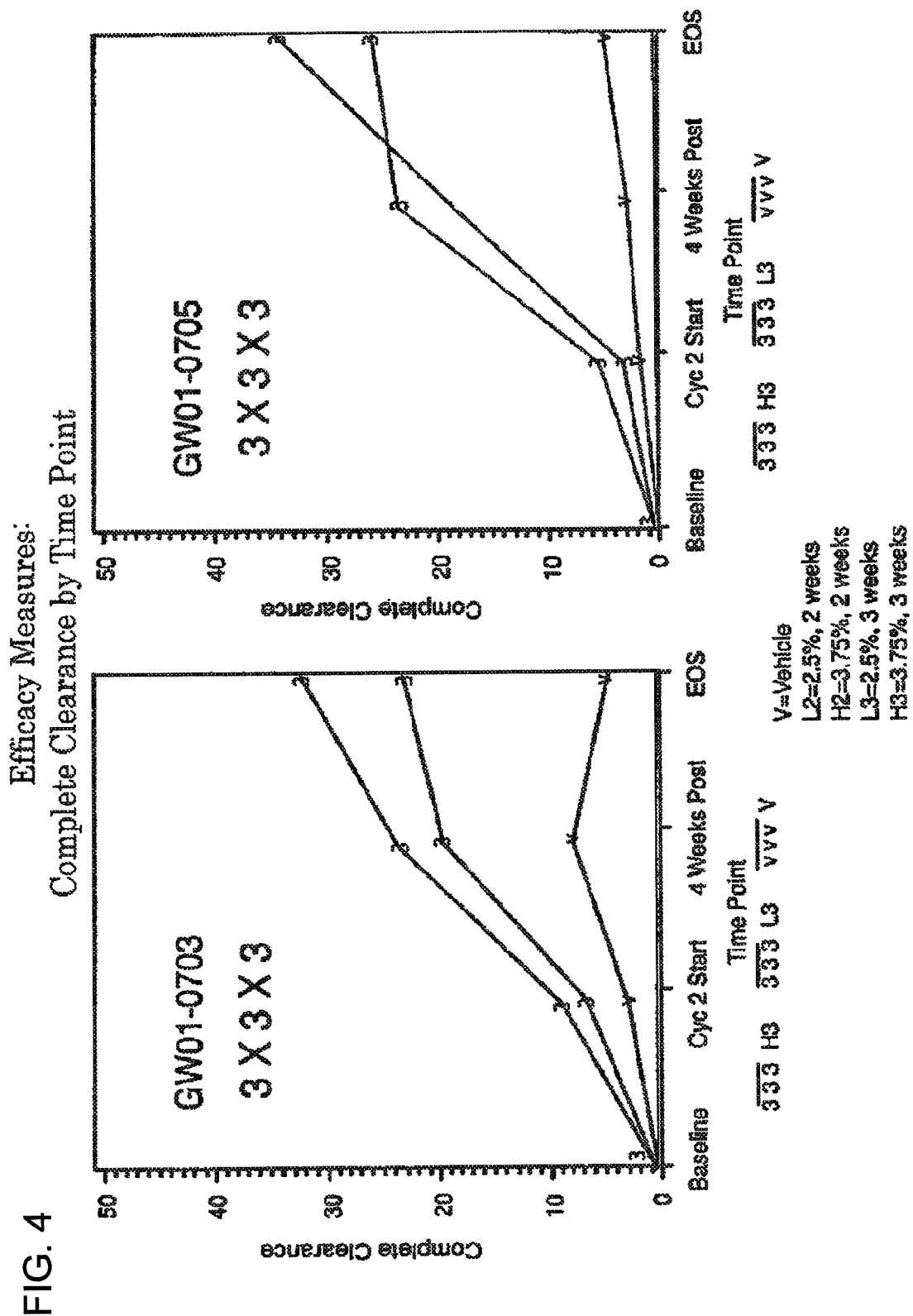
FIG. 4 shows efficacy measures of complete clearance, by time point, for studies GW01-0703 and GW01-0705 for the 2-cycle 3×3×3 (3 weeks) treatment regimen. As used in this figure, "Complete Clearance" refers to the rate of complete clearance of AK lesions, "Cyc 2 Start" refers to the start of the second cycle, "4 Weeks Post" refers to 4 weeks post-treatment, and "EOS" refers to End of Study.
Figure 5:
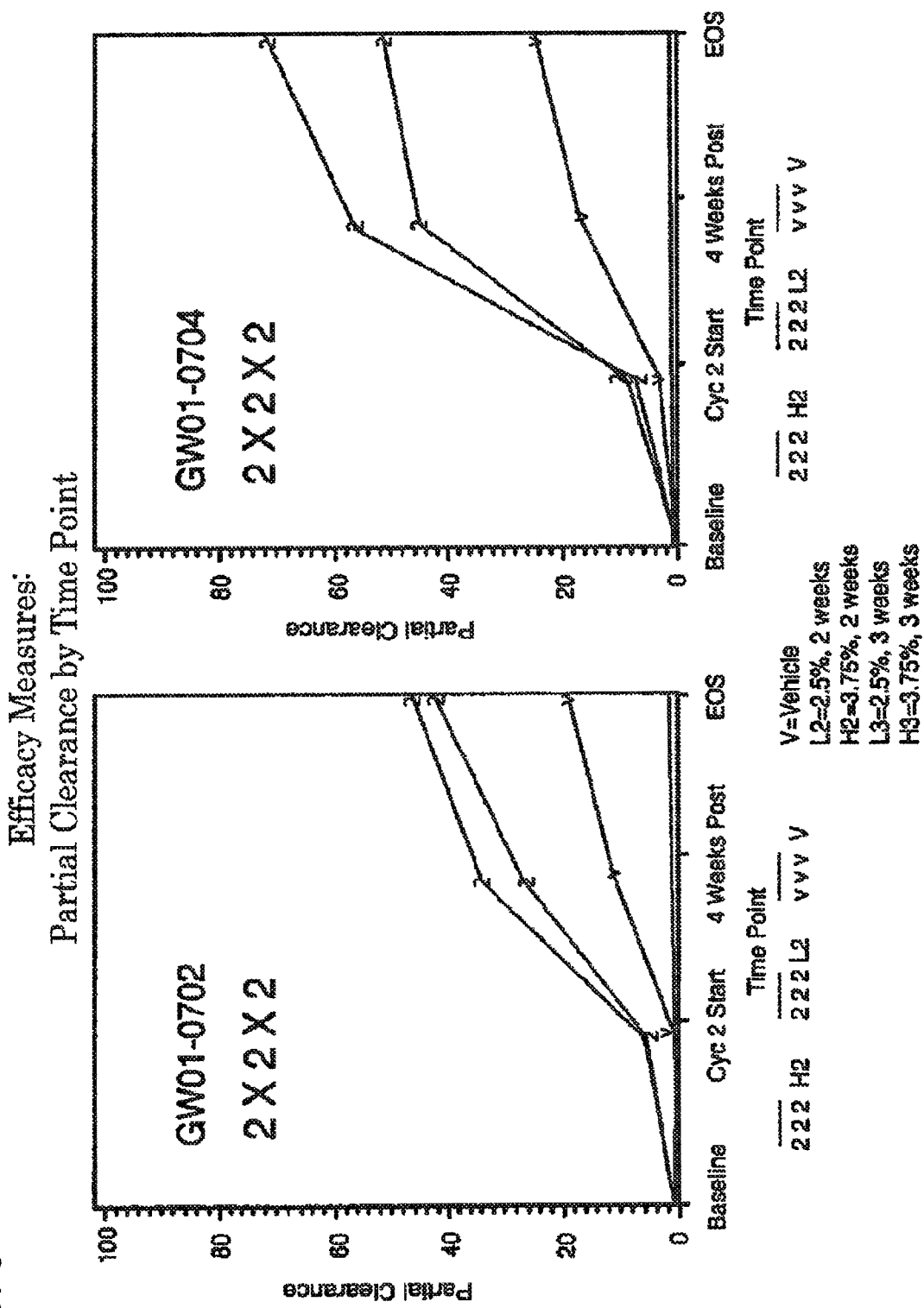
FIG. 5 shows efficacy measures of partial clearance, by time point, for studies GW01-0702 and GW01-0704. As used in this figure, "Partial Clearance" refers to partial clearance of AK lesions (defined in this study as at least about 75% reduction in the number of AK lesions in the treatment area as compared with baseline), "Cyc 2 Start" refers to the start of the second cycle, "4 Weeks Post" refers to 4 weeks post-treatment, "EOS" refers to End of Study, and "2×2×2" refers to a two week, 2-cycle treatment, as described in the specification.
Figure 6:
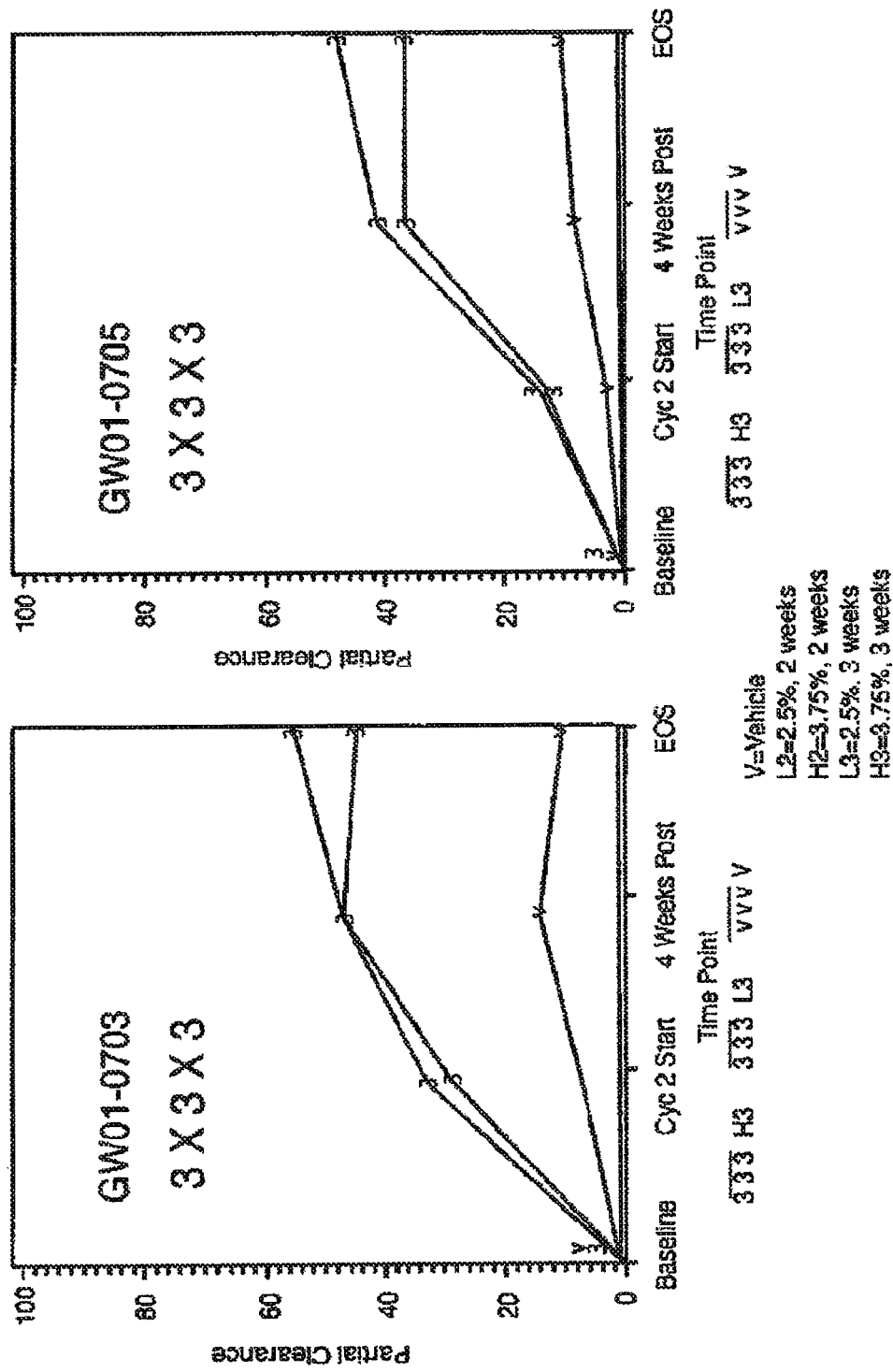
FIG. 6 shows efficacy measures of partial clearance, by time point, for studies GW01-0703 and GW01-0705. As used in this figure, "Partial Clearance" refers to partial clearance of AK lesions (defined in this study as at least about 75% reduction in the number of AK lesions in the treatment area as compared with baseline), "Cyc 2 Start" refers to the start of the second cycle, "4 Weeks Post" refers to 4 weeks post-treatment, "EOS" refers to End of Study, and "3×3×3" refers to a three week, 2-cycle treatment, as described in the specification.

This disclosure relates to the discovery of novel and improved AK treatment regimens comprising photodynamic therapy and imiquimod topical therapy, used in combination to complement one another to treat actinic keratosis. According to embodiments, the use of a combination of photodynamic therapy and imiquimod topical therapy is more effective in treating both clinical and subclinical AK lesions, as compared to the treatment of clinical and subclinical AK lesions with photodynamic therapy when photodynamic therapy is used alone, i.e., as mono therapy, or with imiquimod topical therapy when imiquimod topical therapy is used alone, i.e., as mono therapy.

The novel complementary or combination AK therapies contemplated by this disclosure: (1) significantly improve clearance of photodynamic therapy-treated AKs; (2) treat both clinical and subclinical AK lesions; (3) treat those visible AK lesions in excess of what photodynamic therapy can actually treat due to, e.g., patient tolerance, provider treatment limits and/or photodynamic therapy cost to the patient; and (4) enhance sustained clearance overall, as compared to mono-AK photodynamic therapy or mono-imiquimod topical therapy alone. In other words, this disclosure provides for new and improved actinic keratosis treatments that combine photodynamic therapy and low dose and short duration imiquimod topical therapies to treat both clinical and subclinical lesions more effectively. This disclosure thus provides numerous surprising advantages over current photodynamic therapy for actinic keratosis treatment when used alone.

This disclosure also overcomes the above-mentioned limitations associated with the treatment of actinic keratosis with FDA-approved ALDARA 5% imiquimod cream through the novel complementary/combination/follow-on use, in conjunction with photodynamic therapy, of improved imiquimod treatment regimens of short duration, lower dosage strength imiquimod pharmaceutical formulations, and simplified dosing regimens to treat actinic keratosis. The methods described herein, which are directed to the use of complementary, combination, or follow-on photodynamic therapy and imiquimod topical therapy, cover larger treatment areas, have shorter durations of therapies, use lower imiquimod dosage strengths, have simplified daily dosing regimens, and have a lower incidence of application site reactions, as compared to treatment of actinic keratosis with ALDARA 5% imiquimod cream.

II. Methods of Treating Actinic Keratosis

In one aspect, this disclosure discloses methods of treating actinic keratosis (AK) in a subject in need thereof by administering a combination of lower dosage strength imiquimod therapy and photodynamic therapy. In some embodiments, the method comprises: topically applying to a treatment area on the subject a composition comprising a lower dosage strength formulation of imiquimod; and administering photodynamic therapy to the treatment area or to an AK lesion in the treatment area; thereby treating AK in the subject.

Imiquimod Topical Therapy

In some embodiments, the method of applying imiquimod to a treatment area comprises administering an imiquimod formulation as described hereinbelow, e.g., in the Examples section below. In some embodiments, the method comprises administering a composition comprising a lower dosage strength imiquimod formulation. In some embodiments, the lower dosage strength imiquimod formulation comprises imiquimod in an amount from about 1% (w/w) to about 4.25% (w/w). In some embodiments, the lower dosage strength imiquimod formulation comprises imiquimod in an amount of about 2.5% (w/w) or about 3.75% (w/w). In some embodiments, the lower dosage strength imiquimod formulation comprises imiquimod in an amount of about 2.5% (w/w). In some embodiments, the lower dosage strength imiquimod formulation comprises imiquimod in an amount of about 3.75% (w/w). In some embodiments, the composition further comprises a pharmaceutically acceptable vehicle for imiquimod.

In some embodiments, the composition comprises a lower dosage strength imiquimod formulation that is selected from the group of imiquimod formulations listed in Table 10. In some embodiments, the composition comprises an imiquimod formulation that is selected from the group of 2.5% (w/w) or 3.75% (w/w) imiquimod formulations listed in Table 10.

In some embodiments, the composition comprises imiquimod in an amount from about 1% (w/w) to about 5% (w/w). In some embodiments, the composition comprises imiquimod in an amount of about 5% (w/w). In some embodiments, the amount of imiquimod in the composition is not 5% (w/w). In some embodiments, the amount of imiquimod in the composition is lower than 5% (w/w).

In some embodiments, about 25-500 mg (e.g., about 25, about 50, about 75, about 100, about 150, about 200, about 250, about 300, about 350, about 400, about 450, or about 500 mg) of the composition is administered per application. In some embodiments, about 250-500 mg of the composition is administered per application.

In some embodiments, the composition comprising a lower dosage strength imiquimod formulation is administered topically to the skin. In some embodiments, the composition is not removed from the skin for at least about 8 hours. In some embodiments, the 8 hours is overnight. In some embodiments, the composition comprising imiquimod is removed from the skin after the dosage period (e.g., after about 8 hours). In some embodiments, the imiquimod composition is removed with mild soap and water.

In some embodiments, about 5 mg to about 20 mg (e.g., about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, or about 20) mg of imiquimod is applied daily. In some embodiments, about 9.4 mg to about 18.8 mg of imiquimod is applied daily. In some embodiments, about 6.2 mg to about 12.5 mg of imiquimod is applied daily.

In some embodiments, the composition comprising imiquimod is applied as a field-directed treatment. In some embodiments, the composition comprising imiquimod is applied as a lesion-directed treatment.

In some embodiments, the imiquimod treatment comprises applying an effective amount of imiquimod to the treatment area at least once per day for up to two weeks. It may also comprise applying an effective amount of imiquimod to the treatment area at least once per day for up to three weeks.

In some embodiments, the imiquimod therapy comprises a first treatment period and a second treatment period. In some embodiments, the first and second treatment periods are separated by a non-treatment period. In some embodiments, the length of time of the non-treatment period is the same length or about the same length as the length of time of a treatment period(s).

In some embodiments, one or more voluntary "rest periods" may be taken by the subject during the imiquimod topical therapy treatment period, for example, due to lack of tolerability of the drug. A rest period (i.e., a period during a prescribed treatment period in which no imiquimod topical therapy is administered) can be a period of any length. In some embodiments, a rest period skips one dose, two doses, three doses, four doses, five doses, six doses, seven doses, or more. In some embodiments, a rest period is one day, two days, three days, four days, five days, or more.

2×2×2 Treatment Course

In some embodiments, the imiquimod is applied in a six-week treatment course. In some embodiments, the imiquimod treatment comprises about 2 weeks of applying the imiquimod composition (e.g., applying the composition daily), then up to about 2 weeks of a non-treatment period, and then up to about 2 weeks of applying the imiquimod composition (e.g., applying the composition daily). In some embodiments, the imiquimod treatment comprises 2 weeks of applying the imiquimod composition (e.g., applying the composition daily), then 2 weeks of a non-treatment period, and then 2 weeks of applying the imiquimod composition (e.g., applying the composition daily) ("2×2×2").

In some embodiments, the composition comprising imiquimod is applied up to about 28 times to the area during the entire course of treatment. For example, the imiquimod treatment may comprise applying the imiquimod daily for a first two week cycle, resting for two weeks and applying the imiquimod daily for a second two week cycle. It may also comprise: applying an effective amount of imiquimod to a treatment area at least once per day for up to about two weeks to complete a first cycle; resting for up to about two weeks, wherein no imiquimod is applied to the patient; and applying an effective amount of imiquimod to the treatment area at least once per day for up to about two weeks to complete a second cycle. It may also comprise: applying an effective amount of imiquimod to a treatment area once per day for up to two weeks to complete a first cycle; resting for up to two weeks, wherein no imiquimod is applied to the patient; and applying an effective amount of imiquimod to the treatment area once per day for up to two weeks to complete a second cycle. It may also comprise applying an effective amount of imiquimod to the treatment area at least once per day for up to four weeks.

In some embodiments, about 40 mg to about 90 mg (e.g., 43.8 mg to 87.6 mg) of imiquimod is applied in one week of a two-week treatment period. In some embodiments, about 85 mg to about 175 mg (e.g., 87.5 mg to 175 mg) of imiquimod is applied in a two-week treatment period. In some embodiments, about 175 mg to about 350 mg of imiquimod is applied in a four-week treatment course.

In some embodiments, about 65 mg to about 135 mg (e.g., 65.6 mg to 131.3 mg) of imiquimod is applied in one week of a two-week treatment period. In some embodiments, about 130 mg to about 265 mg (e.g., 131.2 mg to 262.5 mg) of imiquimod is applied in a two-week treatment period. In some embodiments, about 260 mg to about 525 mg (e.g., 262.5 mg to 525 mg) of imiquimod is applied in a four-week treatment course.

3×3×3 Treatment Course

In some embodiments, the imiquimod is applied in a nine-week treatment course. In some embodiments, the imiquimod treatment comprises about 3 weeks of applying the imiquimod composition (e.g., applying the composition daily), then up to about 3 weeks of a non-treatment period, and then up to about 3 weeks of applying the imiquimod composition (e.g., applying the composition daily). In some embodiments, the imiquimod treatment comprises 3 weeks of applying the imiquimod composition (e.g., applying the composition daily), then 3 weeks of a non-treatment period, and then 3 weeks of applying the imiquimod composition (e.g., applying the composition daily) ("3×3×3").

In some embodiments, the composition comprising imiquimod is applied up to about 42 times to the area during the entire course of treatment. For example, the imiquimod treatment may comprise applying the imiquimod daily for a first three week cycle, resting for three weeks and then applying the imiquimod daily for a second three week cycle. It may also comprise: applying an effective amount of imiquimod to a treatment area at least once per day for up to about three weeks to complete a first cycle; resting for up to about three weeks, wherein no imiquimod is applied to the patient; and applying an effective amount of imiquimod to the treatment area at least once per day for up to about three weeks to complete a second cycle. It may also comprise: applying an effective amount of imiquimod to a treatment area once per day for up to three weeks to complete a first cycle; resting for up to three weeks, wherein no imiquimod is applied to the patient; and applying an effective amount of imiquimod to the treatment area once per day for up to three weeks to complete a second cycle. It may also comprise applying an effective amount of imiquimod to the treatment area at least once per day for up to six weeks.

In some embodiments, about 40 mg to about 90 mg (e.g., 43.8 mg to 87.6 mg) of imiquimod is applied in one week of a three-week treatment period. In some embodiments, about 130 mg to about 265 mg (e.g., 131.3 mg to 262.6 mg) of imiquimod is applied in a three-week treatment period. In some embodiments, about 260 mg to about 525 mg (e.g., 262.5 mg to 525 mg) of imiquimod is applied in a six-week treatment course.

In some embodiments, about 65 mg to about 135 mg (e.g., 65.6 mg to 131.3 mg) of imiquimod is applied in one week of a two-week treatment period. In some embodiments, about 195 mg to about 395 mg (e.g., 196.9 mg to 393.8 mg) of imiquimod is applied in a three-week treatment period. In some embodiments, about 390 mg to about 790 mg (e.g., 393.8 mg to 787.5 mg) of imiquimod is applied in a six-week treatment course.

According to embodiments, a lower dosage strength imiquimod formulation comprises between about 1% and about 4.25% imiquimod, or between about 2.5% and about 3.75% imiquimod, and short and simplified imiquimod dosing regimens, e.g., up to about 2 to 3 weeks on, up to about 2 to 3 weeks off and up to about 2 to 3 weeks on, include those discussed and described in U.S. Pat. Nos. 8,236,816 and 8,222,270 and in U.S. Patent Publication No. 2011/0263635, the contents of each of which are incorporated herein by reference in its entirety.

Photodynamic Therapy

Photodynamic therapy is a form of energy activated therapy for destroying abnormal or diseased tissue is photodynamic therapy. The photodynamic therapy of this disclosure can be any photodynamic therapy known in the art. For example, photodynamic therapy can be a two-step treatment process comprising administering a photoreactive compound on a treatment area of the subject, followed by irradiating the treatment area of the subject with a light having a wavelength corresponding at least in part to the characteristic light absorption wavelength of the photoreactive compound. The photoreactive compound can be any compound known in the art, including, but not limited to, indocyanine, methylene blue, toluidine blue, aminolevulinic acid, methyl aminolevulinate, chlorins, phthalocyanines, porphyrins, purpurins, bacteriochlorins, merocyanines, psoralens, texaphyrins, and combinations thereof.

Typically, the administration of photodynamic therapy comprises administering one or more sessions of therapy (e.g., one, two, three, four, or more sessions of therapy) to the subject. According to embodiments, a session includes both the administration of a photoreactive compound to a treatment area and the irradiation of the treatment area, which can occur over the course of several hours or one or more days or weeks. According to other embodiments, a session comprises just irradiation of the treatment area alone. Prior to irradiation, the skin may be sensitized, for example by covering the skin for a period of time. In some embodiments, the photodynamic therapy is administered in two sessions. In some embodiments, the photodynamic therapy is administered in only one session.

In some embodiments, the photodynamic therapy comprises treatment with aminolevulinic acid (ALA) (e.g., Levulan®, DUSA Pharmaceuticals, Inc.) followed by blue light illumination at a wavelength of about 400-450 nm (e.g., BLU-U® Blue Light Photodynamic Therapy, DUSA Pharmaceuticals, Inc.). In some embodiments, the photodynamic therapy comprises treatment with methyl aminolevulinate (MAL) (e.g., Metvixia®, Galderma S.A.) followed by red light illumination at a wavelength of about 630 nm (e.g., Aktilite® CL128, Galderma S.A.). In some embodiments, the photodynamic therapy comprises treatment with a patch (e.g., a self-adhesive patch) comprising a photoreactive compound, e.g., a patch comprising ALA, followed by light illumination at a suitable wavelength. In some embodiments, the photodynamic therapy comprises treatment with a medicated plaster comprising a photoreactive compound, e.g., ALA (e.g., Alacare®, Spirig Pharma AG) followed by light illumination at a suitable wavelength. According to still other embodiments, the patch comprises a covering that does not contain a photoreactive substance.

In some embodiments, the photodynamic therapy is field-directed. In some embodiments, the photodynamic therapy is lesion-directed.

Timing of Imiquimod Topical Therapy and Photodynamic Therapy Treatments

In some embodiments, the photodynamic therapy and the imiquimod topical therapy are sequentially applied. In some embodiments, the photodynamic therapy treatment is administered after the completion of the imiquimod therapy. Administration of imiquimod topical therapy before photodynamic therapy may reduce the amount of photodynamic therapy that needs to be administered in order to achieve partial clearance or complete clearance (e.g., may reduce the number of photodynamic therapy treatment sessions that are administered). Treatment with imiquimod (e.g., field-directed imiquimod treatment) may cause sub-clinical lesions that otherwise would not have been visible to become visible, therefore allowing the photodynamic therapy to be initially administered to more AK lesions than would have been treated in the absence of the imiquimod treatment. In some embodiments, the photodynamic therapy treatment is administered within about 14 days after the completion of the imiquimod treatment. In some embodiments, there is a non-treatment period in between the completion of the imiquimod therapy and the commencement of the photodynamic therapy. In some embodiments, there is a non-treatment period of up to about 28 days, e.g., about 1, 2, 3, 4, 5, 6, 7, 8, 9, 10, 11, 12, 13, 14, 15, 16, 17, 18, 19, 20, 21, 22, 23, 24, 25, 26, 27, or 28 days. In some embodiments, the non-treatment period between the completion of the imiquimod therapy and the commencement of the photodynamic therapy is from about 7 to about 14 days, or about 7 days, or about 14 days. In some embodiments, photodynamic therapy is administered no more than 28 days after the completion of the imiquimod therapy. In some embodiments, photodynamic therapy is administered no more than 14 days after the completion of the imiquimod therapy.

In some embodiments, the photodynamic therapy treatment is administered prior to the commencement of the imiquimod therapy. In some embodiments, the photodynamic therapy treatment is administered within about 14 days prior to the commencement of the imiquimod treatment. In some embodiments, there is a non-treatment period in between the completion of the photodynamic therapy and the commencement of the imiquimod therapy. In some embodiments, there is a non-treatment period of up to about 28 days, e.g., about 1, 2, 3, 4, 5, 6, 7, 8, 9, 10, 11, 12, 13, 14, 15, 16, 17, 18, 19, 20, 21, 22, 23, 24, 25, 26, 27, or 28 days. In some embodiments, the non-treatment period between the completion of the photodynamic therapy and the commencement of the imiquimod therapy is from about 7 to about 14 days, or about 7 days, or about 14 days. In some embodiments, photodynamic therapy is administered no more than 28 days before the commencement of the imiquimod therapy. In some embodiments, photodynamic therapy is administered no more than 14 days before the commencement of the imiquimod therapy.

In some embodiments, the photodynamic therapy and the imiquimod topical therapy are concomitantly applied. In some embodiments, the photodynamic therapy is administered during an imiquimod treatment course (e.g., during a six-week treatment course or during a nine-week treatment course). In some embodiments, the photodynamic therapy is administered during an imiquimod treatment period (i.e., a time period in which imiquimod is being administered, e.g., during a two-week treatment period or during a three-week treatment period). In some embodiments, the photodynamic therapy is administered during a rest period (i.e., a period during a prescribed treatment period in which no imiquimod topical therapy is administered). In some embodiments, the photodynamic therapy is administered during a non-treatment period (e.g., during a two-week non-treatment period between two treatment cycles in a six week regimen, or during a three-week non-treatment period between two treatment cycles in a nine week regimen). In some embodiments, the photodynamic therapy is administered during any combination of one or more treatment periods, rest periods, and/or non-treatment periods. In some embodiments, the photodynamic therapy is administered during any period of imiquimod treatment.

Treatment of Actinic Keratosis

In some embodiments, the treatment area is the full or entire face, scalp, ears, neck, back of the neck, torso, chest, upper chest, back, stomach, arms, forearms, hands or the tops of the hands, legs, feet, and/or lips. In some embodiments, the treatment area is a portion of the face or the full face. In some embodiments, the treatment area is a portion of the balding scalp or the entire balding scalp. In some embodiments, the treatment area is a portion of the upper torso, for example, the upper chest (décolletage) area.

In some embodiments, the treatment area is an area of greater than 25 $cm^2$ (e.g., a treatment area greater than a 5 cm×5 cm area in any shape). In some embodiments, the treatment area is an area of at least about 25 $cm^2$, at least about 50 $cm^2$, at least about 75 $cm^2$, at least about 100 $cm^2$, at least about 125 $cm^2$, at least about 150 $cm^2$, at least about 175 $cm^2$, at least about 200 $cm^2$, at least about 225 $cm^2$, or at least about 250 $cm^2$. In some embodiments, the treatment area is an area of from about 25 $cm^2$ to about 250 $cm^2$. In some embodiments, the treatment area is an area of from about 25 $cm^2$ to about 200 $cm^2$. In some embodiments, the treatment area is an area no greater than about 250 $cm^2$.

In some embodiments, the actinic keratosis lesions to be treated are clinically typical, visible, or palpable lesions. In some embodiments, the actinic keratosis lesions to be treated are hypertrophic lesions. In some embodiments, the actinic keratosis lesions to be treated are non-hypertrophic lesions. In some embodiments, the actinic keratosis lesions to be treated are non-palpable lesions. In some embodiments, the actinic keratosis lesions to be treated are sub-clinical lesions. In some embodiments, the actinic keratosis lesions include at least one clinically visible or palpable lesion and at least one hypertrophic lesion. In some embodiments, the actinic keratosis lesions include at least one clinically visible or palpable lesion and at least sub-clinical lesion. In some embodiments, the actinic keratosis lesions include at least one clinically visible or palpable lesion and at least one non-hypertrophic or one non-palpable lesion.

In some embodiments, a treatment area has at least 4 AK lesions (e.g., at least 4 clinically visible, palpable, non-hypertrophic, and/or non-palpable lesions). In some embodiments, a treatment area has at least about 5, 6, 7, 8, 9, 10, 11, 12, 13, 14, 15, 16, 17, 18, 19, 20 or more AK lesions. In some embodiments, a treatment area has from about 4 to about 8, from about 4 to about 10, from about 4 to about 12, from about 4 to about 15, from about 4 to about 20, from about 5 to about 10, from about 5 to about 15, or from about 5 to about 20 AK lesions. In some embodiments, a treatment area has from about 5 to about 20 AK lesions or more.

In some embodiments, treatment with the imiquimod therapy and photodynamic therapy as described herein increases the number of AK lesions for some period of time. In some embodiments, treatment with the imiquimod therapy and photodynamic therapy as described herein results in partial clearance of AK lesions as compared to baseline (e.g., clearance of at least 25%, at least 30%, at least 40%, at least 50%, at least 60%, at least 70%, at least 75% or more of baseline AK lesions). In some embodiments, treatment with the imiquimod therapy and photodynamic therapy as described herein results in complete clearance of AK lesions as compared to baseline.

In some embodiments, treatment of a population of subjects with the imiquimod therapy and photodynamic therapy as described herein results in a statistically significant improvement in the percent of total clearance of AK in the population of subjects as compared to treatment with a placebo. In some embodiments, treatment of a population of subjects with the imiquimod therapy and photodynamic therapy as described herein results in partial clearance of AK in the population of subjects (e.g., clearance of at least 25%, at least 30%, at least 40%, at least 50%, at least 60%, at least 70%, at least 75% or more of baseline AK lesions). In some embodiments, treatment of a population of subjects with the imiquimod therapy and photodynamic therapy as described herein results in complete clearance of AK in the population of subjects.

In some embodiments, a subject in need of treatment is a subject having a plurality of clinically visible, palpable, non-palpable, non-hypertrophic, and/or hypertrophic lesions. In some embodiments, the subject is at least 12 years old. In some embodiments, the subject is an adult. In some embodiments, the subject is immunocompetent (e.g., an immunocompetent adult). In some embodiments, the subject is female. In some embodiments, the subject is male.

III. Imiquimod Formulations

Formulations and Pharmaceutical Compositions

In another aspect, this disclosure provides lower dosage strength imiquimod formulations, and compositions comprising lower dosage strength imiquimod formulations, for use in the treatment of actinic keratosis, e.g., for use in complementary or combination with photodynamic therapy for the treatment of actinic keratosis. In some embodiments, the imiquimod formulation or composition comprising an imiquimod formulation comprises imiquimod in an amount by weight of between about 1% and about 4.25%. In some embodiments, the formulation of composition comprising an imiquimod formulation comprises imiquimod in an amount of about 2.5% (w/w). In some embodiments, the formulation of composition comprising an imiquimod formulation comprises imiquimod in an amount of about 3.75% (w/w). In some embodiments, the imiquimod is the sole pharmaceutically active ingredient that is required to be applied to the treatment area.

In some embodiments, the imiquimod formulation contains imiquimod in an amount by weight of about 1.5%, 1.75%, 2.0%, 2.25%, 2.5%, 2.75%, 3.0%, 3.25%, 3.5%, 3.75%, 4.0%, or 4.25%. In some embodiments, the imiquimod formulation contains imiquimod in an amount by weight of from about 1% to about 4.0%, from about 1.5% to about 4.0%, from about 2.0% to about 4.0%, from about 2.5% to about 4.0%, from about 1.0% to about 3.75%, from about 1.5% to about 3.75%, from about 2.0% to about 3.75%, or from about 2.5% to about 3.75%. In some embodiments, the imiquimod formulations contains imiquimod in an amount by weight of between about 2.5% and about 3.75%. Examples of formulations from which the imiquimod formulation may be selected include, but are not limited to, the group of formulations listed in Table 10 and/or Example 23.

In some embodiments, the imiquimod formulation contains imiquimod in an amount by weight of about 2.5%. Examples include, but are not limited to, those 2.5% imiquimod formulations set forth in Example 23. In some embodiments, the imiquimod formulation contains imiquimod in an amount by weight of about 3.75% imiquimod. Examples include, but are not limited to, those 3.75% imiquimod formulations set forth in Example 23.

In some embodiments, the effective amount of the imiquimod is from about 1.5% to about 4.25% by weight. In some embodiments, the effective amount of the imiquimod is up to about 4.25% by weight. In some embodiments, the effective amount of the imiquimod is up to about 3.75% by weight. In some embodiments, the effective amount of the imiquimod is about 3.75% by weight. In some embodiments, the effective amount of the imiquimod is up to about 2.5% by weight. In some embodiments, the effective amount of the imiquimod is about 2.5% by weight.

In some embodiments, the imiquimod composition comprises a lower dosage strength of 1-isobutyl-1H-imidazo[4,5-c]-quinolin-4-amine or 1-(2-methylpropyl)-1H-imidazo[4,5-c]quinolin-4-amine (imiquimod) for delivering an effective amount of imiquimod; and a pharmaceutically acceptable vehicle for imiquimod. In some embodiments, the pharmaceutically acceptable vehicle comprises a fatty acid. In some embodiments, the fatty acid is selected from the group consisting of isostearic acid, palmitic acid, stearic acid, linoleic acid, unrefined oleic acid, refined oleic acid, SUPER REFINED® oleic acid NF (e.g., CRODA), and a combination thereof. In some embodiments, the fatty acid is isostearic acid. In some embodiments, the fatty acid is palmitic acid. In some embodiments, the fatty acid is stearic acid. In some embodiments, the fatty acid is linoleic acid. In some embodiments, the fatty acid is unrefined oleic acid. In some embodiments, the fatty acid is refined oleic acid. In some embodiments, the fatty acid is SUPER REFINED® oleic acid NF. In some embodiments, the pharmaceutically acceptable vehicle is present in a total amount from about 3% to about 45% by weight (e.g., about 3%, about 5%, about 10%, about 15%, about 20%, about 25%, about 30%, about 35%, about 40%, or about 45% by weight) based on the total weight of the formulation. In some embodiments, the pharmaceutically acceptable vehicle is present in a total amount from about 5% to about 30% by weight based on the total weight of the formulation.

A pharmaceutical formulation of this disclosure can be in any form known to the art, such as a cream, an ointment, a foam, a gel, a lotion or a pressure-sensitive adhesive composition, each form containing the necessary elements in particular amounts and further containing various additional elements. In some embodiments, an imiquimod formulation as described herein is formulated into a topical formulation further comprising a pharmaceutically acceptable vehicle. The topical formulation may be a cream.

A cream of this disclosure contains an effective amount of imiquimod, such as from about 1% (w/w) to about 4.25% (w/w) imiquimod based on the total weight of the cream, or from about 2.5% (w/w) to about 3.75% (w/w) imiquimod based on the total weight of the cream, or about 2.5% (w/w) or about 3.75% (w/w) imiquimod based on the total weight of the cream; and from about 5% (w/w) to about 30% (w/w) fatty acid (e.g., isostearic acid, palmitic acid, stearic acid, linoleic acid, unrefined oleic acid, refined oleic acid, or SUPER REFINED® oleic acid NF), based on the total weight of the cream. In some embodiments, a cream further comprises one or more optional ingredients such as emollients, emulsifiers, thickeners, and/or preservatives.

Emollients include, but are not limited to, long chain alcohols, e.g., cetyl alcohol, stearyl alcohol and cetearyl alcohol; hydrocarbons such as petrolatum and light mineral oil; and acetylated lanolin. A cream can contain one or more of these emollients. According to embodiments, the total amount of emollient in a cream is about 5% to about 30% by weight (e.g., about 5%, about 10%, about 15%, about 20%, about 25%, or about 30% by weight), or about 5% to about 10% by weight based on the total weight of the cream.

Emulsifiers include, but are not limited to, nonionic surface active agents, e.g., polysorbate 60, sorbitan monostearate, polyglyceryl-4 oleate, and polyoxyethylene(4)lauryl ether. A cream can contain one or more emulsifiers. According to embodiments, the total amount of emulsifier is about 2% to about 14% (e.g., about 2%, about 3%, about 4%, about 5%, about 6%, about 7%, about 8%, about 9%, about 10%, about 11%, about 12%, about 13%, or about 14%), or about 2% to about 6% by weight based on the total weight of the cream.

Pharmaceutically acceptable thickeners include, but are not limited to, xanthum gum, guar gum, VEEGUM™ K (available from R. T. Vanderbilt Company, Inc.), and long chain alcohols (e.g., cetyl alcohol, stearyl alcohol or cetearyl alcohol). A cream can contain one or more thickeners. According to embodiments, the total amount of thickener present is about 3% to about 12% by weight based on the total weight of the cream.

Preservatives include, but are not limited to, methylparaben, propylparaben, and benzyl alcohol. The appropriate amount of such preservative(s) is known to those skilled in the art.

Optionally, an additional solubilizing agent such as benzyl alcohol, lactic acid, acetic acid, stearic acid, salicylic acid, any alpha-hydroxy acid such as glycolic acid, or hydrochloric acid can be included in a cream of this disclosure. If an additional solubilizing agent is used, the amount present is from about 1% to about 12% by weight based on the total weight of the cream.

Optionally, a cream of this disclosure can contain a humectant such as glycerin, skin penetration enhancers such as butyl stearate, and additional solubilizing agents.

According to embodiments, a cream consists of an oil phase and a water phase mixed together to form an emulsion. In some embodiments, the amount of water present in a cream of this disclosure is about 45% to about 85% by weight based on the total weight of the cream. The oil phase of a cream of this disclosure can be prepared by first combining the imiquimod and the fatty acid (if the cream contains benzyl alcohol, it can also be added at this point) and heating with occasional stirring to a temperature of about 50° C. to 85° C. When the imiquimod appears to be completely dissolved, the remaining oil phase ingredients are added and heating is continued until dissolution appears to be complete. The water phase can be prepared by combining all other ingredients and heating with stirring until dissolution appears to be complete. The creams of this disclosure are generally prepared by adding the water phase to the oil phase with both phases at a temperature of about 65° C. to 75° C. The resulting emulsion is mixed with a suitable mixer apparatus to give the desired cream.

An ointment of this disclosure contains an ointment base in addition to imiquimod and fatty acid. An ointment of this disclosure contains an effective amount of imiquimod, such as from about 1% (w/w) to about 4.25% (w/w) imiquimod based on the total weight of the ointment, or from about 2.5% (w/w) to about 3.75% (w/w) imiquimod based on the total weight of the ointment, or about 2.5% (w/w) or about 3.75% (w/w) imiquimod based on the total weight of the ointment; about 3% (w/w) to about 45% (w/w) fatty acid (e.g., isostearic acid, palmitic acid, stearic acid, linoleic acid, unrefined oleic acid, refined oleic acid, or SUPER REFINED® oleic acid NF), or about 3% (w/w) to about 30% (w/w) fatty acid, or about 3% (w/w) to about 25% (w/w) fatty acid; and from about 40% (w/w) to about 95% (w/w) ointment base, or from about 60% (w/w) to about 95% (w/w), all weights being based on the total weight of the ointment. Optionally, an ointment of this disclosure further comprises one or more of emulsifiers, emollients and/or thickeners.

A pharmaceutically acceptable ointment base such as petrolatum or polyethylene glycol 400 (available from Union Carbide) in combination with polyethylene glycol 3350 (available from Union Carbide) can be used.

An ointment according to this disclosure can be prepared by combining imiquimod with fatty acid and heating with occasional stirring to a temperature of about 65° C. When the imiquimod appears to be completely dissolved, the remaining ingredients are added and heated to about 65° C. The resulting mixture is mixed with a suitable mixer while being allowed to cool to room temperature.

A pressure-sensitive adhesive composition of this disclosure contains imiquimod, fatty acid, and a pressure sensitive adhesive polymer. According to embodiments, the adhesives utilized in a pressure sensitive adhesive composition of this disclosure are substantially chemically inert to imiquimod. A pressure sensitive adhesive composition of this disclosure contains an effective amount of imiquimod, such as from about 1% (w/w) to about 4.25% (w/w) imiquimod or from about 2.5% (w/w) to about 3.75% (w/w) imiquimod, or about 2.5% (w/w) or about 3.75% (w/w) imiquimod; and from about 5% (w/w) to about 30% (w/w) fatty acid (e.g., isostearic acid, palmitic acid, stearic acid, linoleic acid, unrefined oleic acid, refined oleic acid, or SUPER REFINED® oleic acid NF), or from about 10% (w/w) to about 40% (w/w) fatty acid, or from about 15% (w/w) to about 30% (w/w) fatty acid, or from about 20% (w/w) to about 30% (w/w) fatty acid; all weights being based on the total weight of the pressure sensitive adhesive composition.

Optionally, pressure sensitive adhesive compositions of this disclosure can also contain one or more skin penetration enhancers. The total amount of skin penetration enhancer(s) present in a pressure sensitive adhesive composition of this disclosure can be about 3% to about 25% by weight, or about 3% to about 10% by weight based on the total weight of the pressure sensitive adhesive composition.

A pressure-sensitive adhesive coated sheet material can be made from a pressure-sensitive adhesive composition of this disclosure in the form of an article such as a tape, a patch, a sheet, or a dressing.

According to embodiments, the adhesive polymer utilized in a pressure sensitive adhesive composition of this disclosure is substantially chemically inert to imiquimod. In some embodiments, the adhesive polymer is present in an amount of about 55% to about 85% by weight based on the total weight of the composition. Suitable adhesive polymers include acrylic adhesives that contain, as a major constituent (i.e., at least about 80% by weight of all monomers in the polymer), a hydrophobic monomeric acrylic or methacrylic acid ester of an alkyl alcohol, the alkyl alcohol containing 4 to 10 carbon atoms. Examples of suitable monomers are those discussed below in connection with the "A Monomer." These adhesive polymers can further contain minor amounts of other monomers such as the "B Monomers" listed below.

In some embodiments, adhesives include acrylic pressure-sensitive adhesive copolymers containing A and B Monomers as follows: Monomer A is a hydrophobic monomeric acrylic or methacrylic acid ester of an alkyl alcohol, the alkyl alcohol containing 4 to 10 carbon atoms, for example, 6 to 10 carbon atoms or 6 to 8 carbon atoms, or, in some embodiments, 8 carbon atoms. Examples of suitable A Monomers are n-butyl, n-pentyl, n-hexyl, isoheptyl, n-nonyl, n-decyl, isohexyl, 2-ethyloctyl, isooctyl and 2-ethylhexyl acrylates. In some embodiments, the A Monomer is isooctyl acrylate.

Monomer B is a reinforcing monomer selected from the group consisting of acrylic acid; methacrylic acid; alkyl acrylates and methacrylates containing 1 to 3 carbon atoms in the alkyl group; acrylamide; methacrylamide; lower alkyl-substituted acrylamides (i.e., the alkyl group containing 1 to 4 carbon atoms) such as tertiary-butyl acrylamide; diacetone acrylamide; n-vinyl-2-pyrrolidone; vinyl ethers such as vinyl tertiary-butyl ether; substituted ethylenes such as derivatives of maleic anhydride, dimethyl itaconate and monoethyl formate and vinyl perfluoro-n-butyrate. In some embodiments, B Monomers are acrylic acid, methacrylic acid, the above-described alkyl acrylates and methacrylates, acrylamide, methacrylamide, and the above-described lower alkyl substituted acrylamides. In some embodiments, the B Monomer is acrylamide.

In some embodiments, a pressure-sensitive adhesive copolymer containing A and B Monomers as set forth above contains the A Monomer in an amount by weight of from about 80% to about 98% of the total weight of all monomers in the copolymer. In some embodiments, the A Monomer is present in an amount by weight of from about 88% to about 98%, or is present in an amount by weight of from about 91% to about 98%. The B Monomer in such a copolymer is present in the pressure-sensitive adhesive copolymer in an amount by weight of about 2% to about 20%, or in some embodiments from about 2% to about 12%, or from about 2% to about 9% of the total weight of the monomers in the copolymer.

In another embodiment of a pressure-sensitive adhesive composition of this disclosure, the adhesive copolymer comprises from about 60% to about 80% by weight (for example, from about 70% to about 80% by weight) of the above-mentioned hydrophobic monomeric acrylic or methacrylic acid ester of an alkyl alcohol (i.e., Monomer A described above) based on the total weight of all monomers in the copolymer; from about 4% to about 9% by weight based on the total weight of all monomers in the copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower alkyl-substituted acrylamide, diacetone acrylamide and N-vinyl-2-pyrrolidone; and from about 15% to about 35% by weight (for example, from about 15% to about 25% by weight) of vinyl acetate based on the total weight of all monomers in the copolymer. In some embodiments, the acrylic or methacrylic acid ester is isooctyl acrylate and the reinforcing monomer is acrylamide.

The above described adhesive copolymers are known, and methods of preparation therefore are well known to those skilled in the art. The polymerization reaction can be carried out using a free radical initiator such as an organic peroxide (e.g., benzoylperoxide) or an organic azo compound (e.g., 2,2'-azobis(2,4-dimethylpentanenitrile), available under the trade designation "VAZO® 52" from DuPont Company).

Since pressure-sensitive adhesives such as those described above are inherently rubbery and tacky and are suitably heat and light stable, there is no need to add tackifiers or stabilizers. However, such can be added if desired.

Optionally, a pressure sensitive adhesive composition of this disclosure can also contain one or more skin penetration enhancers such as glyceryl monolaurate, ethyl oleate, isopropyl myristate, diisopropyl adipate and N,N-dimethyldodecylamine-N-oxide, either as a single ingredient or as a combination of two or more ingredients. In some embodiments, the skin penetration enhancer or enhancers form a substantially homogeneous mixture with the pressure sensitive adhesive polymer or copolymer. In some embodiments, the total amount of skin penetration enhancer(s) present in a pressure sensitive adhesive composition of this disclosure is from about 3% to about 25% by weight, or from about 3% to about 10% by weight based on the total weight of the adhesive composition.

In some embodiments, the skin penetration enhancer is a single ingredient, and the skin penetration enhancer is isopropyl myristate, diisopropyl adipate, ethyl oleate, or glyceryl monolaurate.

In some embodiments, a combination skin penetration enhancer is used, and the combination is a combination such as: ethyl oleate with glyceryl monolaurate; ethyl oleate with N,Ndimethyldodecylamine-N-oxide; glyceryl monolaurate with N,N-dimethyldodecylamine-N-oxide; and ethyl oleate with both glyceryl monolaurate and N,Ndimethyldodecylamine-N-oxide.

A pressure-sensitive adhesive composition of this disclosure can be prepared by combining dry adhesive, imiquimod, fatty acid, and skin penetration enhancer(s) with an organic solvent. Effective organic solvents are methanol and ethyl acetate. The total solids content of the adhesive coating is in the range of from about 15% to about 40%, for example, in the range of from about 20% to about 35% based on the total weight of the adhesive coating. The resulting mixture is shaken or mixed for a period of about 20 to 72 hours. When this method is used, in some embodiments the imiquimod is in micronized form (i.e., particle size of 1-2 microns in diameter). Optionally, the mixture can be heated during shaking. In some embodiments, the imiquimod is combined with the fatty acid and shaken at 40° C. until there appears to be complete dissolution. The remaining ingredients are added and the mixture is shaken for a period of about 20 to 72 hours.

The pressure-sensitive adhesive compositions described above can be coated onto one surface of a suitable backing of sheet material, such as a film, to form a pressure-sensitive adhesive coated sheet material. A pressure-sensitive adhesive coated sheet material of this disclosure can be prepared by knife coating a suitable release liner to a predetermined uniform thickness with a wet adhesive formulation. This adhesive coated release liner is then dried and laminated onto a backing using conventional methods. Suitable release liners include conventional release liners comprising a known sheet material, such as a polyester web, a polyethylene web, or a polystyrene web, or polyethylene-coated paper, coated with a suitable silicone-type coating such as that available under the trade designation DAUBERT™ 164Z, from Daubert Co. The backing can be occlusive, non-occlusive or a breathable film as desired. The backing can be any of the conventional materials for pressure-sensitive adhesive tapes, such as polyethylene, particularly low density polyethylene, linear low density polyethylene, high density polyethylene, randomly-oriented nylon fibers, polypropylene, ethylene-vinylacetate copolymer, polyurethane, rayon and the like. Backings that are layered, such as polyethylene-aluminum-polyethylene composites are also suitable. The backing should be substantially non-reactive with the ingredients of the adhesive coating, for example, low density polyethylene.

The pressure-sensitive adhesive coated sheet material of this disclosure can be made in the form of an article such as a tape, a patch, a sheet, a dressing or any other form known to those skilled in the art.

In some embodiments, an article in the form of a patch is made from an adhesive coated sheet material of this disclosure and applied to the skin of a mammal. The patch is replaced as necessary with a fresh patch to maintain the particular desired therapeutic effect of the imiquimod.

While the lower dosage strength imiquimod pharmaceutical formulations of this disclosure can be formulated into any form known to the art, such as a cream, an ointment, a foam, a gel, a lotion or a pressure-sensitive adhesive composition or patch, it should be understood that the creams, ointments, foams, gels and lotions may be packaged into any suitable container, such as unit-dose sachets or packets or multi-dose tubes or containers. A packaged amount of an imiquimod pharmaceutical formulation contemplated by this disclosure includes any suitable amount, such as about 250 mg to about 500 mg or more, or about 250 mg, about 300 mg, about 350 mg, about 400 mg, about 450 mg or about 500 mg unit-dose sachets or packets.

Properties of Imiquimod Formulations

The lower dosage strength imiquimod formulations of this disclosure, especially those wherein the vehicle comprises an isostearic acid as the fatty acid, are designed to have physical and chemical stability, solubility, emollient properties, and dose proportionate delivery similar to or better than ALDARA 5% imiquimod cream. More specifically, the lower dosage strength imiquimod formulations of this disclosure, especially those wherein the vehicle comprises an isostearic acid as the fatty acid, are believed to generally have similar or improved skin emolliency at the application site and dose proportionate release rates as to both the release rates of the imiquimod and the total amount of imiquimod released, relative to the ALDARA 5% imiquimod cream. In other words, the lower dosage strength imiquimod formulations of this disclosure are concentration influenced and have similar release rates to the ALDARA 5% imiquimod cream. Additionally, the greater the amount of imiquimod in the formulation, the faster and the greater the total amount of imiquimod that is released, evidencing that the amount in and the rate of release from the formulations are imiquimod concentration dependent. Thus, while the lower dose strength imiquimod formulations of this disclosure deliver different cumulative amounts to the stratum corneum and epidermis, i.e., local skin delivery, than the ALDARA 5% imiquimod cream, such lower dosage strength imiquimod formulations are believed to have a proportional and linear relationship that is similar with the ALDARA 5% imiquimod cream as to both the rate of imiquimod release and the total amount of imiquimod released and delivered locally to the skin over time, so that the imiquimod concentrations in the formulations of this disclosure, the imiquimod release rates and the amount of imiquimod unabsorbed and delivered to the stratum corneum and epidermis, which has been released from the formulations, are generally proportional and linear to the ALDARA 5% imiquimod cream.

In addition, the lower dosage strength imiquimod formulations of this disclosure, especially those wherein the vehicle comprises an isostearic acid as the fatty acid, are designed to be stable and fall within the range of the specifications for the commercially available ALDARA 5% imiquimod cream, such as to viscosity, pH, and stability, including microscopic and macroscopic stability. More specifically, the imiquimod present in the lower dosage strength imiquimod formulations of this disclosure, especially those wherein the vehicle comprises an isostearic acid as the fatty acid (monograph range: 90% to 110%) and benzyl alcohol (monograph range: 50% to 105%) remain within limits at both about 25° C. and about 40° C. over about a one-month period and within limits at both about 25° C. and about 40° C. over about a six-month period. Furthermore, the lower dosage strength imiquimod formulations of this disclosure, especially those wherein the vehicle comprises an isostearic acid as the fatty acid, remain stable for about six months at about 25° C. and about 40° C., and also remain stable with respect to macroscopic and microscopic appearance, viscosity (monograph range: 2,000 to 35000 cPs), and pH (monograph range 4.0 to 5.5). In addition, the lower dosage strength imiquimod formulations of this disclosure are uniquely designed to meet the requirements specified in both the United States Pharmacopeia ("USP") and the European Pharmacopeia ("EP") as to preservative efficacy and remain free of degradation products when stored at about 25° C./60% relative humidity ("RH"), about 30° C./65% RH and about 40° C./75% RH over about one, about two, about three, or about six months and analyzed at about 318 nm wavelength.

An in-vivo serum profile can be determined for an imiquimod lower dosage strength formulation of this disclosure (e.g., a formulation comprising about 2.5% (w/w) or about 3.75% (w/w/) imiquimod). For example, the serum profile may relate to characteristics of the formulation such as $T_{max}$ (i.e., the time when the maximum imiquimod serum concentration is reached at steady state following topical application of a lower dosage strength imiquimod formulation of this disclosure, i.e., when the rate of imiquimod absorption equals the rate of imiquimod elimination); $C_{max}$ (i.e., the maximum imiquimod serum concentration that is reached at steady state following topical application of a lower dosage strength imiquimod formulation of this disclosure, i.e., when the rate of imiquimod absorption equals the rate of imiquimod elimination); $C_{min}$ (i.e., the minimum measurable imiquimod serum concentration; e.g., imiquimod serum concentration that is observed immediately prior to dosing on Days 7, 14, 21 and 22 (24 hours post-dose)); $T_{1/2}$ (i.e., the time required for half of the quantity of maximum imiquimod serum concentration to be eliminated once steady state is achieved following topical application of a lower dosage strength imiquimod formulation); $AUC_{0-24}$ (i.e., the area under the serum imiquimod concentration versus a 24 hour time curve following topical application of a lower dosage strength imiquimod formulation of this disclosure, i.e., a measure of imiquimod exposure over a 24 hour period); $AUC_{0-t}$ (i.e., the area under the imiquimod serum concentration versus time curve, from 0 to the time of the last non-zero concentration on Day 1); $R_{AUC}$ (i.e., the accumulation ratio, calculated as the $AUC_{0-24}$ value during multiple-imiquimod dose administration divided by the $AUC_{0-24}$ value following the first dose (i.e., Day 21/Day 1)); $AUC_{0-inf}$ (i.e., the area under the imiquimod serum concentration versus time curve, from 0 to infinity); $R_{Cmax}$ (i.e., the accumulation ratio; calculated as the $C_{max}$ value during multiple-dose administration divided by the $C_{max}$ value following the first dose (i.e., Day 21/Day 1)); $\lambda_{z\ EFF}$ (i.e., the effective elimination rate constant, calculated as $-\ln(1-1/R_{AUC})$/tau); $T_{1/2EFF}$ (i.e., the effective half-life for accumulation; calculated as $0.693/\lambda_{z\ EFF}$); and $\lambda z$ (i.e., an elimination rate constant, i.e., the rate at which imiquimod disappears from the site of measurement once steady state is achieved following topical application of a lower dosage strength imiquimod formulation).

In some embodiments, an imiquimod lower dosage strength formulation of this disclosure (e.g., a formulation comprising about 2.5% (w/w) or about 3.75% (w/w/) imiquimod) has an in-vivo serum profile selected from the group consisting of:

(a) a Day 21 $T_{max}$ of from about 4 hours to about 16 hours, for example, a mean $T_{max}$ of about 7.4 hours with a standard deviation ("SD") of about 3.5, a median $T_{max}$ of about 9 hours and a geometric mean $T_{max}$ of about 6.6 hours and a coefficient of variation ("CV") of about 48%;

(b) a Day 21 $C_{max}$ of from about 0.07 to about 0.6 ng/ml, for example, a mean $C_{max}$ of about 0.3 ng/ml with a standard deviation of about 0.16, a median $C_{max}$ of about 0.35 and a geometric mean $C_{max}$ of about 0.27 ng/ml and a coefficient of variation of about 49%;

(c) a Day 21 $T_{1/2}$ of from about 9.7 to about 84 hours, for example, a mean $T_{1/2}$ of about 29.3 hours with a standard deviation of about 17, a median $T_{1/2}$ of about 25.6 hours and a geometric mean $T_{1/2}$ of about 26 hours and a coefficient of variation of about 58%;

(d) a Day 21 $AUC_{0-24}$ of from about 1.1 to about 12 ng-hr/ml, for example, a mean $AUC_{0-24}$ of about 6 ng-hr/ml with a standard deviation of about 3, a median $AUC_{0-24}$ of about 7 ng hr/ml and a geometric mean $AUC_{0-24}$ of about 5 ng hr/ml and a coefficient of variation of about 52%;

(e) a Day 21 $\lambda z$ of from about 0.008 $hr^{-1}$ to about 0.07 $hr^{-1}$, for example, a mean $\lambda z$ of about 0.03 $hr^{-1}$ with a standard deviation of about 0.01, a median $\lambda z$ of about 25.6 $hr^{-1}$ and a geometric mean $\lambda z$ of about 0.03 $hr^{-1}$ and a coefficient of variation of about 49%;

(f) a Day 21 $C_{min}$ of from about 0.06 to about 0.4, for example, a mean $C_{min}$ of about 0.20 with an SD of about 0.11, a median $C_{min}$ of about 0.19 and a geometric mean $C_{min}$ of about 0.17 and a coefficient of variation of about 55%;

(g) at Day 14/7 (a ratio of the trough concentration at Day 14 over the trough concentration at Day 7), a trough concentration geometric mean ratio of about 1.09 with a 90% confidence interval ("CI") within a range of between about 0.8 and about 1.5;

(h) at Day 21/14 (a ratio of the trough concentration at Day 21 over the trough concentration at Day 14), a trough concentration geometric mean ratio of about 1.33 with a 90% confidence interval ("CI") within a range of between about 0.9 and about 1.9;

(i) at Day 22/21 (a ratio of the trough concentration at Day 22 over the trough concentration at Day 21) a trough concentration geometric mean ratio of about 0.93 with a 90% confidence interval ("CI") within a range of between about 0.6 and about 1.3;

(j) a mean peak imiquimod serum concentration of about 0.323 ng/ml at Day 21;

(k) a Day 21 RAUC of from about 1 to about 7, for example, a mean RAUC of about 4 with a standard deviation of about 2, a median RAUC of about 3.5 and a geometric mean RAUC of about 3.3 and a coefficient of variation of about 56%;

(l) a Day 21 $RC_{max}$ of from about 0.5 to about 5, for example, a mean $RC_{max}$ of about 3 with a standard deviation of about 1.5, a median $RC_{max}$ of about 2.7 and a geometric mean $RC_{max}$ of about 2.4 and a coefficient of variation of about 54%;

(m) a Day 21 $L\lambda_{eff}$ of from about 0.006 $hr^{-1}$ to about 0.08 $hr^{-1}$, for example, a mean $L\lambda_{eff}$ of about 0.02 $hr^{-1}$ with a standard deviation of about 0.02, a median $L\lambda z_{eff}$ of about 0.01 $hr^{-1}$ and a geometric mean $L\lambda_{eff}$ of about 0.16 $hr^{-1}$ and a coefficient of variation of about 97%; and (n) a Day 21 $T^{1/2}_{eff}$ of from about 8 hr to about 110 hr, for example, a mean $T^{1/2}_{eff}$ of about 55 hr with a standard deviation of about 36, a median $T^{1/2}_{eff}$ of about 50 hr and a geometric mean $T^{1/2}_{eff}$ of about 42 $hr^{-1}$ and a coefficient of variation of about 66%.

In some embodiments, the imiquimod formulation achieves a steady state by about week 2, e.g., between about day 8 and day 14, when approximately 500 mg or less of the formulation is applied daily for 21 days to a treatment area of about 200 $cm^2$ on the face or balding scalp of a subject.

It should be understood by those versed in this art that the pharmacokinetic parameters and any other performance characteristics reported above and herein, including for example mean peak serum concentration, are in the absence of photodynamic therapy and may mimic or may change for embodiments of this disclosure wherein photodynamic therapy is used in accordance with this disclosure and that such characteristics are contemplated by this disclosure.

In addition, this disclosure contemplates lower dosage strength formulations that are pharmaceutically equivalent, therapeutically equivalent, bioequivalent, and/or interchangeable, regardless of the method selected to demonstrate equivalents or bioequivalence, such as dermatopharmacokinetic and pharmacokinetic methodologies, microdialysis, in vitro and in vivo methods, and/or clinical endpoints. Thus, this disclosure contemplates lower dosage strength imiquimod formulations that are bioequivalent, pharmaceutically equivalent and/or therapeutic equivalent, especially, 2.5% and 3.75% lower dosage strength imiquimod formulations that are bioequivalent, pharmaceutically equivalent and/or therapeutically equivalent, when used daily in accordance with the short durations of therapy of this disclosure to treat actinic keratosis, e.g., used on treatment areas, e.g., on full face or balding scalp, that are between greater than about 25 $cm^2$ and about 250 $cm^2$ on a daily basis for up to about six weeks, including the 3×3×3 weeks 2-cycle treatment regimen, or for up to about 4 weeks, including the 2×2×2 weeks 2-cycle treatment regimen.

Thus, the treatment methods of this disclosure contemplate: (a) pharmaceutically equivalent lower dosage strength imiquimod formulations which contain the same amount of imiquimod in the same dosage form; (b) bioequivalent lower dosage strength imiquimod formulations which are chemically equivalent and which, when administered to the same individuals in the same dosage regimens, result in comparable bioavailabilities; (c) therapeutic equivalent lower dosage strength imiquimod formulations which, when administered to the same individuals in the same dosage regimens, provide essentially the same efficacy and/or toxicity; and (d) interchangeable lower dosage strength imiquimod formulations of this disclosure which are pharmaceutically equivalent, bioequivalent and therapeutically equivalent.

EXAMPLES

The following examples are offered to illustrate, but not to limit the claimed invention. Parts and percentages are by weight unless otherwise specified. Examples of creams, ointments and pressure sensitive adhesive compositions contemplated by this disclosure are described in U.S. Pat. Nos. 4,689,338 and 5,238,944, which are incorporated herein by reference in their entireties. Percent modifications for, e.g., imiquimod and vehicle, to generate imiquimod formulations as described herein are likewise contemplated by this disclosure. In addition, the formulations described and disclosed in U.S. Pat. Nos. 8,236,816 and 8,222,270 and in U.S. Patent Publication Nos. 2007/0123558, 2007/0264317, 2007/0900550, and 2011/0021555, and 2011/0263635 are also contemplated by this disclosure and are incorporated herein by reference in their entireties.

Preparative Method 1

Laboratory Scale Preparation of Isooctylacrylate/Acrylamide Copolymer

To a 114 gram narrow-mouth glass bottle were added: 18.6 g isooctyl acrylate, 1.4 g acrylamide, 0.04 g benzoyl peroxide, 27.0 g ethyl acetate and 3.0 g methanol. The solution was purged for thirty five seconds with nitrogen at a flow rate of one liter per minute. The bottle was sealed and placed in a rotating water bath at 55° C. for twenty-four hours to effect essentially complete polymerization. The polymer was diluted with ethyl acetate/methanol (90/10) to 23.2% solids and had a measured inherent viscosity of 1.26 dl/g in ethyl acetate.

Preparative Method 2

Pilot Plant Scale Preparation of Isooctylacrylate/Acrylamide Copolymer 155 kg isooctylacrylate, 11.6 kg acrylamide, 209.1 kg ethyl acetate and 23.2 kg methanol were charged to a clean, dry reactor. Medium agitation was applied. The batch was deoxygenated with nitrogen while heating to an induction temperature of 55° C. 114 g LUCIDOL™ 70 initiator (available from Pennwalt Corp.) mixed with 2.3 kg ethyl acetate was charged to the reactor. The temperature was maintained at 55° C. throughout the reaction. After 5.5 hours reaction time, 114 g LUCIDOL™ 70 mixed with 2.3 kg ethyl acetate were charged to the reactor. After 9.0 hours reaction time, an additional 114 g LUCIDOL™ 70 initiator mixed with 2.3 kg ethyl acetate were charged to the reactor. The reaction was continued until the percent conversion was greater than 98% as measured by gas chromatographic evaluation of residual monomer concentration. The resulting polymer solution was diluted to 25-28% solids with ethyl acetate/methanol (90/10) and had a measured Brookfield viscosity of 17,000-21,000 centipoises using spindle #4 at 12 rpm. The polymer had a measured inherent viscosity of 1.3-1.4 dl/g in ethyl acetate.

The above-mentioned procedure was found to provide a pressure-sensitive adhesive that is equivalent in the practice of this disclosure to a pressure-sensitive adhesive prepared according to Preparative Method 1.

A 25-30% solids solution of the isooctyl acrylate:acrylamide (93:7) adhesive copolymer in ethyl acetate/methanol (90/10) was coated onto a two-sided release liner using a knife-coater and coating at 0.5 mm in thickness. The adhesive-coated laminate was dried first at 82° C. for 3 minutes and then at 116° C. for 3 minutes. The dried adhesive coating was then stripped off the release liner and placed in a glass bottle. The foregoing procedure resulted in a reduction of the amount of any residual monomer in the adhesive copolymer.

Preparative Method 3

Preparation of Isooctyl Acrylate:Acrylamide:Vinyl Acetate (75:5:20) Copolymer

The procedure of Preparative Method 1 above acrylate, 8.0 g acrylamide, 32.0 g vinyl acetate, 0.32 g benzoyl peroxide, 216.0 g ethyl acetate and 24.0 g methyl alcohol. The resulting polymer was diluted with the ethyl acetate/methyl alcohol mixture to 21.52% solids. The adhesive polymer had a measured inherent viscosity of 1.40 dl/g in ethyl acetate at a concentration of 0.15 g/dl. Its Brookfield viscosity was 2,300 centipoise.

Preparative Method 4

Preparation of Isooctyl Acrylate Acrylamide:Vinyl Acetate (75:5:20) Copolymer

A master batch was prepared by combining 621.0 g of isooctyl acrylate, 41.4 g of acrylamide, 165.6 g of vinyl acetate, 1.656 g of 2,2'-azobis(2,4-dimethylpentanenitrile) (available from the DuPont Company as VAZO® 52), 884.52 g of ethyl acetate and 87.48 g of methanol. A 400 g portion of the resulting solution was placed in an amber quart bottle. The bottle was purged for two minutes with nitrogen at a flow rate of one liter per minute. The bottle was sealed and placed in a rotating water bath at 45° C. for twenty-four hours to effect essentially complete polymerization. The copolymer was diluted with 250 g of ethyl acetate/methanol (90/10) to 26.05% solids and had a measured inherent viscosity of 1.27 dl/g in ethyl acetate at a concentration of 0.15 g/dl. Its Brookfield viscosity was 5580 centipoise.

Example 1

A cream according to this disclosure was prepared from the following ingredients:

TABLE 1

| Component | % by Weight | Amount |
| --- | --- | --- |
| Oil Phase | | |
| 1-isobutyl-1H-imidazo[4,5-c]- | 1.0 | 40.0 g quinolin-4-amine |
| Isostearic acid | 10.0 | 400.0 g |
| Benzyl alcohol | 2.0 | 80.0 g |
| Cetyl alcohol | 2.2 | 88.0 g |
| Stearyl alcohol | 3.1 | 124.0 g |
| Polysorbate 60 | 2.55 | 102.0 g |
| Sorbitan monostearate | 0.45 | 18.0 g |
| Aqueous Phase | | |
| Glycerin | 2.0 | 80.0 g |
| Methylparaben | 0.2 | 8.0 g |
| Propylparaben | 0.02 | 0.8 g |
| Oil Phase | | |
| Purified water | 76.48 | 3059.2 g |

The materials listed in Table 1 above were combined according to the following procedure:

The glycerin, methylparaben, propylparaben and water were weighed into a 4 liter glass beaker then heated on a hot plate with stirring until the parabens isostearic acid and 1-isobutyl-1H-imidazo[4,5-c]-quinolin-4-amine were weighed into an 8 liter stainless steel beaker and heated on a hot plate until the amine was in solution (the temperature reached 69° C.). The benzyl alcohol, cetyl alcohol, stearyl alcohol, polysorbate 60 and sorbitan monostearate were added to the isostearic acid solution and heated on a hot plate until all material was dissolved (the temperature reached 75° C.). With both phases at approximately the same temperature (65°-75° C.), the water phase was added to the oil phase. The mixture was mixed with a homogenizer for 13 minutes then put into a cool water bath and mixed with a 3 inch propeller for 40 minutes (the temperature was 29° C.). The resulting cream was placed in glass jars.

Examples 2-9

Using the general method of Example 1, the cream formulations shown in Tables 2 and 3 were prepared.

TABLE 2

| Component | % by Weight | | | |
|---|---|---|---|---|
| | Example 2 | Example 3 | Example 4 | Example 5 |
| Oil Phase | | | | |
| 1-isobutyl-1H-imidazo-[4,5-1.0 c]quinolin-4-amine | 1.0 | 1.0 | 1.0 | 1.0 |
| Isostearic acid | 10.0 | 10.0 | 5.0 | 5.0 |
| Benzyl alcohol | | 2.0 | | |
| Cetyl alcohol | | 1.70 | | |
| Stearyl alcohol | | 2.3 | | |
| Cetearyl alcohol | 6.0 | | 6.0 | 6.0 |
| Polysorbate 60 | 2.55 | 2.55 | 2.55 | 2.55 |
| Sorbitan monostearate | 0.45 | 0.45 | 0.45 | 0.45 |
| BRIJ™ 30[a] | | | | 10.0 |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Oil Phase | | | | |
| Purified water | 77.78 | 77.78 | 82.78 | 72.78 |

[a]BRIJ™ 30 (polyoxyethylene(4) lauryl ether) is available from ICI Americas, Inc

TABLE 3

| Component | % by Weight | | | |
|---|---|---|---|---|
| | Example 6 | Example 7 | Example 8 | Example 9 |
| Oil Phase | | | | |
| 1-isobutyl-1H-imidazo-[4,5-1.0 c]quinolin-4-amine | 1.0 | 1.0 | 1.0 | 1.0 |
| Isostearic acid | 10.0 | 25.0 | 10.0 | 6.0 |
| Benzyl alcohol | | 2.0 | | |
| Cetyl alcohol | | 2.2 | 1.7 | |
| Stearyl alcohol | | 3.1 | 2.3 | |
| Cetearyl alcohol | 6.0 | | | 6.0 |
| Polysorbate 60 | 2.55 | 3.4 | 2.55 | 2.55 |
| Sorbitan monostearate | 0.45 | 0.6 | 0.45 | 0.45 |
| BRIJ™ 30[a] | 10.0 | | | |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 67.78 | 60.48 | 79.78 | 79.78 |

[a]BRIJ™ 30 (polyoxyethylene(4) lauryl ether) is available from ICI Americas, Inc Example 10

A cream according to this disclosure was prepared from the following ingredients in the following Table 4:

TABLE 4

| Component | % by Weight | Amount |
|---|---|---|
| Oil Phase | | |
| 1-isobutyl-1H-imidazo[4,5-c]quinolin-4-amine | 1.0 | 3.00 g |
| Isostearic acid | 5.0 | 15.0 g |
| White petrolatum | 15.0 | 45.0 g |
| Light mineral oil | 12.8 | 38.4 g |
| Aluminum stearate | 8.0 | 24.0 g |
| Cetyl alcohol | 4.0 | 12.0 g |
| WITCONOL™ 14[a] | 3.0 | 9.00 g |
| Acetylated lanolin | 1.0 | 3.0 g |
| Propylparaben | 0.063 | 0.19 g |
| Aqueous Phase | | |
| Oil Phase | | |
| VEEGUM™ K[b] | 1.0 | 3.0 g |
| Methylparaben | 0.12 | 0.36 g |
| Purified water | 49.017 | 147.05 g |

[a]WITCONOL™ 14 (polyglyceryl4 oleate) is available from Witco Chemical Corp. Organics Division
[b]VEEGUM™ K (colloidal magnesium aluminum silicate) is available from R. T. Vanderbilt Company Inc.

The materials listed above were combined according to the following procedure:

The 1-isobutyl-1H-imidazo[4,5-c]quinolin-4-amine and the isostearic acid were weighed into a glass jar and heated with occasional stirring until the amine was dissolved (the temperature reached 68° C.). To this solution was added, the petrolatum, mineral oil, aluminum stearate, cetyl alcohol, WITCONOL™ 14, acetylated lanoline and propylparaben. The mixture was heated to 75° C. In a separate beaker, the methylparaben and water were combined and heated until the paraben dissolved (the temperature reached 61° C.). The VEEGUM™ K was added to the aqueous solution and heated at 75° C. for 30 minutes while mixing with a homogenizer. With both phases at 75° C., the aqueous phase was slowly added to the oil phase while mixing with a homogenizer. Mixing was continued for 30 minutes while maintaining a temperature to about 80° C. The jar was then capped and the formulation was allowed to cool.

Example 11

An ointment according to this disclosure was prepared from the ingredients in the following Table 5:

TABLE 5

| Component | % by Weight | Amount |
|---|---|---|
| 1-isobutyl-1H-imidazo[4,5-c]quinolin-4-amine | 1.0 | 0.20 g |
| Isostearic acid | 5.0 | 1.00 g |
| Mineral oil | 12.8 | 2.56 g |
| White petrolatum | 65.2 | 13.04 g |
| Cetyl alcohol | 4.0 | 0.80 g |
| Acetylated lanolin | 1.0 | 0.20 g |
| WITCONOL™ | 143.0 | 0.60 g |
| Aluminum stearate | 8.0 | 1.60 g |

The materials listed above were combined according to the following procedure:

The 1-isobutyl-1H-imidazo[4,5-c]quinolin-4-amine and the isostearic acid were placed in a glass jar and heated with stirring until the amine was dissolved. The remaining ingredients were added and the resulting mixture was heated to 65° C. and then mixed while being allowed to cool to room temperature.

Example 12

Using the general procedure of Example 11 an ointment containing the ingredients in the following Table 6 was prepared:

TABLE 6

| Component | % by Weight | Amount |
| --- | --- | --- |
| 1-isobutyl-1H-imidazo[4,5-c]quinolin-4-amine | 1.0 | 0.20 g |
| Isostearic acid | 6.0 | 1.20 g |
| Polyethylene Glycol 400 | 55.8 | 11.16 g |
| Polyethylene Glycol 3350 | 32.6 | 6.52 g |
| Stearyl alcohol | 4.6 | 0.92 g |

Examples 13-15

Creams of this disclosure were prepared using the ingredients shown in Table 7 below following the procedure of Example 1, except that benzyl alcohol was used with the isostearic acid to dissolve the 1-isobutyl-1H-imidazo[4,5-c]quinolin-4-amine.

TABLE 7

| | Amount % by Weight | | |
| --- | --- | --- | --- |
| Component | Example 13 | Example 14 | Example 15 |
| Oil Phase | | | |
| 1-isobutyl-1H-imidazo[4,5-c]quinolin-4-amine | 5.0 | 5.0 | 4.85 |
| Isostearic acid | 25.0 | 25.0 | 24.3 |
| Benzyl alcohol | 2.0 | 2.0 | 1.94 |
| Cetyl alcohol | 2.2 | 2.2 | 1.16 |
| Stearyl alcohol | 3.1 | 3.1 | 1.75 |
| Petrolatum | 3.0 | 2.91 | |
| Polysorbate 60 | 3.4 | 3.4 | 4.13 |
| Sorbitan monostearate | 0.6 | 0.6 | 0.73 |
| Stearic acid | | | 9.71 |
| Aqueous Phase | | | |
| Glycerin | 2.0 | 2.0 | 1.94 |
| Methylparaben | 0.2 | 0.2 | 0.19 |
| Propylparaben | 0.02 | 0.02 | 0.02 |

Example 16

A cream according to this disclosure was prepared from the ingredients in the following Table 8:

TABLE 8

| Component | % by Weight | Amount |
| --- | --- | --- |
| Oil Phase | | |
| 1-isobutyl-1H-imidazo[4,5-c]quinolin-4-amine | 4.0 | 0.80 g |
| Isostearic acid | 20.0 | 4.00 g |
| Benzyl alcohol | 2.0 | 0.40 g |
| Cetyl alcohol | 2.2 | 0.49 g |
| Stearyl alcohol | 3.1 | 0.62 g |
| Polysorbate 60 | 3.4 | 0.68 g |
| Sorbitan monostearate | 0.6 | 0.12 g |
| Aqueous Phase | | |
| 1-isobutyl-1H-imidazo[4,5-c]quinolin-4-amine 1.0 | | 0.2 g |
| Glycerin | 2.0 | 0.4 g |
| 85% Lactic acid | 1.0 | 0.22 g |
| Methylparaben | 0.2 | 0.04 g |
| Propylparaben | 0.02 | 0.004 g |
| Purified water | 60.48 | 12.0 g |

The materials listed above were combined according to the following procedure:

The isostearic acid and 0.8 g of 1-isobutyl-1H-imidazo[4,5-c]quinolin-4-amine or 1-(2-methylpropyl)-1H-imidazo[4,5-c]quinolin-4-amine were combined in a glass jar and heated with stirring until the amine had dissolved. The remaining oil phase ingredients were added to this solution and the mixture was heated to about 70° C. The aqueous phase ingredients were weighed into a separate beaker and heated with stirring until the amine and the parabens had dissolved. With both phases at about 70° C., the water phase was added to the oil phase and mixed with a propeller until the mixture cooled to room temperature.

Example 17

A mixture of 5.9415 g of the 93:7 isooctyl acrylate:acrylamide adhesive copolymer prepared in PREPARATIVE METHOD 2 above, 1.5126 g isostearic acid, 2.0075 g ethyl oleate, 0.3021 g glyceryl monolaurate, 0.2936 g 1-isobutyl-1H-imidazo[4,5-c]quinolin-4-amine (micronized) and 23.7 g of 90:10 ethyl acetate:methanol was placed in a small glass jar. The jar was placed on a horizontal shaker and shaken at room temperature for about 13 hours. The formulation was coated at a thickness of 20 mils onto a 5 mil DAUBERT™ 164Z liner. The laminate was oven dried for 3 minutes at 105° F., for 2 minutes at 185° F., and for 2 minutes at 210° F. The resulting adhesive coating contained 59.1% 93:7 isooctyl acrylate:acylamide adhesive copolymer, 15.0% isostearic acid, 20.0% ethyl oleate, 3.0% glyceryl monolaurate and 2.9% 1-isobutyl-1H-imidazo[4,5-c]quinolin-4-amine. The material was then laminated with 3 mil low density polyethylene backing and die cut into 2.056 cm$^2$ patches.

Examples 18-20

Pressure-Sensitive Adhesive Coated Sheet Materials Prepared Using Unmicronized 1-isobutyl-1H-imidazo[4,5-c]quinolin-4-amine Using the general method of Example 17, the formulations shown below were prepared. 1-Isobutyl-1H-imidazo[4,5-c]quinolin-4-amine or 1-(2-methylpropyl)-1H-imidazo[4,5-c]quinolin-4-amine that had been ground with a mortar and pestle was used. The adhesive was the 93:7 isooctyl acrylate:acrylamide copolymer prepared in Preparative Method 1 above. The solvent was 90:10 ethyl acetate:methanol. All formulations in the following Table 9 were mixed at room temperature.

TABLE 9

| | Amount % by Weight | | |
| --- | --- | --- | --- |
| Component | Example 18 | Example 19 | Example 20 |
| 1-isobutyl-1H-imidazo[4,5-c]quinolin-4-amine | 5.0 | 3.0 | 3.0 |
| Ethyl oleate | 5.1 | 5.0 | 8.0 |
| Isostearic acid | 10.0 | 10.0 | 6.0 |
| Oleic acid | 20.0 | 20.0 | 13.0 |
| Glyceryl monolaurate | 1.5 | 1.5 | 1.5 |
| N,N-dimethyldodecylamine-N-oxide | 1.0 | 1.1 | 3.0 |
| Adhesive | 57.4 | 59.3 | 65.4 |

Example 21

A formulation with the same components in the same proportions as Example 18 was prepared using a different method. The 1-isobutyl-1H-imidazo[4,5-c]-quinolin-4-amine or 1-(2-methylpropyl)-1H-imidazo[4,5-c]quinolin-4-amine was combined with the oleic and isostearic acids and shaken at 40° C. until there was complete dissolution of the 1-isobutyl-1H-imidazo-[4,5-c]quinolin-4-amine or 1-(2-methylpropyl)-1H-imidazo[4,5-c]quinolin-4-amine. The remaining ingredients were added and shaken a 40° C. for 72 hours. Patches measuring 2.056 cm$^2$ were prepared by the general method of Example 17.

Example 22

A mixture of 2.4734 g 1-isobutyl-1H-imidazo[4,5-c]-quinolin-4-amine or 1-(2-methylpropyl)-1H-imidazo[4,5-c]quinolin-4-amine, 3.3315 g isostearic acid and 6.6763 g oleic acid is prepared. To 1.8738 g of the above mixture was added 2.8750 g of the 93:7 isooctyl acrylate:acryamide adhesive copolymer prepared in PREPARATIVE METHOD 2 above, 0.2548 g of ethyl oleate, 0.0510 g N,N-dimethyl-dodecylamine-N-oxide, 0.0820 g glyceryl monolaurate (from Lauricidin, Inc.) and 14.0457 g of 90:10 ethyl acetate/methanol. The above was shaken for 30 hours at room temperature on a horizontal shaker.

Example 23

Topical Imiquimod Pharmaceutical Cream Formulations

Creams are prepared in accordance with this disclosure using the ingredients shown in this Example 23. The materials listed below in this Example 23 are combined according to the following procedure to make cream formulations in the following Table 10 of this Example 23:

TABLE 10

Lower Dosage Strength Imiquimod Formulations

| Excipients | % w/w Formulation 1 | % w/w 2 | % w/w 3 | % w/w 4 | % w/w 5 | % w/w 6 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.98 | 66.98 | 64.98 | 61.98 | 60.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients | % w/w Formulation 7 | % w/w 8 | % w/w 9 | % w/w 10 | % w/w 11 | % w/w 12 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.98 | 60.98 | 60.98 | 57.08 | 58.98 | 55.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients | % w/w Formulation 13 | % w/w 14 | % w/w 15 | % w/w 16 | % w/w 17 | % w/w 18 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.48 | 67.08 | 59.98 | 58.98 | 56.98 | 61.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients | % w/w Formulation 19 | % w/w 20 | % w/w 21 | % w/w 22 | % w/w 23 | % w/w 24 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.73 | 66.73 | 64.73 | 61.73 | 60.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients | % w/w Formulation 25 | % w/w 26 | % w/w 27 | % w/w 28 | % w/w 29 | % w/w 30 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.73 | 60.73 | 60.73 | 56.83 | 58.73 | 55.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

TABLE 10-continued

Lower Dosage Strength Imiquimod Formulations

| Excipients | Formulation 31 % w/w | 32 % w/w | 33 % w/w | 34 % w/w | 35 % w/w | 36 % w/w |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.23 | 66.83 | 59.73 | 58.73 | 56.73 | 61.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients | Formulation 37 % w/w | 38 % w/w | 39 % w/w | 40 % w/w | 41 % w/w | 42 % w/w |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.48 | 66.48 | 64.48 | 61.48 | 60.23 | 60.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients | Formulation 43 % w/w | 44 % w/w | 45 % w/w | 46 % w/w | 47 % w/w | 48 % w/w |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.48 | 60.48 | 60.48 | 56.58 | 58.48 | 55.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients | Formulation 49 % w/w | 50 % w/w | 51 % w/w | 52 % w/w | 53 % w/w | 54 % w/w |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.98 | 66.58 | 59.48 | 58.48 | 56.48 | 61.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients | Formulation 55 % w/w | 56 % w/w | 57 % w/w | 58 % w/w | 59 % w/w | 60 % w/w |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.23 | 66.23 | 64.23 | 61.23 | 59.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients | Formulation 61 % w/w | 62 % w/w | 63 % w/w | 64 % w/w | 65 % w/w | 66 % w/w |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 6.00 | 6.00 | 3.00 | 5.00 | 3.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.23 | 60.23 | 60.23 | 56.33 | 58.23 | 55.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients | Formulation 67 % w/w | 68 % w/w | 69 % w/w | 70 % w/w | 71 % w/w | 72 % w/w |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.73 | 66.33 | 59.23 | 58.23 | 56.23 | 61.23 |
| Benzyl alcohol | 2.00 | 2.00 | 2.00 | 2.00 | 2.00 | 2.00 |

TABLE 10-continued

Lower Dosage Strength Imiquimod Formulations

| Excipients | % w/w | % w/w | % w/w | % w/w | % w/w | % w/w |
|---|---|---|---|---|---|---|
| | | | | | | |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients | Formulation 73 | 74 | 75 | 76 | 77 | 78 |
|---|---|---|---|---|---|---|
| Fatty acid* | 10.00 | 12.50 | 25.00 | 10.00 | 15.00 | 20.00 |
| Cetyl alcohol | 2.20 | 2.20 | 2.70 | 4.00 | 4.00 | 2.20 |
| Stearyl alcohol | 3.10 | 3.10 | 3.80 | 2.00 | 2.00 | 3.10 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.00 |
| Sorbitan Monostearate | 0.60 | 0.60 | 0.60 | 1.00 | 1.00 | 1.00 |
| Glycerin | 5.00 | 5.00 | 2.00 | 1.00 | 0.70 | 0.75 |
| Xantham gum | 0.50 | 0.50 | 0.50 | 0.30 | 0.70 | 0.75 |
| Purified water | 65.98 | 63.48 | 54.78 | 70.28 | 64.28 | 59.73 |
| Benyzl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients | Formulation 79 | 80 | 81 | 82 | 83 | 84 |
|---|---|---|---|---|---|---|
| Fatty acid* | 10.00 | 12.50 | 25.00 | 10.00 | 15.00 | 25.00 |
| Cetyl alcohol | 2.20 | 2.20 | 2.70 | 4.00 | 4.00 | 2.70 |
| Stearyl alcohol | 3.10 | 3.10 | 3.80 | 2.00 | 2.00 | 3.80 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.40 |
| Sorbitan Monostearate | 0.60 | 0.60 | 0.60 | 1.00 | 1.00 | 0.60 |
| Glycerin | 5.00 | 5.00 | 2.00 | 1.00 | 3.00 | 2.00 |
| Xanthan gum | 0.50 | 0.50 | 0.50 | 0.30 | 0.70 | 0.50 |
| Purified water | 65.98 | 63.48 | 54.78 | 70.28 | 64.28 | 54.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients | Formulation 85 | 86 | 87 | 88 | 89 | 90 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.48 | 66.08 | 58.98 | 57.98 | 55.98 | 60.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients | Formulation 91 | 92 | 93 | 94 | 95 | 96 |
|---|---|---|---|---|---|---|
| Fatty acid* | 15.00 | 12.50 | 25.00 | 15.00 | 10.00 | 20.00 |
| Cetyl alcohol | 2.20 | 2.20 | 2.20 | 2.00 | 2.00 | 2.20 |
| Stearyl alcohol | 3.10 | 3.10 | 3.10 | 2.00 | 2.40 | 3.10 |
| White petrolatum | 5.00 | 3.00 | 3.40 | 2.80 | 3.00 | 6.00 |
| Polysorbate 60 | 3.00 | 3.00 | 3.40 | 3.80 | 3.80 | 3.00 |
| Sorbitan Monostearate | 1.00 | 1.00 | 0.60 | 0.20 | 1.00 | 1.00 |
| Glycerin | 5.00 | 5.00 | 2.00 | 3.00 | 3.00 | 3.00 |
| Xanthan gum | 1.00 | 0.50 | 1.00 | 0.30 | 0.30 | 0.75 |
| Purified water | 60.23 | 63.23 | 55.23 | 66.83 | 70.23 | 59.48 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients | Formulation 97 | 98 | 99 | 100 | 101 | 102 |
|---|---|---|---|---|---|---|
| Fatty acid* | 15.00 | 12.50 | 25.00 | 15.00 | 10.00 | 25.00 |
| Cetyl alcohol | 2.20 | 2.20 | 2.20 | 2.00 | 2.00 | 2.70 |
| Stearyl alcohol | 3.10 | 3.10 | 3.10 | 2.00 | 2.40 | 3.80 |
| White petrolatum | 5.00 | 3.00 | 3.40 | 2.80 | 3.00 | 6.00 |
| Polysorbate 60 | 3.00 | 3.00 | 3.40 | 3.80 | 3.80 | 3.40 |
| Sorbitan Monostearate | 1.00 | 1.00 | 0.60 | 0.20 | 1.00 | 0.60 |
| Glycerin | 5.00 | 5.00 | 2.00 | 3.00 | 3.00 | 2.00 |
| Xanthan gum | 1.00 | 0.50 | 1.00 | 0.30 | 0.30 | 0.50 |
| Purified water | 60.23 | 63.23 | 55.23 | 66.83 | 70.23 | 54.53 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients | Formulation 103 | 104 | 105 | 106 | 107 | 108 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.23 | 65.83 | 58.73 | 57.73 | 55.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients | Formulation 109 | 110 | 111 | 112 | 113 | 114 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |

TABLE 10-continued

Lower Dosage Strength Imiquimod Formulations

| | | | | | | |
|---|---|---|---|---|---|---|
| White petrolatum | 3.00 | 2.00 | 3.00 | 6.00 | 3.00 | 2.50 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.98 | 65.48 | 63.48 | 60.48 | 59.23 | 59.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | | | Formulation | | | |
| Excipients | 115 | 116 | 117 | 118 | 119 | 120 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 6.00 | 6.00 | 3.00 | 5.00 | 3.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 65.48 | 59.48 | 59.48 | 55.58 | 57.48 | 54.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | | | Formulation | | | |
| Excipients | 121 | 122 | 123 | 124 | 125 | 126 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.98 | 65.58 | 58.48 | 57.48 | 55.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | | | Formulation | | | |
| Excipients | 127 | 128 | 129 | 130 | 131 | 132 |
| Fatty acid* | 15.00 | 18.00 | 15.00 | 20.00 | 12.50 | 20.00 |
| Cetyl alcohol | 2.00 | 2.00 | 2.00 | 2.00 | 2.20 | 2.20 |
| Stearyl alcohol | 2.00 | 2.00 | 2.40 | 2.40 | 3.10 | 3.10 |
| White petrolatum | 2.80 | 3.40 | 2.80 | 5.00 | 3.00 | 3.40 |
| Polysorbate 60 | 3.00 | 3.80 | 3.00 | 3.00 | 3.40 | 3.00 |
| Sorbitan Monostearate | 1.00 | 1.00 | 0.20 | 0.20 | 0.60 | 1.00 |
| Glycerin | 3.00 | 2.00 | 1.00 | 3.00 | 6.00 | 3.00 |
| Xanthan gum | 0.30 | 0.70 | 0.70 | 0.30 | 0.50 | 0.75 |
| Purified water | 65.08 | 62.48 | 67.08 | 61.08 | 61.48 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | | | Formulation | | | |
| Excipients | 133 | 134 | 135 | 136 | 137 | 138 |
| Fatty acid* | 15.00 | 18.00 | 15.00 | 20.00 | 12.50 | 25.00 |
| Cetyl alcohol | 2.00 | 2.00 | 2.00 | 2.00 | 2.20 | 2.70 |
| Stearyl alcohol | 2.00 | 2.00 | 2.40 | 2.40 | 3.10 | 3.80 |
| White petrolatum | 2.80 | 3.40 | 2.80 | 5.00 | 3.00 | 3.40 |
| Polysorbate 60 | 3.00 | 3.80 | 3.00 | 3.00 | 3.40 | 3.40 |
| Sorbitan Monostearate | 1.00 | 1.00 | 0.20 | 0.20 | 0.60 | 0.60 |
| Glycerin | 3.00 | 2.00 | 1.00 | 3.00 | 6.00 | 2.00 |
| Xanthan gum | 0.30 | 0.70 | 0.70 | 0.30 | 0.50 | 0.50 |
| Purified water | 65.08 | 62.48 | 67.08 | 61.08 | 61.48 | 53.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | | | Formulation | | | |
| Excipients | 139 | 140 | 141 | 142 | 143 | 144 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.48 | 65.08 | 57.98 | 56.98 | 54.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | | | Formulation | | | |
| Excipients | 145 | 146 | 147 | 148 | 149 | 150 |
| Fatty acid* | 15.00 | 20.00 | 15.00 | 20.00 | 10.00 | 0.00 |
| Cetyl alcohol | 2.00 | 2.00 | 4.00 | 4.00 | 2.20 | 2.20 |
| Stearyl alcohol | 2.00 | 2.40 | 2.40 | 2.40 | 3.10 | 3.10 |
| White petrolatum | 2.80 | 2.50 | 3.40 | 5.00 | 3.00 | 3.40 |
| Polysorbate 60 | 3.00 | 3.00 | 3.00 | 3.80 | 3.40 | 3.00 |
| Sorbitan Monostearate | 1.00 | 0.20 | 1.00 | 1.00 | 0.60 | 1.00 |
| Glycerin | 3.00 | 3.00 | 1.00 | 3.00 | 5.00 | 3.00 |
| Xanthan gum | 0.30 | 0.30 | 0.30 | 0.70 | 0.50 | 0.75 |
| Purified water | 64.83 | 60.83 | 65.33 | 57.23 | 64.73 | 58.48 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

TABLE 10-continued

Lower Dosage Strength Imiquimod Formulations

| Excipients | % w/w Formulation 151 | % w/w 152 | % w/w 153 | % w/w 154 | % w/w 155 | % w/w 156 |
|---|---|---|---|---|---|---|
| Fatty acid* | 15.00 | 20.00 | 15.00 | 20.00 | 10.00 | 25.00 |
| Cetyl alcohol | 2.00 | 2.00 | 4.00 | 4.00 | 2.20 | 2.70 |
| Stearyl alcohol | 2.00 | 2.40 | 2.40 | 2.40 | 3.10 | 3.80 |
| White petrolatum | 2.80 | 2.50 | 3.40 | 5.00 | 3.00 | 3.40 |
| Polysorbate 60 | 3.00 | 3.00 | 3.00 | 3.80 | 3.40 | 3.40 |
| Sorbitan Monostearate | 1.00 | 0.20 | 1.00 | 1.00 | 0.60 | 0.60 |
| Glycerin | 3.00 | 3.00 | 1.00 | 3.00 | 5.00 | 2.00 |
| Xanthan gum | 0.30 | 0.30 | 0.30 | 0.70 | 0.50 | 0.50 |
| Purified water | 64.83 | 60.83 | 65.33 | 57.23 | 64.73 | 53.53 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients | % w/w Formulation 157 | % w/w 158 | % w/w 159 | % w/w 160 | % w/w 161 | % w/w 162 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.23 | 64.83 | 59.98 | 56.73 | 54.73 | 59.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients | % w/w Formulation 163 | % w/w 164 | % w/w 165 | % w/w 166 | % w/w 167 | % w/w 168 |
|---|---|---|---|---|---|---|
| Fatty acid* | 15.00 | 10.00 | 12.50 | 19.00 | 20.00 | 20.00 |
| Cetyl alcohol | 2.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 5.00 | 5.00 | 3.00 | 3.00 | 3.00 | 3.40 |
| Polysorbate 60 | 3.00 | 3.40 | 4.00 | 3.40 | 3.40 | 3.00 |
| Sorbitan Monostearate | 0.20 | 0.60 | 0.60 | 0.60 | 0.60 | 1.00 |
| Glycerin | 1.00 | 4.00 | 5.00 | 2.00 | 6.00 | 3.00 |
| Xanthan gum | 0.70 | 0.50 | 0.50 | 0.50 | 0.50 | 0.75 |
| Purified water | 66.58 | 65.48 | 61.38 | 60.48 | 56.48 | 58.23 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients | % w/w Formulation 169 | % w/w 170 | % w/w 171 | % w/w 172 | % w/w 173 | % w/w 174 |
|---|---|---|---|---|---|---|
| Fatty acid* | 15.00 | 10.00 | 12.50 | 19.00 | 20.00 | 25.00 |
| Cetyl alcohol | 2.00 | 2.20 | 2.20 | 2.20 | 2.20 | 2.70 |
| Stearyl alcohol | 2.40 | 3.10 | 3.10 | 3.10 | 3.10 | 3.80 |
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.40 |
| Sorbitan Monostearate | 0.20 | 0.60 | 0.60 | 0.60 | 0.60 | 0.60 |
| Glycerin | 1.00 | 4.00 | 5.00 | 2.00 | 6.00 | 2.00 |
| Xanthan gum | 0.70 | 0.50 | 0.50 | 0.50 | 0.50 | 0.50 |
| Purified water | 66.58 | 65.48 | 61.38 | 60.48 | 56.48 | 53.28 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients | % w/w Formulation 175 | % w/w 176 | % w/w 177 | % w/w 178 | % w/w 179 | % w/w 180 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.98 | 64.58 | 57.48 | 56.48 | 54.48 | 59.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients | % w/w Formulation 181 | % w/w 182 | % w/w 183 | % w/w 184 | % w/w 185 | % w/w 186 |
|---|---|---|---|---|---|---|
| Fatty acid* | 20.00 | 20.00 | 25.00 | 18.75 | 20.00 | 21.25 |
| Cetyl alcohol | 4.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 2.80 | 3.00 | 3.00 | 5.00 | 5.00 | 3.75 |
| Polysorbate 60 | 3.00 | 3.40 | 3.40 | 3.00 | 3.40 | 3.40 |
| Sorbitan Monostearate | 1.00 | 0.60 | 0.60 | 1.00 | 0.60 | 0.60 |
| Glycerin | 1.00 | 2.00 | 2.00 | 5.00 | 5.00 | 5.00 |
| Xanthan gum | 0.30 | 0.50 | 0.50 | 0.50 | 0.50 | 0.50 |
| Purified water | 64.53 | 59.23 | 54.23 | 55.48 | 54.23 | 54.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients | % w/w Formulation 187 | % w/w 188 | % w/w 189 | % w/w 190 | % w/w 191 | % w/w 192 |
|---|---|---|---|---|---|---|
| Fatty acid* | 20.00 | 20.00 | 20.00 | 25.00 | 18.75 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 59.23 | 53.23 | 53.23 | 54.33 | 55.48 | 53.03 |
| Benzyl alcohol | 2.00 | 2.00 | 2.00 | 2.00 | 2.00 | 2.00 |

TABLE 10-continued

Lower Dosage Strength Imiquimod Formulations

| Excipients | % w/w Formulation 193 | 194 | 195 | 196 | 197 | 198 |
|---|---|---|---|---|---|---|
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients | % w/w Formulation 193 | 194 | 195 | 196 | 197 | 198 |
|---|---|---|---|---|---|---|
| Fatty acid* | 25.00 | 20.00 | 20.00 | 20.00 | 20.00 | 21.00 |
| Cetyl alcohol | 2.20 | 4.00 | 2.20 | 2.20 | 2.20 | 2.20 |
| Stearyl alcohol | 3.10 | 2.40 | 3.10 | 3.10 | 3.10 | 3.10 |
| White petrolatum | 3.00 | 3.40 | 5.00 | 3.00 | 5.00 | 5.00 |
| Polysorbate 60 | 3.40 | 3.80 | 3.40 | 3.40 | 3.40 | 3.40 |
| Sorbitan Monostearate | 0.60 | 1.00 | 0.60 | 0.60 | 0.60 | 0.60 |
| Glycerin | 2.00 | 3.00 | 2.00 | 5.00 | 5.00 | 5.00 |
| Xanthan gum | 1.00 | 0.70 | 0.50 | 0.50 | 0.50 | 0.50 |
| Purified water | 53.73 | 55.73 | 57.23 | 56.23 | 54.23 | 53.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients | % w/w Formulation 199 | 200 | 201 | 202 | 203 | 204 |
|---|---|---|---|---|---|---|
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients | % w/w Formulation 205 | 206 | 207 | 208 | 209 | 210 |
|---|---|---|---|---|---|---|
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients | % w/w Formulation 211 | 212 | 213 | 214 | 215 | 216 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.48 | 64.08 | 56.98 | 55.98 | 53.98 | 58.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients | % w/w Formulation 217 | 218 | 219 | 220 | 221 | 222 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.73 | 63.73 | 61.73 | 58.73 | 57.48 | 57.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients | % w/w Formulation 223 | 224 | 225 | 226 | 227 | 228 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 63.73 | 57.73 | 57.73 | 53.83 | 55.73 | 52.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients | % w/w Formulation 229 | 230 | 231 | 232 | 233 | 234 |
|---|---|---|---|---|---|---|
| Fatty acid* | 25.00 | 15.00 | 20.00 | 20.00 | 20.0 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |

TABLE 10-continued

Lower Dosage Strength Imiquimod Formulations

| | | | | | | |
|---|---|---|---|---|---|---|
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.20 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.23 | 63.83 | 56.73 | 55.73 | 53.73 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

*The Fatty acid referenced in this Table 9 can be, for example, linoleic acid (la), Stearic acid (sa), palmitic acid (pa), isostearic acid (isa), unrefined oleic acid, (uoa), refined oleic acid, such as SUPER REFINED ® oleic acid (roa), or mixtures thereof.

The work area, all vessels and equipment is initially cleaned prior to commencing manufacture. A 2 L glass container and paddle stirrer blade are placed onto a balance and the weight is recorded. The paddle is then removed from the vessel. The isostearic acid and benzyl alcohol are weighed directly into the 2 L glass container. The imiquimod is then weighed into the 2 L glass container and a spatula is used to ensure the imiquimod is wetted with the isostearic acid and benzyl alcohol mixture. The 2 L container is then heated in a water bath to about 55±5° C. while stirring with a Heidolph mixer (Note: aluminum foil is placed around the top of the vessel and the paddle for the mixer, to limit evaporation). The solution is visually inspected to confirm the imiquimod has fully dissolved prior to mixing with cetyl alcohol, stearyl alcohol, white petrolatum, polysorbate 60 and sorbitan monostearate. Cetyl alcohol, stearyl alcohol, white petrolatum, polysorbate 60 and sorbitan monostearate are then weighed directly into the 2 L container and mixing is continued at about 55±5° C. until the oil phase is completely in solution. Separately, about 2 L of water are placed into a beaker and heated to 55±5° C. while stirring with a magnetic follower. Briefly, about 500 ml of the heated water is transferred into a 1 L beaker and placed into the water bath maintained at about 55±5° C. Half of the amount of glycerin required for the final formulation is then weighed into the beaker along with the total amount of methylparaben and propylparaben to the water (where both methyl and propyl paraben are weighed into weighing boats first, a pipette is used to remove a portion of the heated water to wash out the weighing boats to ensure total transfer of both the propyl- and methylparaben into the aqueous phase). The mixture is continuously stirred at about 55±5° C. (this is the aqueous phase). The remaining glycerin is then added to a 28 ml vial and the xanthan gum is added and mixed using a small overhead mixer (IKA®-Werke Lab Egg) with paddle attachment for about 10 min. The glycerin and xanthan mixture are then added slowly into the vortex of the aqueous phase, and a further aliquot of about 20 ml of heated water is used to rinse the vessel out into the water phase to ensure complete transfer. The water phase is then heated and mixed at about 55±5° C. until the xanthan gum mixture is fully and evenly dispersed into the aqueous phase. The temperatures of both the water phase and oil phase are both maintained at about 55±5° C. The aqueous phase is then transferred into the oil phase and the speed of the Heidolph mixer is increased during addition. The mixture is then homogenized on high speed for about 3 min and transferred immediately back to the Heidolph mixture; however, the contents of the homogenized sample, about 2 L, are mixed at about room temperature and allowed to cool to about 35° C. The container and contents and the paddle from the overhead mixer are then re-weighed and the weight of the paddle and 2 L beaker, as determined above, are subtracted to determine the total weight of the formulation remaining. The total weight (about 1 kg) of the cream is then made up to weight with heated water (Note: water evaporated during heating, which needs to be corrected at this point). The mixture is then transferred back onto the Heidolph mixer at about room temperature and mixed until the temperature of the formulation is below about 28° C. The lid of the container is then placed onto the vessel and stored at room temperature.

The lower dosage strength formulations of this Example 23 are believed to be stable and consistent with the specifications for the commercially available ALDARA 5% imiquimod cream. The lower dosage strength formulations of this Example 23, especially as to those lower dosage strength formulations wherein the vehicle comprises an isostearic acid as the fatty acid, are believed to have the following:

(1) Stability. The imiquimod formulations of this disclosure, when they are measured on HPLC at 25° C./60% RH, 30° C./65% RH and 40° C./75% RH over, one, two, three and six months, demonstrate stability consistent with the ALDARA 5% imiquimod cream;

(2) Degradation Products. No degradation products are detected in the formulations of this disclosure, at its current recommended storage temperatures of about 4-25° C. In addition, there are no degradation products detected at any of the temperatures or time points mentioned under "Stability" above, when analyzed at about 318 nm wavelength;

(3) Homogeneity. The amount of imiquimod that is recovered from the formulations at any of the above-mentioned temperatures and time points is between about 90 to about 110% w/w thereby demonstrating good homogeneity;

(4) Benzyl Alcohol Content. The formulations of this disclosure are also within specifications for the ALDARA 5% imiquimod cream, i.e., between 1.0% (w/w) and 2.1% (w/w), at any of the above-mentioned temperatures and time points as to benzyl alcohol content.

(5) Microscopic Stability. There is no change in the particle size and no crystals are detected in the formulations of this disclosure when they are stored at 25° C./60% RH and analyzed over a six month period;

(6) Macroscopic Stability. There are no obvious physical changes in the formulations of this disclosure when they are stored at 25° C./60% RH and analyzed over a six month period;

(7) Viscosity. The formulations of this disclosure are within the range of the specifications for the ALDARA 5% imiquimod cream, i.e., between 2000 cPs and 35,000 cps, when they are stored at 25° C./60% RH and analyzed over a six month period;

(8) pH Stability. The formulations of this disclosure are within the range of the specifications for the ALDARA 5% imiquimod cream, i.e., between pH 4.0 and pH 5.5, when they are stored at 25° C./60% RH and analyzed over a six month period;

(9) Preservative Efficacy Test ("PET"). The formulations of this disclosure demonstrate sufficient reductions in colony forming unit counts for each of the organisms with which the formulations are inoculated, i.e., S. aureus, E. coli, Ps. Aeruginosa, C. albicans, and A. niger, at 2-80° C. and 40° C. over a 28 day test period and meet the requirements specified in both the USP and EP;

(10) Imiquimod In vitro Release. The ALDARA 5% imiquimod cream releases statistically significant (p<0.05)

higher amounts of imiquimod over a 3 hour time period in comparison to the lower dosage strength formulations of this disclosure through a synthetic membrane, e.g., Microporous polyethylene film 3M No. 9711 COTRAN™. There is no statistical difference (p<0.05) in the total cumulative amount of imiquimod that is released from any of the 3.75% (w/w) imiquimod formulations. There is no statistical difference (p<0.05) in the total cumulative amount of imiquimod that is released from any of the 2.5% (w/w) imiquimod formulations. The ALDARA 5% imiquimod cream also statistically significantly (p<0.05) releases imiquimod at a faster rate over a 3 hour time period in comparison to the lower dosage strength formulations of this disclosure through a synthetic membrane, e.g., Microporous polyethylene film 3M No. 9711 COTRAN™. There is no statistical difference (p<0.05) between the imiquimod release rates for any of the 3.75% (w/w) imiquimod formulations. There is no statistical difference (p<0.05) between the imiquimod release rates for any of the 2.5% (w/w) imiquimod formulations. Thus, the greater the amount of imiquimod in a formulation, the faster and greater the total amount of imiquimod that is released from such formulation that the amount and rate of release of imiquimod are concentration dependent and that the rates and amounts of release of imiquimod from the formulations of this disclosure are linear and dose proportionate to the ALDARA 5% imiquimod cream;

(11) Imiquimod In vitro Skin Permeation (Franz Cell Study). With respect to statistical analyses, there is no statistical difference between the lower dosage strength formulations of this disclosure and the ALDARA 5% imiquimod cream as to the amount of imiquimod recovered from the receiver fluid, epidermis and dermis combined. Nonetheless, there is a statistically significant (p<0.05) dose proportionate difference between the amount of imiquimod recovered from each of the matrices with respect to the concentration of imiquimod in the lower dosage strength formulations of this disclosure and the ALDARA 5% imiquimod cream for both unabsorbed and stratum corneum. Thus there is a linear dose release between the amount of imiquimod that is applied and recovered in each of the matrices, i.e., receiver fluid, unabsorbed dose, stratum corneum, epidermis and dermis.

Methods for physically characterizing the properties of lower dosage strength imiquimod formulations described herein, and for testing lower dosage strength imiquimod formulations as described herein, can be performed as described in U.S. Patent Publication No. 2011/0319811, the entire contents of which are incorporated herein by reference.

Example 24

Four Phase 3 Randomized, Double-Blinded, Multicenter, Placebo-Controlled Clinical Studies This example describes Four Phase 3 randomized, double-blinded, multicenter, placebo-controlled clinical studies comparing the efficacy and safety of a 3.75% imiquimod cream of Example 23 and a 2.5% imiquimod cream of Example 23 to placebo in the treatment of typical visible or palpable actinic keratoses of the face or balding scalp. Subjects who were determined to be eligible during the screening phase were randomized in a 1:1:1 ratio to receive either 2.5% imiquimod cream, 3.75% imiquimod cream, or placebo cream once daily during the treatment cycles. The objective of the studies was to compare the safety and efficacy of 2.5% imiquimod cream and 3.75% imiquimod cream vs. placebo in the treatment of actinic keratosis when the cream was applied once daily for two 2-week treatment cycles separated by a 2-week no-treatment period.

Study Design

An overview of the procedures for GW01-0702, GW01-0703, GW01-0704, and GW01-0705 are described herein, and are also described in U.S. application Ser. No. 13/168,796, the entire contents of which are incorporated by reference herein in their entirety.

Studies GW01-0702 and GW01-0704 were duplicative studies that investigated 2-week treatment cycles, wherein the 2-week treatment cycles were separated by a two week non-treatment period (2×2×2), and studies GW01-0703 and GW01-0705 were duplicative studies that investigated 3-week treatment cycles, wherein the 3-week treatment cycles were separated by a three week non-treatment period (3×3×3). The study entry criteria and endpoints were identical in all four studies. Studies GW01-0702 and GW01-0704: two identical studies evaluated 2.5% imiquimod cream, 3.75% imiquimod cream, or placebo which was applied daily for two 2-week treatment cycles. The first treatment cycle consisted of two weeks of daily treatment followed by two weeks of no treatment, and the second treatment cycle consisted of an additional two weeks of daily treatment followed by eight weeks of post-treatment follow-up period (total study duration of 14 weeks). Studies GW01-0703 and GW01-0705: two identical studies evaluated 2.5% imiquimod cream, 3.75% imiquimod cream, or placebo which was applied daily for two 3-week treatment cycles. The first treatment cycle consisted of three weeks of daily treatment followed by three weeks of no treatment, and the second treatment cycle consisted of an additional three weeks of daily treatment followed by eight weeks of post-treatment follow-up period (total study duration of 17 weeks).

Studies GW01-0702 and GW01-0704 were conducted concurrently, at separate study sites, according to identical protocols. A total of approximately 479 subjects were randomized in a 1:1:1 ratio (approximately 240 to each treatment arm, i.e., 2.5% imiquimod cream, 3.75% imiquimod cream, and placebo cream) to achieve approximately 450 subjects completing the study. Eligible subjects for the study were at least 18 years of age, with about 5 to 20 typical visible or palpable actinic keratosis lesions (AKs) in an area that exceeded 25 cm$^2$ on either the face or the balding scalp. The treatment area could be either the entire face, excluding the ears, or the balding scalp, but not both. Apart from the primary diagnosis, the subjects were to be in good general health, and free of conditions which might put them at undue risk during study procedures. They must not use imiquimod cream on the face or scalp within 1 year of study entrance, nor use other potentially interfering medications within pre-specified washout intervals prior to study entrance.

The randomized, blinded study product was used in 2 treatment cycles each of 2 weeks duration, separated by a 2-week non-treatment period. Once a day during the treatment cycles, subjects applied the study cream in a thin layer to the entire treatment area. A maximum of 2 packets (i.e., up to 500 mg) could be applied for a given dose. The study cream was applied prior to normal sleeping hours and was removed approximately 8 hours later with mild soap and water.

During the 2 treatment cycles of 2 weeks, subjects were scheduled for a total of 9 study visits: visit 1—screening; visit 2—baseline, cycle 1 treatment initiation; visit 3—week 1; visit 4—week 2, end of cycle 1; visit 5—week 4, cycle 2 treatment initiation; visit 6—week 5; visit 7—week 6, end of cycle 2 (end of treatment); visit 8—week 10, follow up; and visit 9—week 14, end of study, primary efficacy endpoint.

The two additional Phase 3 studies, GW01-0703 and GW01-070, were conducted concurrently according to identical protocols. These studies were also randomized, double-blind, multicenter, placebo-controlled trials identical to the pivotal studies in all respects except for the duration of the treatment regimens and corresponding differences in visit schedules. The planned number of subjects, randomization methodology, entrance criteria, and study drug formulations were the same as in the two Phase 3 GW01-0702 and GW01-0704 studies trials. As in the GW01-0702 and GW01-0704 studies, the randomized, blinded study products were used in 2 treatment cycles, but in GW01-0703 and GW01-0705, the treatment cycles were of three weeks' duration, separated by a 3-week non-treatment period.

Thus, two pairs of 2 identical Phase 3 studies (four studies total) regarding efficacy and safety of four and six weeks of treatment with imiquimod formulations for actinic keratosis were conducted. Each pair evaluated a different treatment regimen and each individual study contained two imiquimod concentrations, i.e., 2.5% and 3.75% imiquimod formulations with comparisons to placebo (double-blinded).

The total population for the combined studies is summarized in Table 11 below:

TABLE 11

Population for Phase 3 studies GW01-0702, GW01-0703, GW01-0704, and GW01-0705

| | L2 2.5% 2 W (N = 160) | H2 3.75% 2 W (N = 160) | L3 2.5% 3 W (N = 164) | H 3.75% 3 W (N = 162) | V Vehicle (N = 323) |
|---|---|---|---|---|---|
| Age, Mean (Range) | 64 (39-90) | 64 (36-89) | 66 (33-87) | 64 (40-90) | 64 (37-89) |
| Sex, % male | 79 | 83 | 78 | 76 | 82 |
| Race % white | 100 | 100 | 100 | 99 | 99 |
| Treatment Area, % Face/Scalp | 73/27 | 76/2 | 70/30 | 71/2 | 75/25 |
| Skin Type, % I, II, and III | 84 | 87 | 88 | 90 | 86 |
| Baseline Count, Mean/Median | 10.9/10.0 | 11.01/10.0 | 10.6/10.0 | 11.1/9.0 | 10.8/10.0 |

The following efficacy and safety results were observed, as shown in FIG. 1: (1) all active treatment groups showed statistically significant differences from vehicle in all efficacy measures; and (2) there were no consistent statistically significant differences between the 2.5% and 3.75% treatment groups (*) with each of the studies. (*) Partial clearance was significantly different between L2 and H2 in the GW01-0704 study, but not in the GW01-0702 study; (*) Percent reduction between L2 and H2 in PP GW01-0704 study and PP GW01-0702 study, not in ITT population; (*) Percent reduction between L3 and H3 in PP GW01-0705 study, not in ITT population and not in GW01-0703 study. For this study, the primary population to be analyzed for efficacy and safety was the "ITT" (Intent-to-Treat) population, including all randomized subjects. The "PP" (Per Protocol) population included subjects who complete the study without any protocol violations. Subjects were excluded from the PP population if any of the following criteria are met: failure to meet inclusion/exclusion criteria; taking restricted medications/treatments; nonadherence to the visit schedule; or noncompliance with study treatment.

Analysis

AK lesions were counted at study visits to derive the one primary (Complete Clearance) and two secondary (Partial Clearance, Percent AK reduction) efficacy endpoints. To meet the Complete Clearance primary efficacy endpoint, subjects needed to be clear of all lesions in the treatment area, irrespective of whether those lesions were identified at baseline or later.

The primary efficacy variable was subject status with respect to complete clearance of AK lesions at the end of the study (EOS; 8 weeks following the last scheduled dose). The EOS visits occurred at Week 14 for the GW01-0702/GW01-0704 studies, and at Week 17 for the GW01-0703/GW01-0705 studies. Complete clearance was defined as the absence of clinically visible or palpable AK lesions in the treatment area.

The secondary efficacy variables were: subject status with respect to partial clearance of AK lesions at EOS, defined as at least about a 75% reduction in the number of AK lesions in the treatment area compared with baseline; and percent change (reductions) from baseline to EPS in investigator counts of AK lesions. The statistical methods for efficacy analysis were the same in all four Phase 3 studies.

Efficacy analysis was conducted on the ITT population and on the PP population. For the primary efficacy variable, imputations were made for missing data points using last observation carried forward (LOCF, primary analysis), taking all missed observations as failure (sensitivity analysis), and using observed cases only (supportive analysis). The PP population analysis used only cases that were observed. For analysis of secondary efficacy variables, only the LOCF method was used for the ITT population, and only cases that were observed for the PP population. All data from interim visits (before EOS/Early Termination) were analyzed at their nominal time points. The allowed visit window at EOS was any time more than 42 days after the data of last dose (or last rest). Subjects with no EOS visit were excluded from the PP population. In the ITT population, subjects without an in-window EOS visit were analyzed using the LOCF.

All pairwise comparisons of active treatment versus placebo were made using Hochberg's modified Bonferroni procedure. If either test was significant at a 0.025 level of significance, then that test was considered significant. Otherwise, if both tests were significant at 0.05, then both tests were considered significant. The 3.75% and 2.5% imiquimod treatment groups were compared to each other at the 0.05 level of significance if at least one of these treatment groups was found to be different than the placebo using the Hochberg's test.

In this way, complete clearance rates, partial clearance rates, change from baseline AK lesion counts, and percent change from baseline AK lesion counts were analyzed using Cochran-Mantel-Haenszel (CMH) statistics, stratifying on center.

If at least one of the active arms was found to be superior to placebo in the primary efficacy variable of complete clearance, the secondary efficacy variable of partial clearance was compared between each of the active arms and placebo using Hochberg's modified Bonferroni procedure. If the secondary efficacy variable of partial clearance was found to be superior to placebo in either of the active treatment groups, then the secondary efficacy variable of percent reduction was tested. Tertiary efficacy variables were tested without adjustment for multiplicity at the nominal 5% level.

In order to obtain at least 6 subjects per center per treatment group, investigational centers yielding fewer than 18 subjects were combined together in order of geographical proximity. The exact composition of these "analysis centers" was determined and documents prior to breaking the study blind. The stratification for CMH analyses was based on the analysis centers, not on the actual investigational centers.

In the primary analysis of complete clearance rate, the Breslow-Day statistic was tested at the 10% level for heterogeneity of the odds ratios across analysis centers. A finding of statistical significance in this test was followed by exploratory analyses to characterize the source of the heterogeneity.

The primary efficacy variable was summarized without statistical testing by success frequency by investigator center, by analysis center, by gender, by age subgroup, by skin type subgroup, by baseline lesion count subgroup, and by treatment area (face or balding scalp).

Subjects who showed a greater number of AK lesions at any time post-baseline compared to the baseline lesion count were of particular interest since the new lesions might represent sub-clinical lesions which are present but unobserved at the baseline visit. The proportion of subjects who show new lesions while on treatment are presented by treatment group, and the primary efficacy variable is summarized in this subject subgroup.

Results

The preliminary results from each of the Phase 3 clinical studies are summarized in the sections below, with the results of paired identical studies (GW01-0702/GW01-0704 and GW01-0703/GW01-0705) presented side by side. Overall, a total of 969 subjects were enrolled in the four Phase 3 studies. 51 independent sites in the United States enrolled subjects in the studies.

Two-Week Treatment Cycle Studies

Preliminary data from studies GW01-0702 and GW01-0704 are presented below. Subject demographics for each study are shown in Table 12, and the number of baseline AK lesions for each study is shown in Table 13.

TABLE 12

Demographic summary - 2-week treatment cycle regimen studies (ITT population)

| | GW01-0702 | | | GW01-0704 | | |
|---|---|---|---|---|---|---|
| | 2.5% IMIQ (N = 81) | 3.75% IMIQ (N = 81) | Placebo (N = 80) | 2.5% IMIQ (N = 79) | 3.75% IMIQ (N = 79) | Placebo (N = 79) |
| Age in years | | | | | | |
| Mean ± SD | 63.7 ± 10.7 | 63.8 ± 11.1 | 63.6 ± 8.3 | 65.0 ± 10.3 | 65.3 ± 10.0 | 65.0 ± 9.5 |
| Median | 63.3 | 63.9 | 63.4 | 64.4 | 65.3 | 63.7 |
| Minimum, Maximum | 43.8, 88.7 | 36.5, 89.8 | 42.7, 83.1 | 39.6, 90.0 | 36.3, 86.4 | 46.4, 89.1 |
| Sex, n (%) | | | | | | |
| Male | 59 (72.8) | 69 (85.2) | 70 (87.5) | 68 (86.1) | 63 (79.7) | 60 (75.9) |
| Female | 22 (27.2) | 12 (14.8) | 10 (12.5) | 11 (13.9) | 16 (20.3) | 19 (24.1) |
| Race, n (%) | | | | | | |
| White | 81 (100) | 81 (100) | 80 (100) | 79 (100) | 79 (100) | 78 (98.7) |
| Non-White | 0 | 0 | 0 | 0 | 0 | 1 (1.3) |
| Ethnicity, n (%) | | | | | | |
| Hispanic | 4 (4.9) | 5 (6.2) | 5 (6.3) | 0 | 1 (1.3) | 0 |
| Non-Hispanic | 77 (95.1) | 76 (93.8) | 75 (93.8) | 79 (100) | 78 (98.7) | 79 (100) |
| Fitzpatrick skin type, n (%) | | | | | | |
| I | 9 (11.1) | 5 (6.2) | 6 (7.5) | 20 (25.3) | 17 (21.5) | 13 (16.5) |
| II | 35 (43.2) | 43 (53.1) | 25 (31.3) | 27 (34.2) | 31 (39.2) | 33 (41.8) |
| III | 23 (28.4) | 17 (21.0) | 37 (46.3) | 20 (25.3) | 26 (32.9) | 26 (32.9) |
| IV | 11 (13.6) | 15 (18.5) | 11 (13.8) | 11 (13.9) | 5 (6.3) | 5 (6.3) |
| V | 3 (3.7) | 1 (1.2) | 1 (1.3) | 1 (1.3) | 0 | 2 (2.5) |
| Location of Treatment Area, n % | | | | | | |
| Face | 61 (75.3) | 66 (81.5) | 60 (75.0) | 56 (70.9) | 55 (69.9) | 59 (74.7) |
| Balding Scalp | 20 (24.7) | 15 (18.5) | 20 (25.0) | 23 (29.1) | 24 (30.4) | 20 (25.3) |

SD = standard deviation;
IMIQ = imiquimod

Fitzpatrick skin type: I = burns easily, never tans; II = burns easily, tans minimally with difficulty; III = burns moderately, tans moderates and uniformly; IV = burns minimally, tans moderately and evenly; V = rarely burns, tans profusely; VI = never burns, tans profusely.

TABLE 13

Actinic keratosis lesions at baseline - 2-week treatment cycle regimen studies (ITT population)

| Baseline values | GW01-0702 | | | GW01-0704 | | |
|---|---|---|---|---|---|---|
| | 2.5% IMIQ (N = 81) | 3.75% IMIQ (N = 81) | Placebo (N = 80) | 2.5% IMIQ (N = 79) | 3.75% IMIQ (N = 79) | Placebo (N = 79) |
| Mean (SD) | 11.11 (4.42) | 10.89 (4.90) | 11.74 (4.77) | 10.77 (4.44) | 11.16 (4.81) | 10.82 (4.64) |
| Median | 10 | 9 | 10 | 10 | 11 | 10 |
| Minimum, Maximum | 5, 20 | 5, 20 | 5, 20 | 5, 20 | 5, 29 | 5, 20 |
| P value vs Placebo[a] | 0.376 | 0.256 | NA | 0.864 | 0.542 | NA |
| P value vs 3.75% imiquimod[a] cream | 0.818 | NA | NA | 0.688 | NA | NA |

SD = standard deviation
[a]P values are from Cochran-Mantel-Haenszel test, are stratified by investigator center, taking 2 treatment groups at a time.

Subjects in studies GW01-0702 and GW01-0704 were compliant with the administration of study medication; greater than 91% of subjects were compliant with the dosing regimen. Compliance was defined as applying more than 75% of the prescribed doses; "rest" days were considered as application days.

Primary and secondary efficacy results for the GW01-0702 and GW01-0704 studies are presented in Table 14, Table 15, and Table 16. The primary efficacy variable was the rate of complete clearance at EOS (Week 14). The secondary efficacy variables were the rate of partial clearance (at least 75% reduction in AKs from baseline) at EOS, and the percent change from baseline to EOS in investigator counts of AK lesions. Both active treatment arms demonstrated greater efficacy than placebo, which was statistically significant for all primary and secondary endpoints.

TABLE 14

ITT (LOCF) complete clearance rates at EOS for individual 2-week treatment cycle regimen studies

| Study | 3.75% IMIQ | 2.5% IMIQ | Placebo |
|---|---|---|---|
| GW01-0702 | 25.9% (21/81) | 23.5% (19/81) | 2.5% (2/80) |
| GW01-0704 | 45.6% (36/79) | 38.0% (30/79) | 10.1% (8/79) |
| Combined | 35.6% (57/160) | 30.6% (49/160) | 6.3% (10/159) |

TABLE 15

ITT (LOCF) partial clearance rates at EOS for individual 2-week treatment cycle regimen studies

| Study | 3.75% IMIQ | 2.5% IMIQ | Placebo |
|---|---|---|---|
| GW01-0702 | 45.7% (37/81) | 42.0% (34/81) | 18.8% (15/80) |
| GW01-0704 | 73.4% (58/79) | 54.4% (43/79) | 26.6% (21/79) |
| Combined | 59.4% (95/160) | 48.1% (77/160) | 22.6% (36/159) |

TABLE 16

ITT (LOCF) median percent change from baseline in AK lesion count at EOS for individual 2-week treatment cycle regimen studies

| Study | 3.75% IMIQ | 2.5% IMIQ | Placebo |
|---|---|---|---|
| GW01-0702 | −72.7% | −60.0% | −21.1% |
| GW01-0704 | −90.9% | −76.5% | −30.0% |
| Combined | −81.8% | −71.8% | −25.0% |

In the two-week treatment cycle regimen studies, both 2.5% and 3.75% imiquimod creams demonstrated substantial efficacy for the treatment of AKs that was consistently significantly higher than that of placebo cream, with a trend towards greater efficacy in the 3.75% group. Both products were well-tolerated as evidenced by measures of adverse events, ability of subjects to remain in the study, incidence of rest periods, and compliance with study regimen (data not shown). Both active products resulted in increases in local skin reactions versus the placebo cream. For both active creams, the LSRs rapidly reduced with the completion of each treatment cycle and these LSRs were associated with relatively few reported application site reactions.

Three-Week Treatment Cycle Studies

Preliminary data from studies GW01-0703 and GW01-0705 are presented below. Subject demographics for each study are shown in Table 17, and the number of baseline AK lesions for each study is shown in Table 18.

TABLE 17

Demographic summary - 3-week treatment cycle regimen studies (ITT population)

| | | GW01-0703 | | | GW01-0705 | | |
|---|---|---|---|---|---|---|---|
| | | 2.5% IMIQ (N = 82) | 3.75% IMIQ (N = 80) | Placebo (N = 78) | 2.5% IMIQ (N = 82) | 3.75% IMIQ (N = 82) | Placebo (N = 86) |
| Age in years | | | | | | | |
| Mean ± SD | | 65.7 ± 10.4 | 64.5 ± 10.8 | 63.0 ± 10.1 | 66.4 ± 10.0 | 64.1 ± 9.7 | 64.4 ± 11.5 |
| Median | | 66.7 | 64.0 | 63.6 | 65.9 | 63.7 | 65.8 |

TABLE 17-continued

Demographic summary - 3-week treatment cycle regimen studies (ITT population)

| | GW01-0703 | | | GW01-0705 | | |
|---|---|---|---|---|---|---|
| | 2.5% IMIQ (N = 82) | 3.75% IMIQ (N = 80) | Placebo (N = 78) | 2.5% IMIQ (N = 82) | 3.75% IMIQ (N = 82) | Placebo (N = 86) |
| Minimum, Maximum | 85.3, 3.3 | 40.3, 85.5 | 39.8, 83.8 | 45.4, 87.3 | 90.9, 41.6 | 37.9, 87.0 |
| Sex, n (%) | | | | | | |
| Male | 62 (75.6) | 63 (78.8) | 63 (80.8) | 66 (80.5) | 60 (73.2) | 72 (83.7) |
| Female | 20 (24.4) | 17 (21.3) | 15 (19.2) | 16 (19.5) | 22 (26.8) | 14 (16.3) |
| Race, n (%) | | | | | | |
| White | 82 (100) | 78 (97.5) | 77 (98.7) | 82 (100.0) | 82 (100.0) | 86 (100.0) |
| Non-White | 0 | 2 (2.5) | 1 (1.3) | 0 | 0 | 0 |
| Ethnicity, n (%) | | | | | | |
| Hispanic | 2 (2.4) | 1 (1.3) | 0 (0.0) | 6 (7.3) | 6 (7.3) | 6 (7.0) |
| Non-Hispanic | 80 (97.6) | 79 (98.8) | 78 (100) | 76 (92.7) | 76 (92.7) | 80 (93.0) |
| Fitzpatrick skin type, n (%) | | | | | | |
| I | 8 (9.8) | 11 (13.8) | 11 (14.1) | 12 (14.6) | 11 (13.4) | 12 (14.0) |
| II | 35 (42.7) | 31 (38.8) | 28 (35.9) | 28 (34.1) | 47 (57.3) | 39 (45.3) |
| III | 28 (34.1) | 24 (30.0) | 26 (33.3) | 33 (40.2) | 21 (25.6) | 23 (26.7) |
| IV | 9 (11.0) | 13 (16.3) | 10 (12.8) | 8 (9.8) | 3 (3.7) | 9 (10.5) |
| V | 2 (2.4) | 1 (1.3) | 3 (3.8) | 1 (1.2) | 0 | 3 (3.5) |
| Location of Treatment Area, n (%) | | | | | | |
| Face | 63 (76.8) | 54 (67.5) | 60 (76.9) | 52 (63.4) | 61 (74.4) | 62 (72.1) |
| Balding Scalp | 19 (23.2) | 26 (32.5) | 18 (23.1) | 30 (36.6) | 21 (25.6) | 24 (27.9) |

SD = standard deviation;
IMIQ = imiquimod
Fitzpatrick skin type: I = burns easily, never tans; II = burns easily, tans minimally with difficulty; III = burns moderately, tans moderates and uniformly; IV = burns minimally, tans moderately and evenly; V = rarely burns, tans profusely; VI = never burns, tans profusely

TABLE 18

Actinic keratosis lesions at baseline - 3-week treatment cycle regimen studies (ITT population)

| | GW01-0703 | | | GW01-0705 | | |
|---|---|---|---|---|---|---|
| Baseline values | 2.5% IMIQ (N = 82) | 3.75% IMIQ (N = 80) | Placebo (N = 78) | 2.5% IMIQ (N = 82) | 3.75% IMIQ (N = 82) | Placebo (N = 86) |
| Mean (SD) | 10.74 (4.45) | 11.99 (5.47) | 11.24 (4.70) | 10.43 (4.05) | 10.26 (4.12) | 9.49 (3.67) |
| Median | 10 | 11 | 10 | 9 | 9 | 8 |
| Minimum, Maximum | 5, 20 | 5, 23 | 5, 20 | 5, 20 | 5, 20 | 5, 20 |
| P value vs Placebo[a] | 0.408 | 0.359 | NA | 0.094 | 0.197 | NA |
| P value vs 3.75% imiquimod cream[a] | 0.113 | NA | NA | 0.776 | NA | NA |

SD = standard deviation
[a] P values are from Cochran-Mantel-Haenszel test, are stratified by investigator center, taking 2 treatment groups at a time.

Subjects in studies GW01-0703 and GW01-0705 were compliant with the administration of study medication; greater than 92% of subjects were compliant with the dosing regimen. Compliance was defined as applying more than 75% of the prescribed doses; "rest" days were considered as application days.

Primary and secondary efficacy results for the GW01-0703 and GW01-0705 studies are presented in Table 19, Table 20, and Table 21. The primary efficacy variable was the rate of complete clearance at EOS (Week 17). The secondary efficacy variables were the rate of partial clearance (at least 75% reduction in AKs from baseline) at EOS, and the percent change from baseline to EOS in investigator counts of AK lesions. Both active treatment arms demonstrated greater efficacy than placebo, which was statistically significant for all primary and secondary endpoints.

TABLE 19

ITT (LOCF) complete clearance rates at EOS for individual 3-week treatment cycle regimen studies

| Study | 3.75% IMIQ | 2.5% IMIQ | Placebo |
| --- | --- | --- | --- |
| GW01-0703 | 32.5% (26/80) | 23.2% (19/82) | 5.1% (4/78) |
| GW01-0705 | 35.4% (29/82) | 26.8% (22/82) | 5.8% (5/86) |
| Combined | 34.0% (55/162) | 25% (41/164) | 5.5% (9/164) |

TABLE 20

ITT (LOCF) partial clearance rates at EOS for individual 3-week treatment cycle regimen studies

| Study | 3.75% IMIQ | 2.5% IMIQ | Placebo |
| --- | --- | --- | --- |
| GW01-0703 | 56.3% (45/80) | 46.3% (38/82) | 11.5% (9/78) |
| GW01-0705 | 51.2% (42/82) | 39.0% (32/82) | 14.0% (12/86) |
| Combined | 53.7% (87/162) | 42.7% (70/164) | 12.8% (21/164) |

TABLE 21

ITT (LOCF) median percent change from baseline in AK lesion count at EOS for individual 3-week treatment cycle regimen studies

| Study | 3.75% IMIQ | 2.5% IMIQ | Placebo |
| --- | --- | --- | --- |
| GW01-0703 | −82.3% | −66.7% | −23.6% |
| GW01-0705 | −78.9% | −66.7% | −22.5% |
| Combined | −80.0% | −66.7% | −23.6% |

In the three-week treatment cycle regimen studies, both 2.5% and 3.75% imiquimod creams demonstrated substantial efficacy for the treatment of AKs that was consistently significantly higher than that of placebo cream, with a trend towards greater efficacy with the higher concentration cream. Discontinuation rates for any cause, as well as for safety reasons, were low in all treatment groups, and as such, both imiquimod creams can be considered "well-tolerated." However, a larger number of subjects that were treated with either the 2.5% or 3.75% imiquimod cream required rest periods from the intended two 3-week treatment cycles. Rest periods and other measures of treatment tolerability (related adverse events, application site reactions, LSRs) demonstrated a dose dependent effect, with the highest incidences in the 3.75% 3-week cycle treatment group (data not shown).

Efficacy Analysis

To examine the impact of drug concentrations on efficacy, the four imiquimod treatment groups (2.5% and 3.75%, 2-week and 3-week regimens) can be combined by concentration, irrespective of treatment regimen. Data for 2.5% imiquimod (both 2- and 3-week treatment cycle groups) versus that of 3.75% imiquimod (both 2- and 3-week treatment cycle groups) were evaluated for efficacy effects of concentration, as shown in FIG. 1. Preliminary evaluation suggested an effect of drug concentration in favor of the 3.75% concentration for all three efficacy endpoints: complete clearance, partial clearance, and percent reduction from baseline of AK lesions. Preliminary evaluation suggested that the two regimens (2-week and 3-week treatment cycles) were comparable in terms of the efficacy endpoints. In addition, all four dosing regimens that were used showed statistically and clinically significant effectiveness in the reduction of AK lesions in the target population. The efficacy results for the two 2-cycle treatment regimens, i.e., the 2×2×2 weeks and the 3×3×3 weeks treatment cycles, suggested that the additional doses provided in the 3-week treatment cycle regimen resulted in no additional efficacy over that shown for the 2-week treatment cycle regimen. This finding was consistent with the rank order performance of the 3.75% product for all efficacy endpoints in all four individual Phase 3 studies. Therefore, from an efficacy standpoint, the 3.75% imiquimod cream, when applied daily in two 2-week treatment cycles, was believed to be an effective dose and regimen combination to treat actinic keratosis.

Example 25

Protocol for Studying Efficacy and Safety of 3.75% Imiquimod Cream Used in a 2×2×2 Treatment Cycle Prior to Photodynamic Therapy This example describes a protocol for a randomized, double-blinded, multicenter, placebo-controlled efficacy and safety study of 3.75% imiquimod cream applied in accordance with a 2×2×2 treatment cycle prior to photodynamic therapy for the treatment of actinic keratoses. The primary objective of this study is to assess AK clearance as determined by percent reduction in lesion count from baseline after treatment of the full face with imiquimod 3.75% cream for two 2-week cycles followed by field-directed PDT with ALA or observation. The secondary objectives include assessing complete clearance rates, cosmetic appearance (investigator and patient), and safety.

Description of Study

This study is an exploratory, phase IV, multi-center, open-label study of sequential treatment of AKs of the face with imiquimod 3.75% cream followed by PDT with ALA. Patients must have AKs as both of the products are approved for the treatment of AKs. All patients receive a 2-week cycle of daily application of imiquimod 3.75% cream to the entire face, followed by a 2-week no-treatment interval, and then by another 2-week cycle, as per the prescribing information. At 4 weeks post completion of topical treatment, patients are randomized to either treatment with short incubation field-directed PDT with ALA or to observation (no PDT treatment). Final assessment is 4 weeks from the randomization visit; it is anticipated that any residual local skin reaction from the prior topical treatment will have resolved sufficiently by that time to perform an assessment.

Randomization is only with respect to the PDT phase, as randomization in the imiquimod phase would require a much larger number of patients (as there would be 4 analyses groups instead of 2). An open-label design is used, as inclusion of a placebo-ALA with sham PDT in the PDT phase would increase logistical complexity; in addition, it would be difficult to maintain concealment of treatment assignment due to the known local effects of PDT. Only patients with AKs of the face are included in order to allow for more standardized photography; this also limits variations that might be due to anatomical differences between the face and the balding scalp. Field-directed PDT, rather than lesion-directed PDT, is used because field-directed PDT is more commonly used in clinical practice, including by the investigators. Final lesion assessments are performed by an evaluator without knowledge of treatment assignment in order to reduce potential bias.

This study will be conducted in accordance with International Conference of Harmonisation E6, Guideline for Good Clinical Practice, and applicable federal and state regulatory requirements.

Patient Selection

Sufficient patients with AKs are screened by each investigator to enroll up to a total of 20 patients, for a total of 60 patients across the 3 study centers. In the case an investigator is unable to enroll 20 patients, the remaining study center(s) may enroll up to 10 additional patients. However, no study center may enroll more than 30 patients, and the total study enrollment may not exceed 64 patients (4 additional patients included in total to account for potential patients in process of screening at the time the target of 60 subjects is achieved). Patients discontinuing early from the study will not be replaced.

Inclusion Criteria

Patients are allowed to participate in the study if they:
 are at least 18 years of age;
 have at least 10 and no more than 30 clinically typical AKs, not more than 1 mm in elevation, on the face (AKs on the balding scalp, immediately adjacent to eyes or ears, or on the lips or ears, should not be counted as they will not be treated); and
 are willing and able to give written informed consent, to authorize use and disclose medical information under the Health Insurance Portability and Accountability Act (HIPAA), and to participate in the study as an outpatient and comply with all study requirements.

Exclusion Criteria

Patients are not allowed to participate in this study if they:
 are patients with multiple hypertrophic AKs or other skin lesions (e.g. SCC) on the head that might require excluded treatment during the study;
 have known contradiction to treatment with imiquimod cream or PDT with ALA;
 have uncontrolled intercurrent or chronic illness that, in the opinion of the investigator, would limit compliance with study requirements, represent a potential safety risk, or require treatment with an excluded drug/treatment;
 are known to be systemically immunocompromised due to disease (e.g. known human immunodeficiency virus infection) or treatment (e.g. on greater than physiologic doses of systemic corticosteroids);
 are pregnant or nursing;
 have any dermatologic disease and/or condition in the treatment area(s) that may be exacerbated by treatment with imiquimod, cause difficulty with examination, or require treatment with an exclusionary treatment during the study;
 are currently participating in another clinical study;
 have received treatment anywhere on the body within the past 60 days with any of the following: ultraviolet (A, B, or C) therapy; systemic immunomodulators including but not limited to oral or parenteral corticosteroids at greater than physiologic doses (equivalent to 7.5 mg prednisone per day), interferons, anti-tumor necrosis factor agents, anti-interleukin agents, cytokines; chemotherapeutic or cytotoxic agents; or investigational agents;
 have received treatment for any condition on the head within the past 60 days with any of the following: imiquimod; photodynamic therapy; red or blue light source therapy even without a photosensitizer (e.g. ALA); cryotherapy or chemotherapy; surgical excision; curettage; topical corticosteroids; laser; dermabrasion; chemical peel; topical retinoids; topical 5'-fluorouracil; topical pimecrolimus or tacrolimus; or topical diclofenac; or
 have received any treatment for AKs on the head within the past 60 days.

Study Methodology

An overview of the study methodology is shown in FIG. 7.

Study Drug

The study drug consists of the imiquimod 3.75% packets containing 250 mg of cream per packet, in the marketed product configuration of 28 packets to a box. Each patient receives one box at Visit 2 and one box at Visit 3.

Topical Study Drug Administration:

The patient washes the face with water and mild soap prior to study drug application. For each dose, the patient applies the contents of up to 2 packets of study drug. The study drug should be applied as evenly as possible to the treatment area (if the full face, excluding lesions within 1 cm of eyes or mouth) and rubbed in gently until it vanishes. The treatment area is allowed to air dry; the treatment area should not be occluded with tape, bandages or tight clothing. Study drug remains on the application area for approximately 8 hours, after which it is washed off with water and mild soap.

Patients apply study drug once daily. If a patient forgets to apply a dose on a specific day, the patient should not make up the dose. The treatment duration for each 2-week cycle is not extended for any missed doses. Study drug is applied to the entire treatment area even if there appears to be clearing of some or all AKs in the treatment area.

During the time study drug is present on the skin, the patient should try to limit applying any other topicals, including make-up, over the treatment areas. Patients should be encouraged to use a hat or other covering to reduce solar exposure; otherwise, a sunscreen should be applied over the study drug only after it has been on the skin for at least 30 minutes. Topicals (prescription, over the counter, or cosmetic) should not be applied in the treatment areas immediately before the study drug is applied, nor on the morning of study center visits.

Patients should contact the study center if they experience any sign or symptom at the treatment area that restricts or prohibits their daily activity. The investigator will instruct the patient to come into the study center so that the patient's condition can be assessed. If the investigator determines from this assessment that dosing should be interrupted, a rest period will be allowed. Application of study cream should resume at the first scheduled dosing visit at which the LSR or adverse has been assessed by the investigator to have adequately resolved to resume dosing. An emollient and/or a light, nonocclusive dressing may be used over the treatment area during rest periods.

Packets used by the patient should be discarded. Unused packets should be returned to the study center. At the end of the study, unused study drug is disposed of appropriately with recording of the disposal on the study drug inventory log.

Photodynamic Therapy

ALA is in the marketed product configuration. As the ALA is dispensed to the patient, there is no study specific labeling of the clinical supplies. The lot number, date of dispensation, and initials of the person applying the ALA is recorded for each patient receiving PDT. The investigator evaluator should be blinded with respect to treatment assignment and not be involved in administering the PDT.

The treatment area is gently washed with acetone using 4×4 inch gauze pads. ALA is applied to the face, excluding the skin adjacent to the eyes, mouth or ears. After incubation for 1 hour, the treatment area is cleaned with water to remove unabsorbed solution. Protective eyewear is worn by the patient and the patient's face is exposed to blue light (BLU-U, 10 MW cm$^2$, Dusa Pharmaceuticals, Wilmington, Mass.) with the patient's face 6-8 inches from the lights. Light exposure time may be divided into fractions, with short recovery pauses, if required for patient tolerance. The total light exposure time is a full 16 minutes. Air cooling of the treatment site is used.

After PDT and prior to discharge from the study center, patients apply a physical (e.g. containing titanium dioxide) sunblock to the treatment area. Patients should be sent home wearing a hat to minimize sun exposure, with instructions to avoid exposing the treatment area to sunlight or intense artificial light for at least 48 hours (wear hat and use physical sun block). Patients should wash the treatment area at home with warm water and mild soap on the evening of the PDT administration.

Efficacy Assessments

AK Lesions:

Clinically visible and/or palpable AKs are counted within the treatment area (full face). Hypertrophic/hyperkeratotic AKs are counted separately from non-hypertrophic/hyperkeratotic AKs. AKs in areas that are not treated, e.g. immediately adjacent to the eyes or ears, or on the lips or ears, are not counted. Baseline lesions are distinguished from non-baseline lesions by using a transparent grid overlay to map the location of baseline lesions. Baseline hypertrophic and non-hypertrophic lesions are distinguished on grid map with different symbols. In counting AK lesions, an AK is considered as present, absent or unable to determine (UTD, e.g., due to LSRs).

Photographs:

Digital photographs, for example with a fixed mount photographic system with standardized distance and lighting, of the treatment area (full face) are obtained at the baseline, Visit 3, PDT randomization (prior to PDT) and FOS visits. Photographs should include at least a full frontal view; left and right 45° oblique views would be desirable. Each photograph should include a visible marker including the study number, the patient initials, the patient study identification number, and the visit date. Patients must have agreed to be photographed, including specifying on the photographic release whether they agreed to research usage of photographs and/or usage in presentations at medical meetings and/or in a publication in a medical journal(s).

Cosmetic Appearance:

The investigator assesses the cosmetic appearance of the entire treatment area (full face) of each patient at the baseline, PDT randomization (prior to PDT) and FOS visits using the global scoring system of Dover et al [Arch Dermatol. 2005; 141:1247-52]:

0: Facial skin is smooth to the touch, without significant fine lines or unevenness in pigmentation in any areas (cheeks, forehead, and the perioral area)

1: Facial skin shows 1 area (cheeks, forehead, or the perioral area) of significant roughness, dyspigmentation (hypopigmentation or hyperpigmentation), or fine lines 2: Facial skin shows 2 areas of significant roughness, dyspigmentation, or fine lines or shows roughness, dyspigmentation, and fine lines in 1 area 3: Facial skin shows 3 areas with significant roughness, dyspigmentation, or fine lines or shows roughness, dyspigmentation, and fine lines in 2 areas 4: Facial skin shows any degree of photodamage greater than 3.

Patient-Assessed Individual Photodamage Score:

Each patient self-assesses the cosmetic appearance of the entire treatment area (full face) using a mirror (or by palpation for skin roughness), at the baseline, PDT randomization (prior to PDT) and FOS visits. The patient should be instructed to self-assess for the following: fine lines, irregularities in pigmentation and skin roughness. The patient self-assigns an overall score using the following scale:

0: All are absent (i.e. no fine lines, no irregular pigmentation, and skin is smooth)

1: At least one is mild, but none are more than mild in severity

2: At least one is moderate, but none are more than moderate in severity

3: Only one is severe, but others may be moderate, mild or absent in severity

4: All are severe in severity

Safety Assessments

New AK Lesions:

New AK lesions inside or outside of the treatment area are considered as part of the underlying disease, and are not recorded as adverse events.

Adverse Events:

Clinically relevant AEs as reported by the patient or as determined by the investigator are recorded. The investigator or study coordinator records the AE using the most appropriate medical term, as determined by the investigator, the date of onset, the severity (see below), the date of resolution, investigator-determined causality (see below), treatment for the AE, and whether the AE was serious. Signs or symptoms in the treatment area that are considered to be clinical relevant should be recorded as application site AEs, e.g. application site pain.

Severity of an AE is graded as mild, moderate, or severe:

mild: patient is aware of the signs and symptoms but the signs and symptoms are easily tolerated.

moderate: signs and symptoms are sufficient to restrict, but not prevent usual daily activities severe: patient is unable to perform usual daily activities Investigator-determined causality for an AE will be categorized as:

related to study drug (or procedure, if applicable)

probably-related to study drug (or procedure, if applicable)

probably-not related to study drug (or procedure, if applicable)

not related to study drug (or procedure, if applicable)

An AE considered by the investigator to be related or probably-related to any drug, if applicable, is an adverse drug reaction (ADR). A serious AE or ADR is one that results in the following: death; life-threatening adverse experience; inpatient hospitalization or prolongation of existing hospitalization; persistent or significant disability/incapacity; congenital anomaly/birth defect.

An AE may also be considered serious if, based upon medical judgment, it jeopardizes the patient and may require medical or surgical intervention to prevent one of the outcomes listed above. A life-threatening event is any AE or ADR that places the patient, in the view of the investigator, at immediate risk of death from the reaction as it occurred. It does not include a reaction or event that had it occurred in a more severe form might have caused death. Serious AEs and ADRs will be reported to the IRB per applicable requirements. Serious ADRs considered related to either of the study drugs will be reported within 24 hours to the appropriate manufacturer.

Concomitant Medications:

The investigator will record any medications given in treatment of AE. Any medication taken by the patient during the course of the study should also be recorded.

The following concomitant medications or treatments should not be utilized during the study: psoralens plus ultraviolet A (PUVA) therapy; ultraviolet B (UVB) therapy; laser; systemic immunomodulators including but not limited to oral or parenteral corticosteroids at greater than physiologic doses (equivalent to 7.5 mg prednisone per day), interferons, anti-TNF agents, anti-interleukin agents and cytokines; chemotherapeutic or cytotoxic agents; and investigational agents. In addition, the following concomitant medications or treatments should not be used in the treatment area: any treatment of AKs, dermabrasion; chemical peel; imiquimod 5% cream; topical retinoids; 5-fluorouracil; diclofenac; tacrolimus; pimecrolimus; photodynamic therapy other than that specified in the protocol; red or blue light therapy even without a photosensitizer, cryotherapy or chemotherapy; surgical excision; curettage; or topical corticosteroids. These topical treatments may be used outside the treatment area to treat an intercurrent condition requiring urgent or semi-urgent treatment.

If a patient requires any restricted medication or treatment, the investigator will determine if there are significant safety concern (e.g. use investigational agent or cytotoxic agent) or if the treatment interferes with the ability to dose and/or adequately assess the treatment area. If so, dosing of study drug will cease and/or the PDT will not be administered if prior to the PDT randomization visit (Visit 4). If prior to the PDT randomization visit, the patient will complete Visit 4 procedures, other than receiving PDT, and enter the 8-week follow-up period. These patients will be analyzed separately as they will not be eligible for randomization. If there is not a significant safety concern and the restricted treatment does not interfere with the ability to dose and/or assess the treatment area, the investigator may allow the patient to continue in the study. If prior to Visit 4, the patient can be randomized to PDT or Observation (No PDT) and the patient can receive the PDT if the patient is assigned to PDT.

Patient Withdrawal or Discontinuation

Patients may withdraw from the study at any time for any reason without prejudice to their medical care. Patients may be discontinued from treatment by the investigator if he/she has determined that continuation or resumption of dosing is not in the patient's best interest. If a patient discontinues treatment or is discontinued by the investigator from treatment (including a decision not to receive PDT), if the patient has not completed Visit 4, the patient should complete the Visit 4 procedures, other than receiving PDT, and proceed into the follow-up period.

Example 26

Protocol for Studying Efficacy and Safety of 3.75% Imiquimod Cream Used in a 3×3×3 Treatment Cycle Prior to Photodynamic Therapy This example describes a protocol for a randomized, double-blinded, multicenter, placebo-controlled efficacy and safety study of 3.75% imiquimod cream applied in accordance with a 3×3×3 treatment cycle prior to photodynamic therapy for the treatment of actinic keratoses. The primary objective of this study is to assess AK clearance as determined by percent reduction in lesion count from baseline after treatment of the full face with imiquimod 3.75% cream for two 3-week cycles followed by field-directed PDT with ALA or observation. The secondary objectives include assessing complete clearance rates, cosmetic appearance (investigator and patient), and safety.

Description of Study

This study is an exploratory, phase IV, multi-center, open-label study of sequential treatment of AKs of the face with imiquimod 3.75% cream followed by PDT with ALA. Patients must have AKs as both of the products are approved for the treatment of AKs. All patients receive a 3-week cycle of daily application of imiquimod 3.75% cream to the entire face, followed by a 3-week no-treatment interval, and then by another 3-week cycle, as per the prescribing information. At 4 weeks post completion of topical treatment, patients are randomized to either treatment with short incubation field-directed PDT with ALA or to observation (no PDT treatment). Final assessment is 4 weeks from the randomization visit; it is anticipated that any residual local skin reaction from the prior topical treatment will have resolved sufficiently by that time to perform an assessment.

The study methodology, patient selection criteria, photodynamic therapy protocol, efficacy assessments, and safety assessments are as described above for Example 25. Administration of imiquimod therapy is as described above for Example 25, except that the imiquimod therapy is applied for two 3-week treatment cycles.

Example 27

Protocol for Studying Efficacy and Safety of 2.5% Imiquimod Cream Used in a 2×2×2 Treatment Cycle Prior to Photodynamic Therapy This example describes a protocol for a randomized, double-blinded, multicenter, placebo-controlled efficacy and safety study of 2.5% imiquimod cream applied in accordance with a 2×2×2 treatment cycle prior to photodynamic therapy for the treatment of actinic keratoses. The primary objective of this study is to assess AK clearance as determined by percent reduction in lesion count from baseline after treatment of the full face with imiquimod 2.5% cream for two 2-week cycles followed by field-directed PDT with ALA or observation. The secondary objectives include assessing complete clearance rates, cosmetic appearance (investigator and patient), and safety.

Description of Study

This study is an exploratory, phase IV, multi-center, open-label study of sequential treatment of AKs of the face with imiquimod 2.5% cream followed by PDT with ALA. Patients must have AKs as both of the products are approved for the treatment of AKs. All patients receive a 2-week cycle of daily application of imiquimod 2.5% cream to the entire face, followed by a 2-week no-treatment interval, and then by another 2-week cycle, as per the prescribing information. At 4 weeks post completion of topical treatment, patients are randomized to either treatment with short incubation field-directed PDT with ALA or to observation (no PDT treatment). Final assessment is 4 weeks from the randomization visit; it is anticipated that any residual local skin reaction from the prior topical treatment will have resolved sufficiently by that time to perform an assessment.

The study methodology, patient selection criteria, photodynamic therapy protocol, efficacy assessments, and safety assessments are as described above for Example 25. Administration of imiquimod therapy is as described above for Example 25, except that the imiquimod formulation comprises 2.5% (w/w) imiquimod.

Example 28

Protocol for Studying Efficacy and Safety of 2.5% Imiquimod Cream Used in a 3×3×3 Treatment Cycle Prior to Photodynamic Therapy This example describes a protocol for a randomized, double-blinded, multicenter, placebo-controlled efficacy and safety study of 2.5% imiquimod cream applied in accordance with a 3×3×3 treatment cycle prior to photodynamic therapy for the treatment of actinic keratoses. The primary objective of this study is to assess AK clearance as determined by percent reduction in lesion count from baseline after treatment of the full face with imiquimod 2.5% cream for two 3-week cycles followed by field-directed PDT with ALA or observation. The secondary objectives include assessing complete clearance rates, cosmetic appearance (investigator and patient), and safety.
Description of Study This study is an exploratory, phase IV, multi-center, open-label study of sequential treatment of AKs of the face with imiquimod 2.5% cream followed by PDT with ALA. Patients must have AKs as both of the products are approved for the treatment of AKs. All patients receive a 3-week cycle of daily application of imiquimod 2.5% cream to the entire face, followed by a 3-week no-treatment interval, and then by another 3-week cycle, as per the prescribing information. At 4 weeks post completion of topical treatment, patients are randomized to either treatment with short incubation field-directed PDT with ALA or to observation (no PDT treatment). Final assessment is 4 weeks from the randomization visit; it is anticipated that any residual local skin reaction from the prior topical treatment will have resolved sufficiently by that time to perform an assessment.

The study methodology, patient selection criteria, photodynamic therapy protocol, efficacy assessments, and safety assessments are as described above for Example 25. Administration of imiquimod therapy is as described above for Example 25, except that the imiquimod formulation comprises 2.5% (w/w) imiquimod and the imiquimod therapy is applied for two 3-week treatment cycles.

Example 29

Protocol for Studying Efficacy and Safety of 3.75% 1 Imiquimod Cream Used in a 2×2×2 Treatment Cycle Following Photodynamic Therapy This example describes a protocol for a randomized, double-blinded, multicenter, placebo-controlled efficacy and safety study of 3.75% imiquimod cream applied in accordance with a 2×2×2 treatment cycle following photodynamic therapy for the treatment of actinic keratoses. The primary objective of this study is to assess AK clearance as determined by percent reduction in lesion count from baseline after treatment of the full face with PDT with ALA followed by imiquimod 3.75% cream for two 2-week cycles. The secondary objectives include assessing complete clearance rates, cosmetic appearance (investigator and patient), and safety.
Description of Study This study is an exploratory, phase IV, multi-center, open-label study of sequential treatment of AKs of the face with PDT with ALA followed by imiquimod 3.75% cream. Patients must have AKs as both of the products are approved for the treatment of AKs. At the start of the trial, patients are randomized to either treatment with short incubation field-directed PDT with ALA or to observation (no PDT treatment). All patients then receive a 2-week cycle of daily application of imiquimod 3.75% cream to the entire face, followed by a 2-week no-treatment interval, and then by another 2-week cycle, as per the prescribing information. Final assessment is 4 weeks from the final 2-week visit; it is anticipated that any residual local skin reaction from the prior topical treatment will have resolved sufficiently by that time to perform an assessment.

The study methodology, patient selection criteria, photodynamic therapy protocol, efficacy assessments, and safety assessments are as described above for Example 25. Administration of therapy is as described above for Example 25, except that the imiquimod therapy follows photodynamic therapy.

Example 30

Protocol for Studying Efficacy and Safety of 3.75% Imiquimod Cream Used in a 3×3×3 Treatment Cycle Following Photodynamic Therapy This example describes a protocol for a randomized, double-blinded, multicenter, placebo-controlled efficacy and safety study of 3.75% imiquimod cream applied in accordance with a 3×3×3 treatment cycle following photodynamic therapy for the treatment of actinic keratoses. The primary objective of this study is to assess AK clearance as determined by percent reduction in lesion count from baseline after treatment of the full face with PDT with ALA followed by imiquimod 3.75% cream for two 3-week cycles. The secondary objectives include assessing complete clearance rates, cosmetic appearance (investigator and patient), and safety.
Description of Study This study is an exploratory, phase IV, multi-center, open-label study of sequential treatment of AKs of the face with PDT with ALA followed by imiquimod 3.75% cream. Patients must have AKs as both of the products are approved for the treatment of AKs. At the start of the trial, patients are randomized to either treatment with short incubation field-directed PDT with ALA or to observation (no PDT treatment). All patients then receive a 3-week cycle of daily application of imiquimod 3.75% cream to the entire face, followed by a 3-week no-treatment interval, and then by another 3-week cycle, as per the prescribing information. Final assessment is 4 weeks from the final 3-week treatment interval; it is anticipated that any residual local skin reaction from the prior topical treatment will have resolved sufficiently by that time to perform an assessment.

The study methodology, patient selection criteria, photodynamic therapy protocol, efficacy assessments, and safety assessments are as described above for Example 25. Administration of therapy is as described above for Example 25, except that the imiquimod therapy follows photodynamic therapy, and the imiquimod therapy is applied for two 3-week treatment cycles.

Example 31

Protocol for Studying Efficacy and Safety of 2.5% Imiquimod Cream Used in a 2×2×2 Treatment Cycle Following Photodynamic Therapy This example describes a protocol for a randomized, double-blinded, multicenter, placebo-controlled efficacy and safety study of 2.5% imiquimod cream applied in accordance with a 2×2×2 treatment cycle following photodynamic therapy for the treatment of actinic keratoses. The primary objective of this study is to assess AK clearance as determined by percent reduction in lesion count from baseline after treatment of the full face with PDT with ALA followed by imiquimod 2.5% cream for two 2-week cycles. The secondary objectives include assessing complete clearance rates, cosmetic appearance (investigator and patient), and safety.

Description of Study

This study is an exploratory, phase IV, multi-center, open-label study of sequential treatment of AKs of the face with PDT with ALA followed by imiquimod 2.5% cream. Patients must have AKs as both of the products are approved for the treatment of AKs. At the start of the trial, patients are randomized to either treatment with short incubation field-directed PDT with ALA or to observation (no PDT treatment). All patients then receive a 2-week cycle of daily application of imiquimod 2.5% cream to the entire face, followed by a 2-week no-treatment interval, and then by another 2-week cycle, as per the prescribing information. Final assessment is 4 weeks from the final 2-week treatment interval; it is anticipated that any residual local skin reaction from the prior topical treatment will have resolved sufficiently by that time to perform an assessment.

The study methodology, patient selection criteria, photodynamic therapy protocol, efficacy assessments, and safety assessments are as described above for Example 25. Administration of therapy is as described above for Example 25, except that the imiquimod therapy follows photodynamic therapy, and the imiquimod formulation comprises 2.5% (w/w) imiquimod.

Example 32

Protocol for Studying Efficacy and Safety of 2.5% Imiquimod Cream Used in a 3×3×3 Treatment Cycle Following Photodynamic Therapy This example describes a protocol for a randomized, double-blinded, multicenter, placebo-controlled efficacy and safety study of 2.5% imiquimod cream applied in accordance with a 3×3×3 treatment cycle following photodynamic therapy for the treatment of actinic keratoses. The primary objective of this study is to assess AK clearance as determined by percent reduction in lesion count from baseline after treatment of the full face with PDT with ALA followed by imiquimod 2.5% cream for two 3-week cycles. The secondary objectives include assessing complete clearance rates, cosmetic appearance (investigator and patient), and safety.

Description of Study

This study is an exploratory, phase IV, multi-center, open-label study of sequential treatment of AKs of the face with PDT with ALA followed by imiquimod 2.5% cream. Patients must have AKs as both of the products are approved for the treatment of AKs. At the start of the trial, patients are randomized to either treatment with short incubation field-directed PDT with ALA or to observation (no PDT treatment). All patients then receive a 3-week cycle of daily application of imiquimod 2.5% cream to the entire face, followed by a 3-week no-treatment interval, and then by another 3-week cycle, as per the prescribing information. Final assessment is 4 weeks from the final 3-week treatment interval; it is anticipated that any residual local skin reaction from the prior topical treatment will have resolved sufficiently by that time to perform an assessment.

The study methodology, patient selection criteria, photodynamic therapy protocol, efficacy assessments, and safety assessments are as described above for Example 25. Administration of therapy is as described above for Example 25, except that the imiquimod therapy follows photodynamic therapy, the imiquimod formulation comprises 2.5% (w/w) imiquimod, and the imiquimod therapy is applied for two 3-week treatment cycles.

Example 33

Protocol for Treatment of Actinic Keratoses of the Fact with Imiquimod 3.75% Cream Followed by Photodynamic Therapy This example describes a protocol for an interventional, Phase IV study designed to explore the effect of treating actinic keratoses of the face with imiquimod 3.75% cream followed by photodynamic therapy in comparison to treatment with imiquimod alone. Incorporated herein by reference in its entirety is the study sponsored and information provided by: Tennessee Clinical Research Center and collaborator Graceway Pharmaceuticals, LLC, Study entitled "Treatment of Actinic Keratoses of the Face With Imiquimod 3.75% Cream Followed by Photodynamic Therapy", and ClinicalTrials.gov Identifier No.: NCT01203878.

For this study, the primary outcome measures are the actinic keratosis count (time frame: week 18 (4 weeks after randomization visit), wherein the actinic keratosis count is measured as the percent change in actinic keratosis count as compared to the baseline lesion count. The secondary outcome measures include assessing complete clearance rates and cosmetic appearance (investigator and patient).

The estimated enrollment for this study is 60 patients, with a study start date of September 2010 and an estimated study completion date of October 2011. The estimated primary completion date, i.e., the final data collection date for primary outcome measure, is September 2011.

Description of Study

Actinic keratoses are common skin lesions associated with solar ultraviolet radiation exposure. Some actinic keratoses may develop into skin cancers. Imiquimod 3.75% cream is an approved treatment for actinic keratoses that utilizes a regimen of application to the entire face or balding scalp of up to 2 packets of cream daily for two 2-week cycles, separated by a 2-week no treatment interval. Photodynamic therapy with aminolevulinic acid (ALA) 20% topical solution is also an approved treatment for actinic keratoses. ALA is applied to actinic keratoses, and after an incubation period, is excited with light. Although approved as a lesion-directed treatment for actinic keratoses, treatment of a field (e.g. face) with photodynamic therapy is commonly performed.

Treatment with photodynamic therapy followed by imiquimod 5% cream has been reported in patients with actinic keratoses, basal cell carcinoma and Bowen's disease, and treatment with imiquimod 5% cream followed by photodynamic therapy in patients with vulvar intraepithelial neoplasia. There are, however, no prior studies on the safety and/or efficacy of using topical imiquimod 3.75% in conjunction with photodynamic therapy in the treatment of actinic keratoses. This study uses an open-label parallel cohort design in which all patients receive treatment with imiquimod 3.75% cream, and subsequently are randomized to receive either photodynamic therapy or observation. The study arms are described below in Table 22:

TABLE 22

| Arms | Assigned Interventions |
|---|---|
| Imiquimod/photodynamic therapy: Experimental Imiquimod 3.75% applied to the entire face followed by photodynamic therapy of the entire face. Intervention: Drug: Imiquimod/photodynamic therapy | Drug: Imiquimod/photodynamic therapy Imiquimod 3.75% cream, up to 2 packets, applied topically daily for two 2-week cycles separated by a no-treatment interval of 2-weeks, followed 4 weeks later by photodynamic therapy with 20% aminolevulinic acid and bluelight exposure Other Names: Zyclara (imiquimod 3.75% cream) Levulan Kerasticks (aminolevulinic acid 20% solution) |
| Imiquimod followed by observation: Active Comparator Imiquimod 3.75% applied to the entire face followed by observation Intervention: Drug: Imiquimod only | Drug: Imiquimod only Imiquimod 3.75% cream, up to 2 packets, applied topically daily for two 2-week cycles separated by a no-treatment interval of 2-weeks, followed observation Other Name: Zyclara (imiquimod 3.75% cream) |

Example 34

An Exploratory, Open-Label Study of Sequential Field-Directed Treatment of Actinic Keratoses of the Face with Imiquimod 3.75% Cream Followed by Photodynamic Therapy This example describes results obtained from a Phase IV study of sequential treatment of AKs of the face with imiquimod 3.75% cream followed by PDT with ALA. The primary objective of this study was to assess AK clearance as determined by percent reduction in lesion count from baseline after treatment of the full face with imiquimod 3.75% cream for two 2-week cycles followed by field-directed PDT with ALA or observation. The secondary objectives included assessing complete clearance rates, cosmetic appearance, and safety.

Study Design

In this study, all patients received a 2-week cycle of daily application of imiquimod 3.75% cream to the entire face, followed by a 2-week no-treatment interval, and then by another 2-week cycle of daily application, as per the prescribing information. At four weeks post completion of topical treatment, patients were randomized to receive either treatment with short incubation field-directed PDT with ALA or to receive observation only (no PDT treatment). A final lesion count was performed eight weeks after PDT/observation.

Key Inclusion Criteria

Subjects were included in this study if they were at least 18 years of age; and had at least 10 and no more than 30 clinically typical AKs, not more than 1 mm in elevation, on the face (AKs on the balding scalp, immediately adjacent to eyes or ears, or on the lips or ears, were not counted).

Key Exclusion Criteria

Subjects were excluded from this study if they had received treatment for any condition on the head within the previous 60 days with any of the following: imiquimod; photodynamic therapy; red or blue light source therapy even without a photosensitizer (e.g., ALA); cryotherapy or chemotherapy; surgical excision; curettage; topical corticosteroids; laser; dermabrasion; chemical peel; topical retinoids; topical 5'-fluorouracil; topical pimecrolimus or tacrolimus; or topical diclofenac; or if they had received any treatment for AKs on the head within the previous 60 days.

Study Methodology

An overview of the schedule of events for the trial is shown in FIG. 7.

Results

The efficacy of the treatment, as measured by lesion counts at the end of study visit ("Visit 5") as compared to baseline, is shown in FIG. 8 and Table 23 below. For the group receiving imiquimod followed by photodynamic therapy treatment ("PDT group"), 55% exhibited complete clearance at the end of study visit (5/9). In contrast, for the group receiving imiquimod only ("observation group"), complete clearance at the end of study visit was only 25% (2/8). The average percent reduction in the number of lesions was 83% at the end of study visit for the observation group and 81% at the end of study visit for the PDT group. Drug accountability showed strong drug compliance in all subjects. The number of hypertrophic lesions present at baseline was ~1%.

TABLE 23

Efficacy—lesion counts as compared to baseline

| Subject Number | Subject Initials | % Reduction at Visit 5 |
|---|---|---|
| Observation group | | |
| 001 | LLS | 65% |
| 004 | LLJ | 79% |
| 005 | TDB | 70% |
| 010 | JBB | 95% |
| 006 | NRW | 67% |
| 007 | WWH | 88% |
| 001 | ALB | 100% |
| 003 | D-Z | 100% |
| PDT Group | | |
| 002 | JCD | 44% |
| 003 | MJC | 100% |
| 006 | L-L | 8% |
| 007 | MJA | 100% |
| 009 | MBK | 100% |
| 004 | JBK | 85% |
| 005 | VLM | 89% |
| 002 | TFC | 100% |
| 004 | PWH | 100% |

Changes in total lesion count over time, mean lesion count over time, and median lesion count over time are shown in FIG. 9 and in Table 24 below:

Table 24

Total lesion counts tracked from baseline

| Observation group subjects | Visit 1 | Visit 4 | Visit 5 |
|---|---|---|---|
| Total number of lesions | 146 | 21 | 21 |
| Mean | 18 | 3 | 3 |
| Median | 18 | 3 | 3 |
| Std dev | 5.60 | 2.56 | 2.39 |
| Min | 10 | 0 | 0 |
| Max | 29 | 5 | 6 |
| PDT group subjects | Visit 1 | Visit 4 | Visit 5 |
| Total number of lesions | 179 | 25 | 28 |
| Mean | 20 | 3 | 3 |

Table 24-continued

| Total lesion counts tracked from baseline | | | |
|---|---|---|---|
| Median | 19 | 3 | 0 |
| Std dev | 5.58 | 2.33 | 4.70 |
| Min | 13 | 0 | 0 |
| Max | 27 | 6 | 12 |

Cosmetic improvement was measured as described in Example 25 above. The results in cosmetic improvement for subjects having a baseline of category 3 are shown in Table 25 below. In this Example, category 3 is defined as facial skin that shows three areas (cheeks, forehead, and perioral area) with significant roughness, dyspigmentation, or fine lines or shows roughness, dyspigmentation, and fine lines in two areas. For the observation group, there was an average improvement of 2.25. For the PDT group, there was an average improvement of 2.17.

TABLE 25

| Cosmetic improvement for subjects having a baseline of category 3 | | | | | |
|---|---|---|---|---|---|
| Arm | Site # | Subject # | Visit 1 | Visit 5 | Improvement |
| OBS | 10 | 001 | 3 | 1 | 2 |
| OBS | 10 | 004 | 3 | 1 | 2 |
| OBS | 10 | 011 | 3 | 0 | 3 |
| OBS | 12 | 001 | 3 | 1 | 2 |
| PDT | 10 | 002 | 3 | 1 | 2 |
| PDT | 10 | 003 | 3 | 0 | 3 |
| PDT | 10 | 007 | 3 | 1 | 2 |
| PDT | 10 | 009 | 3 | 0 | 3 |
| PDT | 12 | 002 | 3 | 1 | 2 |
| PDT | 12 | 004 | 3 | 2 | 1 |

The results in cosmetic improvement for subjects having a baseline of category 2 are shown in Table 26 below. In this Example, category 2 is defined as facial skin that shows two areas (cheeks, forehead, and perioral area) with significant roughness, dyspigmentation, or fine lines or shows roughness, dyspigmentation, and fine lines in one area. For the observation group, there was an average improvement of 1.0. For the PDT group, there was an average improvement of 0.67.

TABLE 26

| Cosmeticimprovement for subjects having a baseline of category 2 | | | | | |
|---|---|---|---|---|---|
| Arm | Site # | Subject # | Visit 1 | Visit 5 | Improvement |
| OBS | 10 | 005 | 2 | 1 | 1 |
| OBS | 10 | 010 | 2 | 1 | 1 |
| OBS | 11 | 007 | 2 | 1 | 1 |
| OBS | 12 | 003 | 2 | 1 | 1 |
| PDT | 10 | 006 | 2 | 2 | 0 |
| PDT | 11 | 004 | 2 | 1 | 1 |
| PDT | 11 | 005 | 2 | 1 | 1 |

Adverse events, excluding not-related events, are shown in Table 27 below.

TABLE 27

| Adverse events | | | | | | | |
|---|---|---|---|---|---|---|---|
| Arm | Site # | Subject # | AE Term | Drug relationship | PDT relationship | Severity | Serious |
| OBS | 12 | 001 | Flu like symptoms | Probably related | Not related | Mild | No |
| OBS | 12 | 003 | Fever blister | Probably related | Not related | Mild | No |
| PDT | 10 | 003 | Erythema | Related | Not related | Mild | No |
| PDT | 11 | 005 | HSV outbreak lower lip | Not related | Probably related | Mild | No |
| PDT | 12 | 002 | Headache | Probably related | Not related | Mild | No |
| PDT | 12 | 004 | Facial pain | Probably related | Not related | Moderate | No |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating actinic keratosis (AK) in a subject in need thereof, the method comprising:
   topically applying to a treatment area on the subject an imiquimod composition comprising from about 1% (w/w) to about 4.25% (w/w) imiquimod, wherein the step of applying the imiquimod composition to the treatment area comprises a first treatment and a second treatment period, wherein the first and second treatment periods are separated by a non-treatment period and wherein each of the first treatment period, the second treatment period, and the non-treatment period is for a length of time of up to three weeks; and
   subsequent to the topical application of the imiquimod composition, administering photodynamic therapy to the treatment area or to an AK lesion in the treatment area, wherein the photodynamic therapy treatment is administered within four weeks after completion of the imiquimod treatment; thereby treating AK in the subject.

2. The method of claim 1, wherein applying the imiquimod composition to the treatment area comprises a first two-week treatment period and a second two-week treatment period, wherein the first and second treatment periods are separated by a two-week non-treatment period.

3. The method of claim 1, wherein applying the imiquimod composition to the treatment area comprises a first three-week treatment period and a second three-week treatment period, wherein the first and second treatment periods are separated by a three-week non-treatment period.

4. The method of claim 1, wherein the imiquimod composition is administered once daily.

5. The method of claim 1, wherein the imiquimod composition comprises imiquimod in an amount of about 2.5% (w/w).

6. The method of claim 1, wherein the imiquimod composition comprises imiquimod in an amount of about 3.75% (w/w).

7. The method of claim 1, wherein the imiquimod composition is applied as a field-directed treatment.

8. The method of claim 1, wherein the photodynamic therapy comprises:
   administering a topical formulation comprising a photoreactive compound to the treatment area or to an AK lesion in the treatment area; and
   irradiating the treatment area of the subject with a light having a wavelength corresponding to the characteristic light absorption wavelength of the photoreactive compound.

9. The method of claim 8, wherein the photoreactive compound is aminolevulinic acid (ALA).

10. The method of claim 1, wherein the treatment area is the face or scalp.

11. The method of claim 1, wherein the AK lesion is a clinically visible, palpable, non-palpable, or non-hypertrophic lesion.

12. The method of claim 1, wherein the photodynamic therapy treatment is administered within 14 days after completion of the imiquimod treatment.

13. The method of claim 1, wherein the method results in the clearance of at least 75% of the baseline AK lesions in the subject.

14. The method of claim 13, wherein the method results in the complete clearance of AK lesions in the subject.

15. A method of treating actinic keratosis (AK) in a subject in need thereof, the method comprising:
   topically applying to a treatment area on the subject a composition comprising imiquimod in an amount of about 2.5% (w/w) or about 3.75% (w/w) over a first two-week treatment period;
   topically applying to the treatment area on the subject the imiquimod composition over a second two-week treatment period, wherein the first two-week treatment period and the second two-week treatment period are separated by a two-week non-treatment period; and
   subsequent to the application of the imiquimod composition, administering photodynamic therapy to the treatment area or to an AK lesion in the treatment area, wherein the photodynamic therapy treatment is administered within four weeks after completion of the imiquimod treatment; thereby treating AK in the subject.

* * * * *